(12) United States Patent
Moorman

(10) Patent No.: US 7,691,869 B2
(45) Date of Patent: Apr. 6, 2010

(54) PYRROLOTRIAZOLOPYRIMIDINE DERIVATIVES, PHARMACEUTICAL COMPOSITIONS CONTAINING THEM AND METHODS OF TREATING CONDITIONS AND DISEASES MEDIATED BY THE ADENOSINE $A_{2A}$ RECEPTOR ACTIVITY

(75) Inventor: Allan R. Moorman, Durham, NC (US)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 54 days.

(21) Appl. No.: 12/056,403

(22) Filed: Mar. 27, 2008

(65) Prior Publication Data

US 2008/0242672 A1 Oct. 2, 2008

(51) Int. Cl.
*A61K 31/505* (2006.01)
*C07D 491/00* (2006.01)
(52) U.S. Cl. ...................... 514/267; 544/251
(58) Field of Classification Search ............. 514/267; 544/251
See application file for complete search history.

(56) References Cited

U.S. PATENT DOCUMENTS

| | | | | |
|---|---|---|---|---|
| 5,565,460 | A | 10/1996 | Suzuki et al. | 514/259 |
| 5,935,964 | A | 8/1999 | Baraldi et al. | 514/267 |
| 6,653,315 | B2 | 11/2003 | Tulshian et al. | 514/267 |
| 6,664,252 | B2 | 12/2003 | Castelhano et al. | 514/228.5 |
| 6,916,811 | B2 | 7/2005 | Boyle et al. | 514/233 |
| 7,064,204 | B2 | 6/2006 | Baraldi et al. | 544/251 |
| 7,067,655 | B2 | 6/2006 | Neustadt et al. | 544/115 |
| 7,368,449 | B2 | 5/2008 | Neustadt et al. | 514/252.16 |
| 2005/0239795 | A1 | 10/2005 | Neustadt et al. | 514/252.16 |
| 2006/0128694 | A1 | 6/2006 | Grzelak et al. | 514/220 |
| 2007/0066620 | A1 | 3/2007 | Neustadt et al. | 514/252.11 |
| 2007/0072867 | A1 | 3/2007 | Boyle et al. | 514/252.16 |

FOREIGN PATENT DOCUMENTS

| | | |
|---|---|---|
| WO | WO 95/01356 | 1/1995 |
| WO | WO 97/05138 | 2/1997 |
| WO | WO 98/52568 | 11/1998 |
| WO | WO 01/92264 | 12/2001 |
| WO | WO 03/032996 | 4/2003 |
| WO | WO 2005/103055 | * 11/2005 |

OTHER PUBLICATIONS

Thomas, T. and Spyer, K.M., A Novel Influence of Adenosine on Ongoing Activity in Rat Rostral Ventrolateral Medulla, Neuroscience vol. 88, No. 4, pp. 1213-1223 (1999).*
Gatta et al., "Synthesis of imidazo[1,2-c]pyrazolo[4,3-e]pyrimidines, pyrazolo[4,3-e]1,2,4-triazolo[1,5-c]pyrimidines and 1,2,4-triazolo[5,1-i]purines: new potent adenosine $A_2$ receptor antagonists", *Eur. J. Med. Chem.* 1993, 28, 569-576.

Baraldi et al., "Pyrazolo[4,3-e]-1,2,4-triazolo[1,5-c]pyrimidine Derivatives: Potent and Selective $A_{2A}$ Adenosine Antagonists", *J. Med. Chem.* 1996, 39, 1164-1171.
Baraldi et al., "Design, Synthesis and Biological Evaluation of a Second Generation of Pyrazolo[4,3-e]-1,2,4-triazolo[1,5-c]pyrimidines as Potent and Selective $A_{2A}$ Adenosine Receptor Antagonists", *J. Med. Chem.* 1998, 41, 2126-2133.
Baraldi et al., "Design, Synthesis, and Biological Evaluation of $C^9$- and $C^2$-Substituted Pyrazolo[4,3-e]-1,2,4-triazolo[1,5-c]pyrimidines as New $A_{2A}$ and $A_3$ Adenosine Receptor Antagonists", *J. Med. Chem.* 2003, 46, 1229-1241.
Neustadt et al., "Potent, selective, and orally active adenosine $A_{2A}$ receptor antagonists: Arylpiperazine derivatives of pyrazolo[4,3-e]-1,2,3-triazolo[1,5-c]pyrimidines", *Bioorganic & Medicinal Chemistry Letters* 2007, 17, 1376-1380.
Wei et al., "3D-Pharmacophore Models for Selective $A_{2A}$ and $A_{2B}$ Adenosine Receptor Antagonists", *Eur. J. Chem. Inf. Model.* 2007, 47, 613-625.

* cited by examiner

*Primary Examiner*—James O Wilson
*Assistant Examiner*—Erich A Leeser
(74) *Attorney, Agent, or Firm*—Paivi Kukkola

(57) ABSTRACT

The present invention provides compounds of the formula (I)

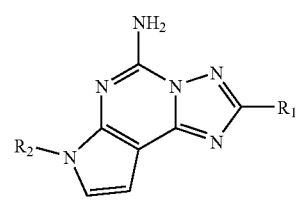

wherein $R_1$ and $R_2$ have meaning as defined herein in the specification. The compounds of formula (I) are adenosine $A_{2A}$ receptor antagonists and, thus, may be employed for the treatment of conditions and diseases mediated by the adenosine $A_{2A}$ receptor activity. Such conditions include, but are not limited to, diseases of the central nervous system such as depression, cognitive function diseases and neurodegenerative diseases such as Parkinson's disease, senile dementia as in Alzheimer's disease or psychoses and stroke. The compounds of the present invention may also be employed for the treatment of attention related disorders such as attention deficit disorder (ADD) and attention deficit hyperactivity disorder (ADHD), extra pyramidal syndrome, e.g., dystonia, akathisia, pseudoparkinsonism and tardive dyskinesia, and disorders of abnormal movement such as restless leg syndrome (RLS) and periodic limb movement in sleep (PLMS); cirrhosis, and fibrosis and fatty liver; dermal fibrosis in diseases such as scleroderma; and the mitigation of addictive behavior. In particular, the compounds of the present invention may be employed to improve motor-impairment due to neurodegenerative diseases such as Parkinson's disease.

17 Claims, 1 Drawing Sheet

PYRROLOTRIAZOLOPYRIMIDINE DERIVATIVES, PHARMACEUTICAL COMPOSITIONS CONTAINING THEM AND METHODS OF TREATING CONDITIONS AND DISEASES MEDIATED BY THE ADENOSINE $A_{2A}$ RECEPTOR ACTIVITY

FIELD OF THE INVENTION

The present invention relates to novel triazolopyrimidine derivatives, pharmaceutical compositions containing them, and methods of treating conditions and diseases mediated by the adenosine $A_{2A}$ receptor activity, by employing such compounds.

BACKGROUND OF THE INVENTION

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors, i.e., adenosine $A_1$, $A_{2A}$, $A_{2B}$ and $A_3$ receptors, of which the $A_1$ and $A_{2A}$ receptors are of high-affinity and the $A_{2B}$ and $A_3$ receptors are of low-affinity. The $A_1$ and $A_3$ receptors inhibit the activity of the enzyme adenylate cyclase, whereas the $A_{2A}$ and $A_{2B}$ receptors stimulate the activity of the same enzyme. Analogs of adenosine able to interact as antagonists with the $A_1$, $A_{2A}$, $A_{2B}$ and $A_3$ receptors have been identified.

Selective antagonists for the $A_{2A}$ receptor are of pharmacological interest because of their reduced level of side effects. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases such as Parkinson's disease, senile dementia as in Alzheimer's disease, psychoses and stroke. Furthermore, $A_{2A}$ antagonists may be employed for the treatment of attention related disorders such as attention deficit disorder (ADD) and attention deficit hyperactivity disorder (ADHD), extra pyramidal syndrome, e.g., dystonia, akathisia, pseudoparkinsonism and tardive dyskinesia, and disorders of abnormal movement such as restless leg syndrome (RLS) and periodic limb movement in sleep (PLMS) as disclosed in WO 02/055083, WO 05/044245 and WO 06/132275. U.S. Patent Application Publication No. 2007037033 discloses adenosine $A_{2A}$ antagonists as useful agents for the treatment of amyotrophic lateral sclerosis. WO 01/058241 discloses the treatment of cirrhosis, and fibrosis and fatty liver by employing adenosine $A_{2A}$ antagonists. WO 06/009698 describes adenosine $A_{2A}$ antagonists as useful for the mitigation of addictive behavior. Recently, Chan et al. have demonstrated (*Arthritis & Rheumatism*, 54(8), 2632-2642, 2006) that adenosine $A_{2A}$ antagonists may be employed for the treatment and prevention of dermal fibrosis in diseases such as scleroderma.

Certain triazolopyrimidine derivatives have been disclosed previously as adenosine $A_{2A}$ receptor antagonists, e.g., those as described in WO 95/01356, U.S. Pat. No. 5,565,460, WO 97/05138, WO 98/52568, WO 01/92264, WO 03/032996, and WO 05/103055.

SUMMARY OF THE INVENTION

The present invention provides compounds of the formula

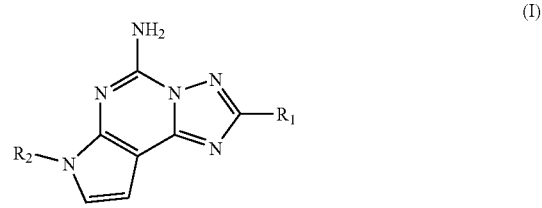

(I)

wherein
  $R_1$ is optionally substituted $C_3$-$C_7$ cycloalkyl, optionally substituted $C_6$-$C_{10}$ aryl, optionally substituted heteroaryl or optionally substituted heterocyclyl;
  $R_2$ is —$(CR_3R_4)_m$—Y—$(CR_5R_6)_n$—Z-Q in which
    $R_3$, $R_4$, $R_5$ and $R_6$ are, independently from each other, hydrogen, $C_1$-$C_6$ alkyl or $C_3$-$C_{12}$ cycloalkyl;
    m and n are, independently from each other, an integer from 1 to 6;
    Y is absent, CH=CH, C≡C, O, S, $NR_7$ in which $R_7$ is hydrogen or $C_1$-$C_4$ alkyl;
    Z is absent, O, S or $NR_8$ in which $R_8$ is hydrogen or $C_1$-$C_4$ alkyl;
    Q is optionally substituted $C_6$-$C_{10}$ aryl or optionally substituted heteroaryl; or
    Q is a monovalent radical selected from the group consisting of

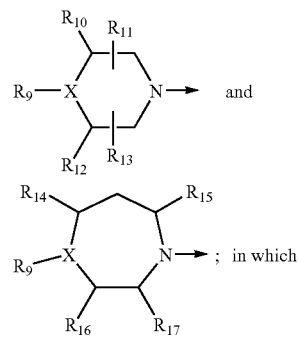

and

; in which $R_9$ is optionally substituted $C_1$-$C_6$ alkyl, optionally substituted $C_3$-$C_{12}$ cycloalkyl, optionally substituted $C_6$-$C_{10}$ aryl, optionally substituted heteroaryl, optionally substituted aralkyl, optionally substituted heteroaralkyl, heterocyclyl or acyl;
    $R_{10}$ and $R_{11}$ are, independently from each other, hydrogen, optionally substituted $C_1$-$C_3$alkyl; or
    $R_{10}$ and $R_{11}$, provided they are attached to the same carbon atom, combined are alkylene which together with the carbon atom to which they are attached form a 3- to 7-membered spirocyclic ring;

$R_{12}$, $R_{13}$, $R_{14}$, $R_{15}$, $R_{16}$ and $R_{17}$ are, independently from each other, hydrogen or optionally substituted $C_1$-$C_3$ alkyl;

X is N or CH; provided that Z is absent;

or a pharmaceutically acceptable salt thereof.

The compounds of the present invention are adenosine $A_{2A}$ receptor antagonists and, thus, may be employed for the treatment of conditions and diseases mediated by the adenosine $A_{2A}$ receptor activity. Such conditions include, but are not limited to, diseases of the central nervous system such as depression, cognitive function diseases and neurodegenerative diseases such as Parkinson's disease, senile dementia as in Alzheimer's disease or psychoses and stroke. The compounds of the present invention may also be employed for the treatment of attention related disorders such as attention deficit disorder (ADD) and attention deficit hyperactivity disorder (ADHD), extra pyramidal syndrome, e.g., dystonia, akathisia, pseudoparkinsonism and tardive dyskinesia, and disorders of abnormal movement such as restless leg syndrome (RLS) and periodic limb movement in sleep (PLMS); cirrhosis, and fibrosis and fatty liver; dermal fibrosis in diseases such as scleroderma; and the mitigation of addictive behavior. In particular, the compounds of the present invention may be employed to improve motor-impairment due to neurodegenerative diseases such as Parkinson's disease.

DETAILED DESCRIPTION OF THE INVENTION

Figure 1:
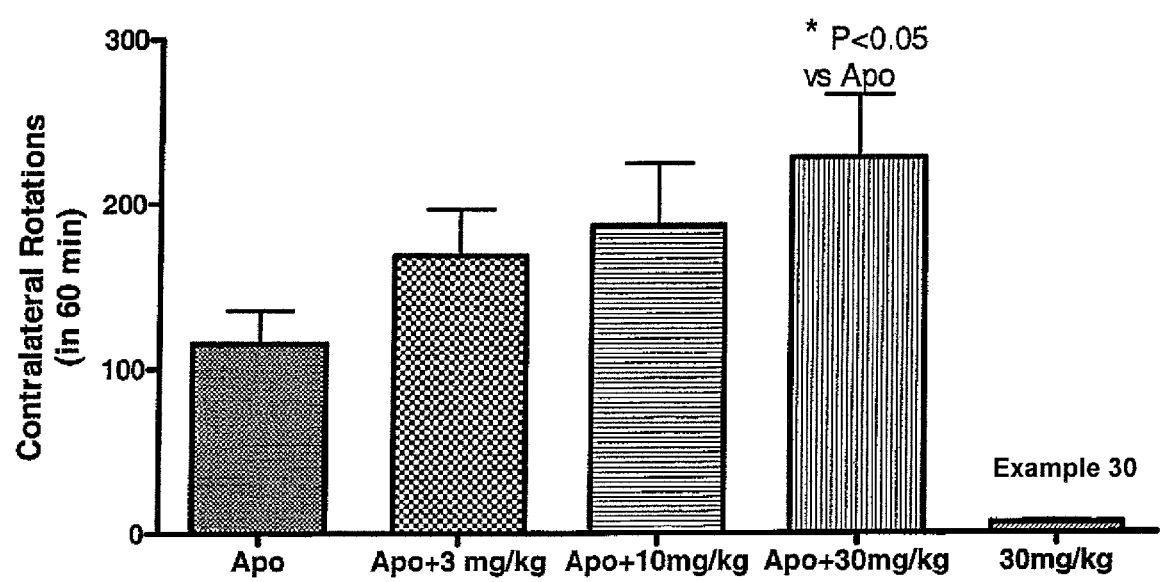
FIG. 1 shows the effect of the compound of Example 30 on rotational responses in 6-OHDA lesioned rats challenged with an intraperitoneal dose of 0.02 mg/kg of apomorphine hydrochloride, following a single intraperitoneal administration of the compound of Example 30 at doses of 3, 10 and 30 mg/kg, respectively.

As described herein above, the present invention provides compounds of the formula

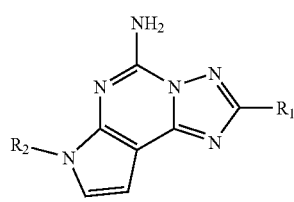

(I)

wherein $R_1$ is optionally substituted $C_3$-$C_7$ cycloalkyl, optionally substituted $C_6$-$C_{10}$ aryl, optionally substituted heteroaryl or optionally substituted heterocyclyl;

$R_2$ is —$(CR_3R_4)_m$—Y—$(CR_5R_6)_n$—Z-Q in which $R_3$, $R_4$, $R_5$ and $R_6$ are, independently from each other, hydrogen, $C_1$-$C_6$ alkyl or $C_3$-$C_{12}$ cycloalkyl;

m and n are, independently from each other, an integer from 1 to 6;

Y is absent, O, S, $NR_7$, CH=CH or C≡C in which $R_7$ is hydrogen or $C_1$-$C_4$ alkyl;

Z is absent, O, S or $NR_8$ in which $R_8$ is hydrogen or $C_1$-$C_4$ alkyl;

Q is optionally substituted $C_6$-$C_{10}$ aryl or optionally substituted heteroaryl; or Q is a monovalent radical selected from the group consisting of

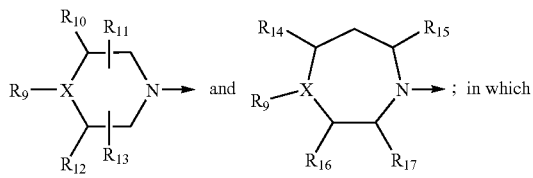

$R_9$ is optionally substituted $C_1$-$C_6$ alkyl, optionally substituted $C_3$-$C_{12}$ cycloalkyl, optionally substituted $C_6$-$C_{10}$ aryl, optionally substituted heteroaryl, optionally substituted aralkyl, optionally substituted heteroaralkyl, heterocyclyl or acyl;

$R_{10}$ and $R_{11}$ are, independently from each other, hydrogen, optionally substituted $C_1$-$C_3$ alkyl; or $R_{10}$ and $R_{11}$ provided they are attached to the same carbon atom, combined are alkylene which together with the carbon atom to which they are attached form a 3- to 7-membered spirocyclic ring;

$R_{12}$, $R_{13}$, $R_{14}$, $R_{15}$, $R_{16}$ and $R_{17}$ are, independently from each other, hydrogen or optionally substituted $C_1$-$C_3$ alkyl;

X is N or CH; provided that Z is absent;

or a pharmaceutically acceptable salt thereof; or a pharmaceutical composition containing at least one compound of formula (I); for the treatment of conditions and diseases mediated by the adenosine $A_{2A}$ receptor activity.

Listed below are definitions of various terms used to describe the compounds of the present invention. These definitions apply to the terms as they are used throughout the specification unless they are otherwise limited in specific instances either individually or as part of a larger group, e.g., wherein an attachment point of a certain group is limited to a specific atom within that group, the point of attachment is defined by an arrow at the specific atom.

The term "optionally substituted alkyl" refers to unsubstituted or substituted alkyl groups, i.e., straight- or branched-chain hydrocarbon groups having 1-20 carbon atoms, preferably 1-10 carbon atoms, more preferably 1-7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more, preferably 1-3, of the following groups: halo, hydroxy, alkanoyl, alkoxy, cycloalkyl, cycloalkoxy, alkanoyloxy, thiol, alkylthio, alkylthione, sulfinyl, sulfonyl, sulfamoyl, carbamoyl, nitro, cyano, carboxy, alkoxycarbonyl, acyl, aryl, aryloxy, alkenyl, alkynyl, aralkoxy, guanidino, optionally substituted amino, heterocyclyl including imidazolyl, furyl, thienyl, thiazolyl, pyrrolidyl, pyridyl, pyrimidyl and the like.

The term "lower alkyl" refers to those alkyl groups as described above having 1-6, preferably 1-4 carbon atoms.

The term "alkenyl" refers to any of the above alkyl groups having at least two carbon atoms and further containing a carbon-to-carbon double bond at the point of attachment. Groups having 2-4 carbon atoms are preferred.

The term "alkynyl" refers to any of the above alkyl groups having at least two carbon atoms and further containing a carbon-to-carbon triple bond at the point of attachment. Groups having 2-4 carbon atoms are preferred.

The term "alkylene" refers to a straight-chain bridge of 1-6 carbon atoms connected by single bonds, e.g., —(CH$_2$)x-, wherein x is 1-6, and may be interrupted with one to three elements selected from O, S, S(O), S(O)$_2$, CH=CH, C≡C and NR, wherein R may be hydrogen, alkyl, cycloalkyl, aryl, heterocyclyl, acyl, carbamoyl, sulfinyl, sulfonyl, alkoxycarbonyl, aryloxycarbonyl or aralkoxycarbonyl and the like; and the alkylene may further be substituted with one to three substituents selected from optionally substituted alkyl, cycloalkyl, aryl, heterocyclyl, oxo, hydroxy, alkoxy, carboxy, alkoxycarbonyl and the like.

The term "cycloalkyl" refers to optionally substituted monocyclic, bicyclic or tricyclic hydrocarbon groups of 3-12 carbon atoms, each of which may contain one or more carbon to carbon double bonds, or the cycloalkyl may be substituted by one or more substituents, such as alkyl, halo, oxo, hydroxy, alkoxy, alkanoyl, acylamino, carbamoyl, alkylamino, dialkylamino, thiol, alkylthio, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl, cyclohexenyl, 4,4-dimethylcyclohex-1-yl, cyclooctenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

In the definitions listed herein, when a reference to an alkyl, cycloalkyl, alkenyl or alkynyl group is made as part of the term, a substituted alkyl, cycloalkyl, alkenyl or alkynyl group is also intended.

The term "alkoxy" refers to alkyl-O—.
The term "cycloalkoxy" refers to cycloalkyl-O—.
The term "alkanoyl" refers to alkyl-C(O)—.
The term "cycloalkanoyl" refers to cycloalkyl-C(O)—.
The term "alkenoyl" refers to alkenyl-C(O)—.
The term "alkynoyl" refers to alkynyl-C(O)—.
The term "alkanoyloxy" refers to alkyl-C(O)—O—.
The terms "alkylamino" and "dialkylamino" refer to alkyl-NH— and (alkyl)$_2$N—, respectively.
The term "alkanoylamino" refers to alkyl-C(O)—NH—.
The term "alkylthio" refers to alkyl-S—.
The term "alkylthione" refers to alkyl-C(S)—.
The term "trialkylsilyl" refers to (alkyl)$_3$Si—.
The term "trialkylsilyloxy" refers to (alkyl)$_3$SiO—.
The term "alkylthiono" refers to alkyl-S(O)—.
The term "alkylsulfonyl" refers to alkyl-S(O)$_2$—.
The term "alkoxycarbonyl" refers to alkyl-O—C(O)—.
The term "alkoxycarbonyloxy" refers to alkyl-O—C(O)O—.
The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.
The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.
The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.

The term "sulfonyl" refers to alkyl-S(O)$_2$—, aryl-S(O)$_2$—, heteroaryl-S(O)$_2$—, aralkyl-S(O)$_2$—, heteroaralkyl-S(O)$_2$— and the like.

The term "sulfinyl" refers to alkyl-S(O)—, aryl-S(O)—, heteroaryl-S(O)—, aralkyl-S(O)—, heteroaralkyl-S(O)— and the like.

The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.

The term "primary amino group" refers to alkyl-NH—, cycloalkyl-NH—, aryl-NH—, aralkyl-NH—, heteroaryl-NH— and the like.

The term "secondary amino group" refers to (alkyl)$_2$N—, (alkyl)(cycloalkyl)N—, (alkyl)(aryl)N—, (alkyl)(aralkyl)N—, (alkyl)(heteroaryl)N—, (aryl)$_2$N—, (aryl)(aralkyl)N—, (aralkyl)$_2$N— and the like.

The term "aryl" refers to monocyclic or bicyclic aromatic hydrocarbon groups having 6-10 carbon atoms in the ring portion, such as phenyl, naphthyl, tetrahydronaphthyl and indanyl, each of which may optionally be substituted by 1-4 substituents, such as optionally substituted alkyl, trifluoromethyl, optionally substituted cycloalkyl, halo, hydroxy, alkoxy, trifluoromethoxy, methylenedioxy, ethylenedioxy, acyl, alkanoyloxy, aryloxy, optionally substituted amino, thiol, alkylthio, arylthio, nitro, cyano, carboxy, alkoxycarbonyl, carbamoyl, sulfinyl, sulfonyl, sulfamoyl, sulfonamido, heterocyclyl and the like.

The term "monocyclic aryl" refers to optionally substituted phenyl as described above under aryl. Preferably, the monocyclic aryl is substituted by 1-3 substituents selected from the group consisting of halogen, cyano, alkyl, alkoxy, alkylthio, trifluoromethyl, or trifluoromethoxy.

In the definitions listed herein, when a reference to an aryl group is made as part of the term, a substituted aryl group is also intended.

The term "aralkyl" refers to an aryl group bonded directly through an alkyl group, such as benzyl or phenethyl.
The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylsulfinyl" refers to aryl-S(O)—.
The term "arylthio" refers to aryl-S—.
The term "aroyl" refers to aryl-C(O)—.
The term "aroyloxy" refers to aryl-C(O)—O—.
The term "aroylamino" refers to aryl-C(O)—NH—.
The term "aryloxycarbonyl" refers to aryl-O—C(O)—.

The term "heterocyclyl" or "heterocyclo" refers to fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furanyl (furyl), tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl (pyridyl), pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl or furo[2,3-b]pyridinyl), dihydroisoindolyl, 1H-purine-2,6(3H,7H)-dione, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" refers to those heterocyclic groups described above substituted with 1, 2 or 3 substituents selected from the group consisting of the following:

(a) optionally substituted alkyl;
(b) hydroxy (or protected hydroxy);
(c) halo;
(d) oxo, i.e., =O;
(e) optionally substituted amino;
(f) alkoxy;
(g) cycloalkyl;
(h) carboxy;
(i) heterocyclooxy;
(j) alkoxycarbonyl, such as unsubstituted lower alkoxycarbonyl;
(k) thiol;
(l) nitro;
(m) cyano;
(n) sulfamoyl;
(o) alkanoyloxy;
(p) aroyloxy;
(q) arylthio;
(r) aryloxy;
(s) alkylthio;
(t) formyl;
(u) carbamoyl;
(v) aralkyl; and
(w) aryl optionally substituted with alkyl, cycloalkyl, alkoxy, hydroxy, optionally substituted amino, or halo.

The term "heterocyclooxy" denotes a heterocyclic group bonded through an oxygen bridge.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., halogen, hydroxy, cyano, nitro, trifluoromethyl, sulfamoyl, lower alkyl, lower alkoxy, or optionally substituted amino.

The term "heterocycloyl" refers to heterocyclyl-C(O)—.

The term "heteroarylsulfonyl" refers to heteroaryl-S(O)$_2$—.

The term "heteroaroyl" refers to heteroaryl-C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, cycloalkanoyl, alkenoyl, alkynoyl, aroyl, heterocycloyl, heteroaroyl, aralkanoyl, heteroaralkanoyl and the like.

The term acyl includes those acyl groups described above wherein the alkyl, cycloalkyl, alkenyl, alkynyl, aryl, heterocyclyl, heteroaryl, aralkyl, or heteroaralkyl group is substituted as described herein above, respectively.

The term "acylamino" refers to alkanoylamino, aroylamino, heteroaroylamino, aralkanoylamino, heteroaralkanoylamino and the like.

The term "halogen" or "halo" refers to fluorine, chlorine, bromine and iodine.

"Pharmaceutically acceptable salts" of the compounds of the present invention refer to salts formed with acids, namely acid addition salts, such as of mineral acids, organic carboxylic acids and organic sulfonic acids, e.g., hydrochloric acid, maleic acid and methanesulfonic acid, respectively.

Similarly, pharmaceutically acceptable salts of the compounds of the invention refer to salts formed with bases, namely cationic salts, such as alkali and alkaline earth metal salts, e.g., sodium, lithium, potassium, calcium and magnesium, as well as ammonium salts, e.g., ammonium, trimethylammonium, diethylammonium and tris(hydroxymethyl)-methyl-ammonium salts and salts with amino acids provided an acidic group constitutes part of the structure.

As used throughout the specification and in the claims, the term "treatment" embraces all the different forms or modes of treatment as known to those of the pertinent art and in particular includes preventive, curative, delay of progression and palliative treatment.

The term "therapeutically effective amount" as used herein refers to an amount of a drug or a therapeutic agent that will elicit the desired biological or medical response of a tissue, system or an animal (including man) that is being sought by a researcher or clinician.

The term "mammal" or "patient" are used interchangeably herein and include, but are not limited to, humans, dogs, cats, horses, pigs, cows, monkeys, rabbits, mice and laboratory animals. The preferred mammals are humans.

The term "at least one compound of formula (I)" means that one to three different compounds of formula (I) may be used in a pharmaceutical composition or method of treatment thereof. Preferably, one compound of formula (I) is employed.

As described herein above, the present invention provides triazolopyrimidine derivatives of formula (I), pharmaceutical compositions containing them, methods for preparing said compounds, and methods of treating conditions mediated by the adenosine $A_{2A}$ receptor including, but not limited to, diseases of the central nervous system such as depression, cognitive function diseases and neurodegenerative diseases such as Parkinson's disease, senile dementia as in Alzheimer's disease, psychoses and stroke; attention related disorders such as attention deficit disorder (ADD) and attention deficit hyperactivity disorder (ADHD); extra pyramidal syndrome, e.g., dystonia, akathisia, pseudoparkinsonism and tardive dyskinesia; and disorders of abnormal movement such as restless leg syndrome (RLS) and periodic limb movement in sleep (PLMS); cirrhosis, and fibrosis and fatty liver; dermal fibrosis in diseases such as scleroderma; and the mitigation of addictive behavior; by administration of a therapeutically effective amount of a compound of the present invention, or a pharmaceutical composition thereof. In particular, the compounds of the present invention may be employed to improve motor-impairment due to neurodegenerative diseases such as Parkinson's disease.

Preferred are the compounds of formula (I), designated as the A group, wherein $R_1$ is optionally substituted $C_3$-$C_7$ cycloalkyl, optionally substituted $C_6$-$C_{10}$ aryl, optionally substituted heteroaryl or optionally substituted heterocyclyl;

$R_2$ is —$(CR_3R_4)_m$—Y—$(CR_5R_6)_n$—Z-Q in which $R_3$, $R_4$, $R_5$ and $R_6$ are, independently from each other, hydrogen, $C_1$-$C_6$ alkyl or $C_3$-$C_{12}$ cycloalkyl;

m and n are, independently from each other, an integer from 1 to 6;

Y is absent, CH=CH, C≡C, O, S or $NR_7$ in which $R_7$ is hydrogen or $C_1$-$C_4$ alkyl;

Z is absent;

Q is a monovalent radical selected from the group consisting of

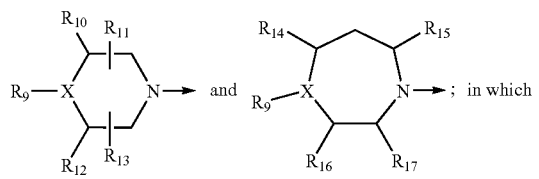

$R_9$ is optionally substituted $C_1$-$C_6$ alkyl, optionally substituted $C_3$-$C_{12}$ cycloalkyl, optionally substituted $C_6$-$C_{10}$ aryl, optionally substituted heteroaryl, optionally substituted aralkyl, optionally substituted heteroaralkyl, heterocyclyl or acyl;

$R_{10}$ and $R_{11}$ are, independently from each other, hydrogen, optionally substituted $C_1$-$C_3$alkyl; or $R_{10}$ and $R_{11}$, provided they are attached to the same carbon atom, combined are alkylene which together with the carbon atom to which they are attached form a 3- to 7-membered spirocyclic ring;

$R_{12}$, $R_{13}$, $R_{14}$, $R_{15}$, $R_{16}$ and $R_{17}$ are, independently from each other, hydrogen or optionally substituted $C_1$-$C_3$ alkyl;

X is N or CH;

or a pharmaceutically acceptable salt thereof.

Preferred are the compounds in the A group, wherein $R_1$ is 5- or 6-membered heteroaryl;

or a pharmaceutically acceptable salt thereof.

More preferred are the compounds in the A group, wherein $R_1$ is 2-furyl;

or a pharmaceutically acceptable salt thereof.

Most preferred are the compounds in the A group, designated as the B group, having the formula

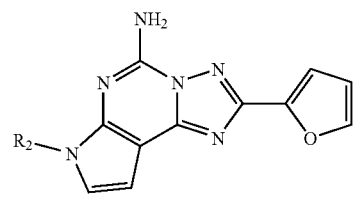

(IA)

wherein $R_2$ is —$(CR_3R_4)_m$—Y—$(CR_5R_6)_n$-Q in which $R_3$, $R_4$, $R_5$ and $R_6$ are, independently from each other, hydrogen or $C_1$-$C_6$ alkyl;

m is an integer of 1 or 2;

n is an integer from 1 to 4;

Y is absent, CH=CH, C≡C or O;

Q is a monovalent radical selected from the group consisting of

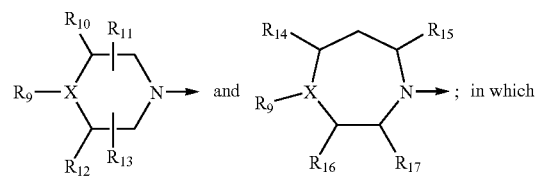

$R_9$ is optionally substituted $C_1$-$C_6$ alkyl, optionally substituted monocyclic aryl, optionally substituted heteroaryl, optionally substituted aralkyl, optionally substituted heteroaralkyl or acyl;

$R_{10}$, $R_{11}$, $R_{12}$, $R_{13}$, $R_{14}$, $R_{15}$, $R_{16}$ and $R_{17}$ are, independently from each other, hydrogen or optionally substituted $C_1$-$C_3$ alkyl;

X is N or CH;

or a pharmaceutically acceptable salt thereof.

Preferred are the compounds in the B group, wherein $R_2$ is —$(CR_3R_4)_m$—Y—$(CR_5R_6)_n$-Q in which $R_3$, $R_4$, $R_5$ and $R_6$ are, independently from each other, hydrogen or $C_1$-$C_3$ alkyl;

m is an integer of 1 or 2;

n is an integer from 1 to 4;

Y is absent;

Q is a monovalent radical of the formula

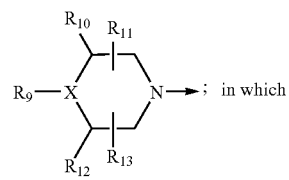

$R_9$ is optionally substituted $C_1$-$C_6$ alkyl, optionally substituted monocyclic aryl, optionally substituted heteroaryl or acyl;

$R_{10}$, $R_{11}$, $R_{12}$ and $R_{13}$ are hydrogen;

X is N;

or a pharmaceutically acceptable salt thereof.

Further preferred are the compounds in the B group having the formula

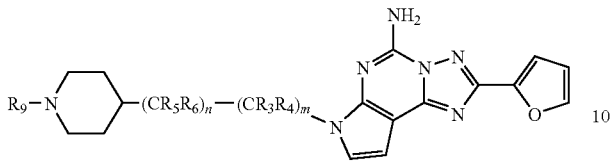

(IB)

wherein
R_3, R_4, R_5 and R_6 are hydrogen
m and n are 1;
R_9 is optionally substituted $C_1$-$C_6$ alkyl, optionally substituted monocyclic aryl, optionally substituted heteroaryl or acyl;

or a pharmaceutically acceptable salt thereof.
Preferred are the compounds of formula (IB), wherein
R_9 is monocyclic aryl optionally substituted by 1 to 3 halogens;

or a pharmaceutically acceptable salt thereof.
Preferred are also the compounds of formula (IB), wherein
R_9 is monocyclic aroyl optionally substituted by 1 to 3 halogens;

or a pharmaceutically acceptable salt thereof.
Preferred are also the compounds of formula (IB), designated as the C group, wherein
R_9 is $C_1$-$C_6$ alkyl substituted with acyl;

or a pharmaceutically acceptable salt thereof.
Preferred are the compounds in the C group, wherein
acyl is optionally substituted monocyclic aroyl or optionally substituted monocyclic heteroaroyl;

or a pharmaceutically acceptable salt thereof.
Further preferred are the compounds in the C group, wherein
acyl is monocyclic aroyl optionally substituted by 1 to 3 halogens;

or a pharmaceutically acceptable salt thereof.
Preferred are also the compound of formula (I), designated as the D group, wherein
R_1 is optionally substituted $C_3$-$C_7$ cycloalkyl, optionally substituted $C_6$-$C_{10}$ aryl, optionally substituted heteroaryl or optionally substituted heterocyclyl;
R_2 is —(CR_3R_4)_m—Y—(CR_5R_6)_n—Z-Q in which
R_3, R_4, R_5 and R_6 are, independently from each other, hydrogen, $C_1$-$C_6$ alkyl or $C_3$-$C_{12}$ cycloalkyl;
m and n are, independently from each other, an integer from 1 to 6;
Y is absent, CH=CH, C≡C, O, S, NR_7 in which R_7 is hydrogen or $C_1$-$C_4$ alkyl;
Z is absent, O, S or NR_8 in which R_8 is hydrogen or $C_1$-$C_4$ alkyl;
Q is optionally substituted $C_6$-$C_{10}$ aryl or optionally substituted heteroaryl;

or a pharmaceutically acceptable salt thereof.
Preferred are the compounds in the D group, wherein
R_1 is 5- or 6-membered heteroaryl;

or a pharmaceutically acceptable salt thereof.

More preferred are the compounds in the D group wherein
R_1 is 2-furyl;

or a pharmaceutically acceptable salt thereof.
Most preferred are the compounds in the D group, designated as the E group, having the formula

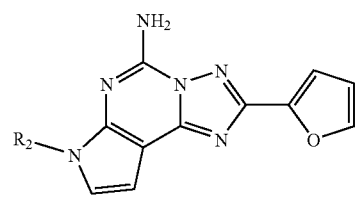

(IA)

wherein
R_2 is —(CR_3R_4)_m—Y—(CR_5R_6)_n—Z-Q in which
R_3, R_4, R_5 and R_6 are, independently from each other, hydrogen or $C_1$-$C_6$ alkyl;
m is an integer of 1 or 2;
n is an integer from 1 to 4;
Y is absent or NR_7 in which R_7 is hydrogen or $C_1$-$C_4$ alkyl;
Z is absent, O, S or NR_8 in which R_8 is hydrogen or $C_1$-$C_4$ alkyl;
Q is optionally substituted monocyclic aryl;

or a pharmaceutically acceptable salt thereof.
Preferred are the compounds in the E group having the formula

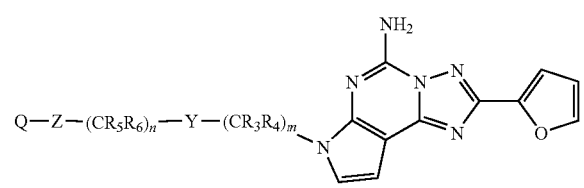

(IC)

wherein
R_3, R_4, R_5 and R_6 are hydrogen;
m is 2;
n is an integer from 2 to 4;
Y is NR_7 in which R_7 is hydrogen or $C_1$-$C_4$ alkyl;
Z is NR_8 in which R_8 is hydrogen or $C_1$-$C_4$ alkyl;
Q is optionally substituted monocyclic aryl;

or a pharmaceutically acceptable salt thereof.
Preferred are also the compounds in the E group having formula (IC), wherein
R_3, R_4, R_5 and R_6 are hydrogen;
m is 1;
n is an integer from 1 to 4;
Y is absent;
Z is O, S or NR_8 in which R_8 is hydrogen or $C_1$-$C_4$ alkyl;
Q is optionally substituted monocyclic aryl;

or a pharmaceutically acceptable salt thereof.
Preferred are compounds of formula (IC), wherein
Q is monocyclic aryl optionally substituted by 1 to 3 halogens;

or a pharmaceutically acceptable salt thereof.

The compounds of the invention depending on the nature of the substituents may possess one or more asymmetric centers. The resulting diastereoisomers, optical isomers, i.e., enantiomers, and geometric isomers, and mixtures thereof, are encompassed by the instant invention.

Particular embodiments of the invention are:

7-(2-(4-(2,5-Difluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,4-Difluorobenzyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-((3-methylbenzo[b]thiophen-2-yl)methyl)piperazin-1-yl)ethyl)-7H-pyrrolo[3,2-e][1,2,4]triazolo[1,5-c]pyrimidin-5-amine;

7-(2-(4-(2,4-Difluorophenethyl)piperazin-1-yl)ethyl)-2-(furan-2-yl)-7H-pyrrolo[3,2-e][1,2,4]triazolo[1,5-c]pyrimidin-5-amine;

7-(2-(4-(3-(2,4-Difluorophenyl)propyl)piperazin-1-yl)ethyl)-2-(furan-2-yl)-7H-pyrrolo[3,2-e][1,2,4]triazolo[1,5-c]pyrimidin-5-amine;

(4-(2-(5-Amino-2-(furan-2-yl)-7H-pyrrolo[3,2-e][1,2,4]triazolo[1,5-c]pyrimidin-7-yl)ethyl)piperazin-1-yl)(2,4-difluorophenyl)methanone;

1-(4-(2-(5-Amino-2-(furan-2-yl)-7H-pyrrolo[3,2-e][1,2,4]triazolo[1,5-c]pyrimidin-7-yl)ethyl)piperazin-1-yl)-2-(2,4-difluorophenyl)ethanone;

1-(4-(2-(5-Amino-2-(furan-2-yl)-7H-pyrrolo[3,2-e][1,2,4]triazolo[1,5-c]pyrimidin-7-yl)ethyl)piperazin-1-yl)-3-(2,4-difluorophenyl)propan-1-one;

7-(2-(4-(2,4-Difluorophenyl)-1,4-diazepan-1-yl)ethyl)-2-(furan-2-yl)-7H-pyrrolo[3,2-e][1,2,4]triazolo[1,5-c]pyrimidin-5-amine;

7-(2-(4-(2,4-Difluorophenyl)piperidin-1-yl)ethyl)-2-(furan-2-yl)-7H-pyrrolo[3,2-e][1,2,4]triazolo[1,5-c]pyrimidin-5-amine;

7-(2-(2,4-Difluorophenoxy)ethyl)-2-(furan-2-yl)-7H-pyrrolo[3,2-e][1,2,4]triazolo[1,5-c]pyrimidin-5-amine;

7-(2-(2,4-Difluorophenylthio)ethyl)-2-(furan-2-yl)-7H-pyrrolo-[3,2-e][1,2,4]triazolo[1,5-c]pyrimidin-5-amine;

7-(2-(2,4-Difluorophenylamino)ethyl)-2-(furan-2-yl)-7H-pyrrolo[3,2-e][1,2,4]triazolo[1,5-c]pyrimidin-5-amine;

7-(2-(4-(2,4-Difluorophenyl)piperazin-1-yl)propyl)-2-(furan-2-yl)-7H-pyrrolo[3,2-e][1,2,4]triazolo[1,5-c]pyrimidin-5-amine;

7-(3-(4-(2,4-Difluorophenyl)piperazin-1-yl)butyl)-2-(furan-2-yl)-7H-pyrrolo[3,2-e][1,2,4]triazolo[1,5-c]pyrimidin-5-amine;

2-(Furan-2-yl)-7-(2-(4-methylpiperazin-1-yl)ethyl)-7H-pyrrolo[3,2-e][1,2,4]triazolo[1,5-c]pyrimidin-5-amine;

2-(Furan-2-yl)-7-(2-(4-isopropylpiperazin-1-yl)ethyl)-7H-pyrrolo[3,2-e][1,2,4]triazolo[1,5-c]pyrimidin-5-amine;

7-(2-(4-Cyclopentylpiperazin-1-yl)ethyl)-2-(furan-2-yl)-7H-pyrrolo[3,2-e][1,2,4]triazolo[1,5-c]pyrimidin-5-amine;

7-(2-(4-Cyclohexylpiperazin-1-yl)ethyl)-2-(furan-2-yl)-7H-pyrrolo[3,2-e][1,2,4]-triazolo[1,5-c]pyrimidin-5-amine;

7-(2-(4-Cycloheptylpiperazin-1-yl)ethyl)-2-(furan-2-yl)-7H-pyrrolo[3,2-e][1,2,4]triazolo[1,5-c]pyrimidin-5-amine;

7-(2-(4-Cyclooctylpiperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-phenylpiperazin-1-yl)ethyl)-7H-pyrrolo[3,2-e][1,2,4]triazolo[1,5-c]pyrimidin-5-amine;

7-(2-(4-(2-Fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(3-Fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(4-Fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,3-Difluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,6-Difluorophenyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-(2,4,6-trifluorophenyl)piperazin-1-yl)ethyl)-7H-pyrrolo[3,2-e][1,2,4]triazolo[1,5-c]pyrimidin-5-amine;

7-(2-(4-(4-Chlorophenyl)piperazin-1-yl)ethyl)-2-(furan-2-yl)-7H-pyrrolo[3,2-e][1,2,4]triazolo[1,5-c]pyrimidin-5-amine;

7-(2-(4-(3,4-Dichlorophenyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-p-tolylpiperazin-1-yl)ethyl)-7H-pyrrolo[3,2-e][1,2,4]triazolo[1,5-c]pyrimidin-5-amine;

2-(Furan-2-yl)-7-(2-(4-(4-methoxyphenyl)piperazin-1-yl)ethyl)-7H-pyrrolo[3,2-e][1,2,4]triazolo[1,5-c]pyrimidin-5-amine;

7-(2-(4-(4-Chloro-2-fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2-Chloro-4-fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(4-Bromo-2-fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2-Bromo-4-fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,4-Dichlorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,4-Dimethylphenyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-(3-methoxy-5-(trifluoromethyl)phenyl)piperazin-1-yl)ethyl)-7H-pyrrolo[3,2-e][1,2,4]triazolo[1,5-c]pyrimidin-5-amine;

7-(2-(4-(3,5-Bis(trifluoromethyl)phenyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-(4-nitrophenyl)piperazin-1-yl)ethyl)-7H-pyrrolo[3,2-e][1,2,4]triazolo[1,5-c]pyrimidin-5-amine;

2-(Furan-2-yl)-7-(2-(4-(4-(trifluoromethyl)phenyl)piperazin-1-yl)ethyl)-7H-pyrrolo[3,2-e][1,2,4]triazolo[1,5-c]pyrimidin-5-amine;

2-(Furan-2-yl)-7-(2-(4-(2-(trifluoromethyl)phenyl)piperazin-1-yl)ethyl)-7H-pyrrolo[3,2-e][1,2,4]triazolo[1,5-c]pyrimidin-5-amine;

2-(Furan-2-yl)-7-(2-(4-(4-isopropylphenyl)piperazin-1-yl)ethyl)-7H-pyrrolo[3,2-e][1,2,4]triazolo[1,5-c]pyrimidin-5-amine;

7-(2-(4-(4-Butylphenyl)piperazin-1-yl)ethyl)-2-(furan-2-yl)-7H-pyrrolo[3,2-e][1,2,4]triazolo[1,5-c]pyrimidin-5-amine;

7-(2-(4-(4-t-Butylphenyl)piperazin-1-yl)ethyl)-2-(furan-2-yl)-7H-pyrrolo[3,2-e][1,2,4]triazolo[1,5-c]pyrimidin-5-amine;

7-(2-(4-(3,4-Dimethoxyphenyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-(2-(methylthio)phenyl)piperazin-1-yl)ethyl)-7H-pyrrolo[3,2-e][1,2,4]triazolo[1,5-c]pyrimidin-5-amine;

2-(Furan-2-yl)-7-(2-(4-(3-(methylthio)phenyl)piperazin-1-yl)ethyl)-7H-pyrrolo[3,2-e][1,2,4]triazolo[1,5-c]pyrimidin-5-amine;

2-(Furan-2-yl)-7-(2-(4-(4-(trifluoromethoxy)phenyl)piperazin-1-yl)ethyl)-7H-pyrrolo[3,2-e][1,2,4]triazolo[1,5-c]pyrimidin-5-amine;

2-(Furan-2-yl)-7-(2-(4-(pyridin-2-yl)piperazin-1-yl)ethyl)-7H-pyrrolo[3,2-e][1,2,4]triazolo[1,5-c]pyrimidin-5-amine;

2-(furan-2-yl)-7-(2-(4-(pyridin-3-yl)piperazin-1-yl)ethyl)-7H-pyrrolo[3,2-e][1,2,4]triazolo[1,5-c]pyrimidin-5-amine;

2-(Furan-2-yl)-7-(2-(4-(pyridin-4-yl)piperazin-1-yl)ethyl)-7H-pyrrolo[3,2-e][1,2,4]triazolo[1,5-c]pyrimidin-5-amine;

7-(2-(4-(Benzo[d]isothiazol-3-yl)piperazin-1-yl)ethyl)-2-(furan-2-yl)-7H-pyrrolo[3,2-e][1,2,4]-triazolo[1,5-c]pyrimidin-5-amine;

7-(2-(4-(3-Chloro-5-(trifluoromethyl)pyridin-2-yl)piperazin-1-yl)ethyl)-2-(furan-2-yl)-7H-pyrrolo[3,2-e][1,2,4]triazolo[1,5-c]pyrimidin-5-amine;

Methyl 5-(4-(2-(5-amino-2-(furan-2-yl)-7H-pyrrolo[3,2-e][1,2,4]triazolo[1,5-c]pyrimidin-7-yl)ethyl)piperazin-1-yl)-7-(trifluoromethyl)thieno[3,2-b]pyridine-3-carboxylate;

7-(2-(4-(1H-Indol-4-yl)piperazin-1-yl)ethyl)-2-(furan-2-yl)-7H-pyrrolo[3,2-e][1,2,4]triazolo[1,5-c]pyrimidin-5-amine;

5-(4-(2-(5-Amino-2-(furan-2-yl)-7H-pyrrolo[3,2-e][1,2,4]triazolo[1,5-c]pyrimidin-7-yl)ethyl)piperazin-1-yl)-4-nitrothiophene-2-sulfonamide;

7-(2-(4-(Benzo[d][1,3]dioxol-5-ylmethyl)piperazin-1-yl)ethyl)-2-(furan-2-yl)-7H-pyrrolo[3,2-e][1,2,4]triazolo[1,5-c]pyrimidin-5-amine;

7-(2-(4-((3,5-Dimethyl-1-phenyl-1H-pyrazol-4-yl)methyl)piperazin-1-yl)ethyl)-2-(furan-2-yl)-7H-pyrrolo[3,2-e][1,2,4]triazolo[1,5-c]pyrimidin-5-amine;

5-((4-(2-(5-Amino-2-(furan-2-yl)-7H-pyrrolo[3,2-e][1,2,4]triazolo[1,5-c]pyrimidin-7-yl)ethyl)piperazin-1-yl)methyl)-1,3-dimethylpyrimidine-2,4(1H,3H)-dione;

2-(Furan-2-yl)-7-(2-(4-(2-methoxyphenyl)piperazin-1-yl)ethyl)-7H-pyrrolo[3,2-e][1,2,4]triazolo[1,5-c]pyrimidin-5-amine;

7-(2-(4-Fluorophenoxy)ethyl)-2-(furan-2-yl)-7H-pyrrolo[3,2-e][1,2,4]triazolo[1,5-c]pyrimidin-5-amine;

7-(3-(4-(2,4-Difluorophenyl)piperazin-1-yl)propyl)-2-(furan-2-yl)-7H-pyrrolo[3,2-e][1,2,4]triazolo[1,5-c]pyrimidin-5-amine;

7-(1-(4-(2,4-Difluorophenyl)piperazin-1-yl)propan-2-yl)-2-(furan-2-yl)-7H-pyrrolo[3,2-e][1,2,4]triazolo[1,5-c]pyrimidin-5-amine;

7-(4-(4-(2,4-Difluorophenyl)piperazin-1-yl)but-2-ynyl)-2-(furan-2-yl)-7H-pyrrolo[3,2-e][1,2,4]triazolo[1,5-c]pyrimidin-5-amine;

7-(4-(4-(2,4-Difluorophenyl)piperazin-1-yl)butan-2-yl)-2-(furan-2-yl)-7H-pyrrolo[3,2-e][1,2,4]triazolo[1,5-c]pyrimidin-5-amine;

7-(3-(4-(2,4-Difluorophenyl)piperazin-1-yl)-2-methylpropyl)-2-(furan-2-yl)-7H-pyrrolo[3,2-e][1,2,4]triazolo[1,5-c]pyrimidin-5-amine;

$N^1$-(2-(5-Amino-2-(furan-2-yl)-7H-pyrrolo[3,2-e][1,2,4]triazolo[1,5-c]pyrimidin-7-yl)ethyl)-$N^4$-(2,4-difluorophenyl)butane-1,4-diamine;

$N^1$-(2-(5-Amino-2-(furan-2-yl)-7H-pyrrolo[3,2-e][1,2,4]triazolo[1,5-c]pyrimidin-7-yl)ethyl)-$N^2$-(2,4-difluorophenyl)-$N^2$-ethylethane-1,2-diamine;

$N^1$-(2-(5-Amino-2-(furan-2-yl)-7H-pyrrolo[3,2-e][1,2,4]triazolo[1,5-c]pyrimidin-7-yl)ethyl)-$N^2$-(2,4-difluorophenyl)-$N^1$-ethylethane-1,2-diamine;

$N^1$-(2-(5-Amino-2-(furan-2-yl)-7H-pyrrolo[3,2-e][1,2,4]triazolo[1,5-c]pyrimidin-7-yl)ethyl)-$N^3$-(2,4-difluorophenyl)-$N^1$-methylpropane-1,3-diamine;

$N^1$-(2-(5-Amino-2-(furan-2-yl)-7H-pyrrolo[3,2-e][1,2,4]triazolo[1,5-c]pyrimidin-7-yl)ethyl)-$N^4$-(2,4-difluorophenyl)-$N^1$-methyl butane-1,4-diamine;

$N^1$-(2-(5-Amino-2-(furan-2-yl)-7H-pyrrolo[3,2-e][1,2,4]triazolo[1,5-c]pyrimidin-7-yl)ethyl)-$N^2$-(2,4-difluorophenyl)-$N^1,N^2$-dimethylethane-1,2-diamine;

7-(2-(4-(2,4-Difluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,4-Difluorophenyl)piperazin-1-yl)ethyl)-2-phenyl-7H-pyrrolo[3,2-e][1,2,4]triazolo[1,5-c]pyrimidin-5-amine;

7-(4-(4-(2,4-Difluorophenyl)piperazin-1-yl)butyl)-2-(furan-2-yl)-7H-pyrrolo[3,2-e][1,2,4]triazolo[1,5-c]pyrimidin-5-amine;

7-(5-(4-(2,4-Difluorophenyl)piperazin-1-yl)pentyl)-2-(furan-2-yl)-7H-pyrrolo[3,2-e][1,2,4]triazolo[1,5-c]pyrimidin-5-amine;

7-(2-(2-(4-(2,4-Difluorophenyl)piperazin-1-yl)ethoxy)ethyl)-2-(furan-2-yl)-7H-pyrrolo[3,2-e][1,2,4]triazolo[1,5-c]pyrimidin-5-amine;

(E)-7-(4-(4-(2,4-Difluorophenyl)piperazin-1-yl)but-2-enyl)-2-(furan-2-yl)-7H-pyrrolo[3,2-e][1,2,4]triazolo[1,5-c]pyrimidin-5-amine;

(Z)-7-(4-(4-(2,4-Difluorophenyl)piperazin-1-yl)but-2-enyl)-2-(furan-2-yl)-7H-pyrrolo[3,2-e][1,2,4]triazolo[1,5-c]pyrimidin-5-amine;

7-(2-(4-(2,4-Difluorophenyl)piperazin-1-yl)ethyl)-2-(thiophen-2-yl)-7H-pyrrolo[3,2-e][1,2,4]triazolo[1,5-c]pyrimidin-5-amine;

7-(2-(4-(2,4-Difluorophenyl)piperazin-1-yl)ethyl)-2-(tetrahydrofuran-2-yl)-7H-pyrrolo[3,2-e][1,2,4]triazolo[1,5-c]pyrimidin-5-amine;

2-(Benzofuran-2-yl)-7-(2-(4-(2,4-difluorophenyl)piperazin-1-yl)ethyl)-7H-pyrrolo[3,2-e][1,2,4]triazolo[1,5-c]pyrimidin-5-amine;

7-(2-(4-(2,4-Difluorophenyl)piperazin-1-yl)ethyl)-2-(pyridin-2-yl)-7H-pyrrolo[3,2-e][1,2,4]triazolo[1,5-c]pyrimidin-5-amine;

7-(2-(4-(2,4-Difluorophenyl)piperazin-1-yl)ethyl)-2-(pyridin-3-yl)-7H-pyrrolo[3,2-e][1,2,4]triazolo[1,5-c]pyrimidin-5-amine;

2-(5-Amino-7-(2-(4-(2,4-difluorophenyl)piperazin-1-yl)ethyl)-7H-pyrrolo[3,2-e][1,2,4]triazolo[1,5-c]pyrimidin-2-yl)phenol; and 7-(2-(4-(2,4-Difluorophenyl)piperazin-1-yl)ethyl)-2-(furan-3-yl)-7H-pyrrolo[3,2-e][1,2,4]triazolo[1,5-c]pyrimidin-5-amine;

or a pharmaceutically acceptable salt thereof.

Compounds of formula (I) may be prepared using methods well known in the art, or using modifications thereof, e.g., as outlined herein in Schemes 1 to 4.

As exemplified in Scheme 1, compounds of formula (I), wherein $R_1$ and $R_2$ have meaning as defined herein above, may be prepared starting from 2,6-diaminopyrimidin-4(3H)-one of formula (1).

Scheme 1:

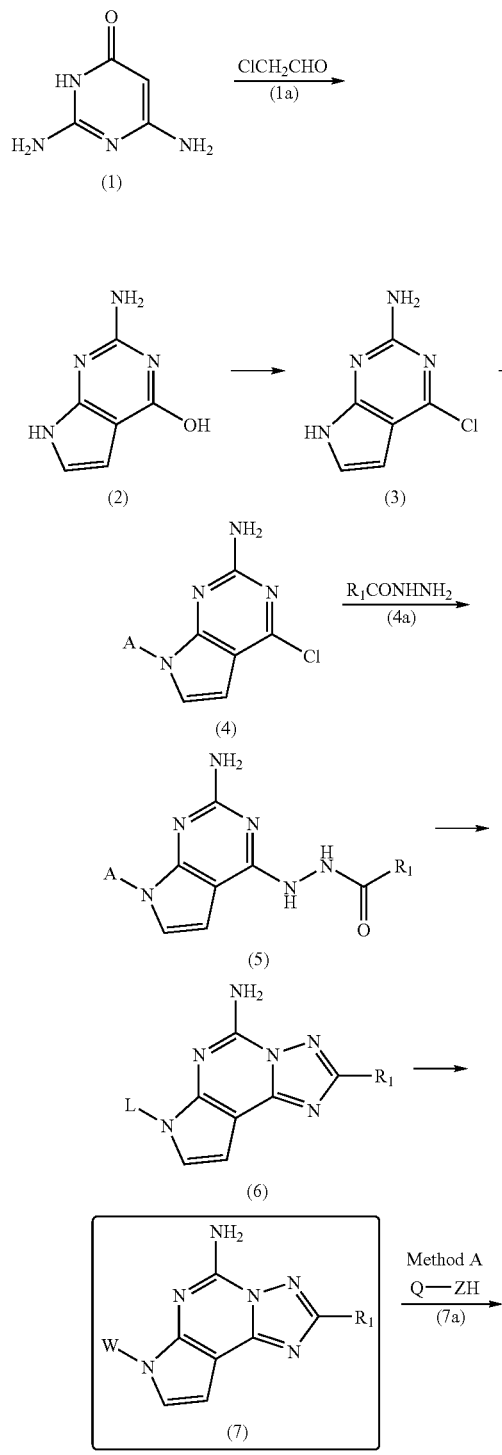

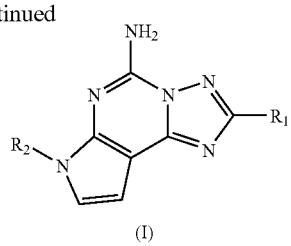

$A = \text{—}(CR_3R_4)_m\text{—}Y\text{—}(CR_5R_6)_n\text{—}OPg$ $L = \text{—}(CR_3R_4)_m\text{—}Y\text{—}(CR_5R_6)_n\text{—}OH$ $W = \text{—}(CR_3R_4)_m\text{—}Y\text{—}(CR_5R_6)_n\text{-Lg}$ $R_2 = \text{—}(CR_3R_4)_m\text{—}Y\text{—}(CR_5R_6)_n\text{—}Z\text{—}Q$ 2,6-Diaminopyrimidin-4(3H)-one of formula (1) may first be converted to 4-chloro-7H-pyrrolo[2,3-d]pyrimidin-2-amine of formula (3) using known methods, e.g., those described by Shih et al. in *Heterocycles* 35 (2), 825-841, 1993; and by Akimoto et al. in *J. Med. Chem.* 29, 1749-1753, 1986. As outlined in Scheme 1, designated herein as Method A, the resulting 4-chloro-7H-pyrrolo[2,3-d]pyrimidin-2-amine of formula (3) may then be treated with an alkylating agent of formula (3a), wherein Lg' represents a leaving group such as chloride, bromide, iodide, mesylate or tosylate, and A represents —$(CR_3R_4)_m$—Y—$(CR_5R_6)_n$—OPg in which $R_3$, $R_4$, $R_5$, $R_6$, Y, m and n have meaning as defined herein above, and Pg is a suitable hydroxyl protecting group such as a trialkylsilyl group, e.g., t-butyldimethylsilyl group, to afford a compound of formula (4), wherein A has a meaning as described herein above. Preferably, the alkylation step is carried out in the presence of a base such as sodium hydride, and an organic solvent such as N,N-dimethylformamide (DMF). Preferably, the alkylation is conducted at a temperature ranging from about 0° C. to room temperature (RT).

Compounds of formula (3a), wherein Lg' and A have meaning as defined herein above, are known, or if they are novel they may be prepared using methods well known in the art, or modifications thereof, or as described herein in the illustrative Examples.

A resulting compound of formula (4), wherein A has meaning as defined herein above, may then be converted to compounds of formula (5), wherein A and $R_1$ have meaning as defined herein above, by condensing with a hydrazide of formula (4a), wherein $R_1$ has meaning as defined herein above. Preferably, the reaction is carried out in an organic solvent such as N-methylpyrrolidinone (NMP) or a lower alcohol, e.g., n-butanol (n-BuOH), at a temperature near to the boiling point of the solvent.

Compounds of formula (4a), wherein $R_1$ has meaning as defined herein above, are known, or if they are novel they may be prepared using methods well known in the art, or modifications thereof, or as described herein in the illustrative Examples.

A subsequent cyclization of a compound of formula (5), wherein A and $R_1$ have meaning as defined herein above, in the presence of a base such as hexamethyldisilazide (HMDS) and a silylating agent such as N,O-bis(trimethylsilyl)acetamide (BSA) at a temperature of about 120° C., followed by removal of the hydroxyl protecting group, e.g., by treatment with an acid such aqueous hydrochloric acid (HCl) in an organic solvent such as a lower alcohol, e.g., methanol (MeOH) or ethanol (EtOH), at a temperature ranging from about 0° C. to RT, then affords a compound of formula (6), wherein $R_1$ has a meaning as defined herein above, and L represents —(CR$_3$R$_4$)$_m$—Y—(CR$_5$R$_6$)$_n$—OH in which R$_3$, R$_4$, R$_5$, R$_6$, Y, m and n have meaning as defined herein above.

A resulting compound of formula (6), wherein L and R$_1$ have meaning as defined herein above, may then be converted to a compound of formula (7), wherein R$_1$ has meaning as defined herein above, and W represents —(CR$_3$R$_4$)$_m$—Y—(CR$_5$R$_6$)$_n$-Lg in which R$_3$, R$_4$, R$_5$, R$_6$, Y, m and n have meaning as defined herein above, and Lg represents a leaving group such as chloride, bromide, iodide, mesylate or tosylate, using methods well known in the art. For example, a compound of formula (6), wherein L and R$_1$ have meaning as defined herein above, may be treated with methanesulfonyl chloride in the presence of a base such as triethylamine (TEA) or pyridine, or a mixture of bases thereof, and an organic solvent such as tetrahydrofuran (THF), to afford a compound of formula (7), wherein R$_1$, R$_3$, R$_4$, R$_5$, R$_6$, Y, m and n have meaning as defined herein above, and Lg is a methanesulfonate group. Preferably, the reaction is carried out at a temperature of about 0° C.

Compounds of formula (7a), wherein Q and Z have meaning as defined herein above, are known, or if they are novel they may be prepared using methods well known in the art, or modifications thereof, or as described herein in the illustrative Examples.

As outlined in Scheme 2, compounds of formula (7), wherein R$_1$ and W have meaning as defined herein above, may also be obtained by two alternative routes utilizing a common intermediate of formula (9), wherein R$_1$ has meaning as defined herein above.

Accordingly, compounds of formula (9), wherein R$_1$ has meaning as defined herein above, may be prepared by condensing 4-chloro-7H-pyrrolo[2,3-d]pyrimidin-2-amine of formula (3) with a hydrazide of formula (4a), wherein R$_1$ has meaning as defined herein above, to afford a compound of formula (8), wherein R$_1$ has meaning as defined herein above. Preferably, the condensation is carried out in an organic solvent such as NMP or a lower alcohol, e.g., n-BuOH, at a temperature near to the boiling point of the solvent.

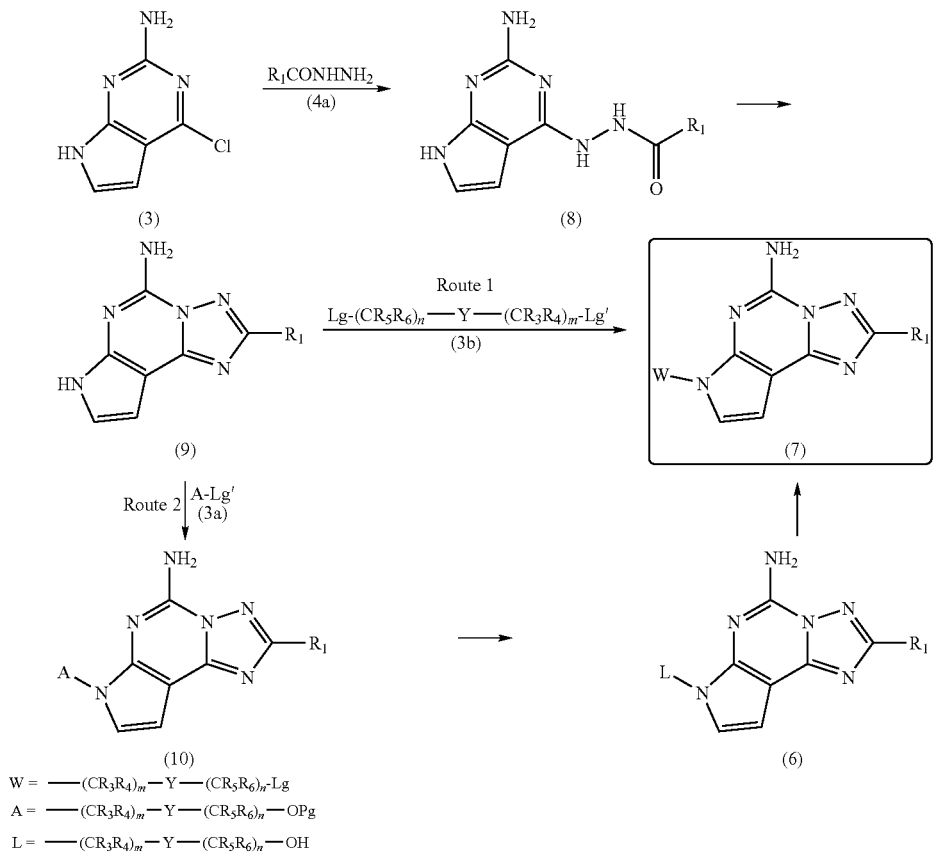

Finally, a resulting compound of formula (7), wherein R$_1$ and W have meaning as defined herein above, may be treated with a compound of formula (7a), wherein Q and Z have meaning as defined herein above, in the presence of a base such as TEA or diisopropylethylamine (DIEA), and an organic solvent such as DMF, e.g., at a temperature of about 100° C., to afford a compound of formula (I), wherein R$_1$ and R$_2$ have meaning as defined herein above.

A resulting compound of formula (8), wherein R$_1$ has meaning as defined herein above, may then be cyclized to afford a compound of formula (9), wherein R$_1$ has meaning as defined herein above, in the presence of a base such as HMDS and a silylating agent such as BSA at a temperature of about 120° C.

According to Route 1, compounds of formula (7), wherein R$_1$ and W have meaning as defined herein above, may be obtained by treating a compound of formula (9), wherein R$_1$ has meaning as defined herein above, with an alkylating agent of formula (3b), wherein $R_3$, $R_4$, $R_5$, $R_6$, Y, m and n have meaning as defined herein above, and Lg and Lg' represents the same or a different leaving group such as chloride, bromide, iodide, mesylate or tosylate, in the presence of a base such as sodium hydride, and an organic solvent such as DMF. Preferably, the alkylation is conducted at a temperature ranging from about 0° C. to room temperature (RT).

Compounds of formula (3b), wherein $R_3$, $R_4$, $R_5$, $R_6$, Y, m, n, Lg and Lg' have meaning as defined herein above, are known, or if they are novel they may be prepared using methods well known in the art, or modifications thereof, or as described herein in the illustrative Examples.

According to Route 2, a compound of formula (9), wherein $R_1$ has meaning as defined herein above, may first be converted to a compound of formula (10), wherein $R_1$ and A have meaning as defined herein above, by treatment with an alkylating agent of formula (3a), wherein A and Lg' have meaning as defined herein above. Preferably, the alkylation step is carried out in the presence of a base such as sodium hydride, and an organic solvent such as DMF, at a temperature ranging from about 0° C. to room temperature (RT).

A resulting compound of formula (10), wherein $R_1$ and A have meaning as defined herein above, may then be converted to a compound of formula (6), wherein $R_1$ and L have meaning as defined herein above, by removal of the protecting group (Pg) under conditions well known in the art. For example, a compound of formula (10), wherein $R_1$ has meaning as defined herein above, and Pg represents a trialkylsilyl group, e.g., t-butyldimethylsilyl group, may be treated with a fluoride reagent, such as tetra-n-butylammonium fluoride, in an organic solvent such as THF to afford a compound of formula (6), wherein $R_1$ and L have meaning as defined herein above. Preferably, the desilylation step is conducted at RT.

Finally, a resulting compound of formula (6), wherein $R_1$ and L have meaning as defined herein above, may be converted to a compound of formula (7), wherein $R_1$ and W have meaning as defined herein above, as described herein above in Scheme 1.

Alternatively, as illustrated in Scheme 3 and designated herein as Method B, compounds of formula (I), wherein $R_1$ and $R_2$ have meaning as defined herein above, may be prepared by treating a compound of formula (9), wherein $R_1$ has meaning as defined herein above, with an alkylating agent of formula (3d), wherein $R_3$, $R_4$, $R_5$, $R_6$, Y, Z, Q, m and n have meaning as defined herein above, and Lg' represents a leaving group such as chloride, bromide, iodide, mesylate or tosylate, in the presence of a base such as sodium hydride, and an organic solvent such as DMF. Preferably, the alkylation is conducted at a temperature ranging from about 0° C. to room temperature (RT).

Scheme 3:

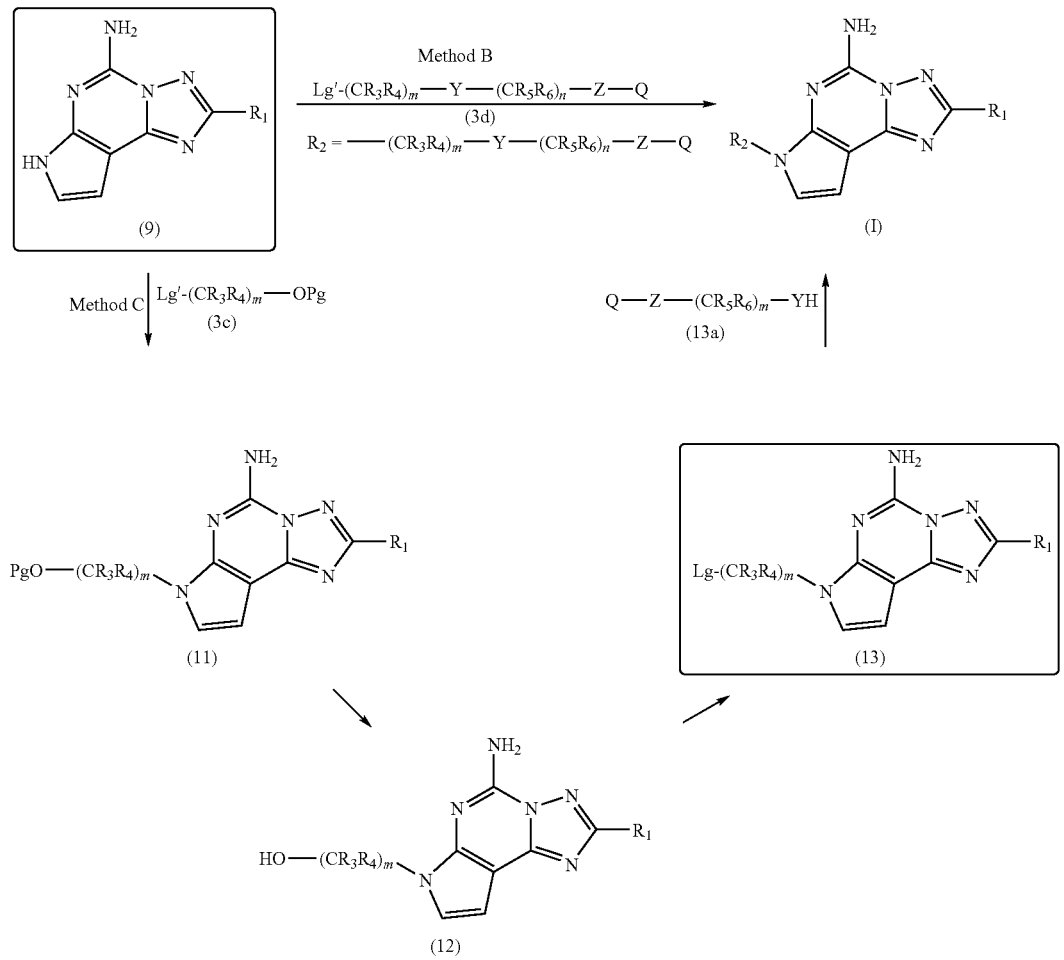

Compounds of formula (3d), wherein $R_3$, $R_4$, $R_5$, $R_6$, Y, Z, Q, m, n and Lg have meaning as defined herein above, are known, or if they are novel they may be prepared using methods well known in the art, or modifications thereof, or as described herein in the illustrative Examples.

As outlined in Scheme 3 and designated herein as Method C, compounds of formula (I), wherein $R_1$ and $R_2$ have meaning as defined herein above, may also be prepared by treating a compound of formula (9), wherein $R_1$ has meaning as defined herein above, with an alkylating agent of formula (3c), wherein $R_3$, $R_4$ and m have meaning as defined herein above, Lg' represents a leaving group such as chloride, bromide, iodide, mesylate or tosylate, and Pg is a suitable hydroxyl protecting group such as a trialkylsilyl group, e.g., t-butyldimethylsilyl group, to afford a compound of formula (II), wherein $R_3$, $R_4$, m and Pg have meaning as defined herein above. Preferably, the alkylation step is carried out in the presence of a base such as sodium hydride, and an organic solvent such as DMF. Preferably, the alkylation is conducted at a temperature ranging from about 0° C. to RT.

Compounds of formula (3c), wherein $R_3$, $R_4$, m, Lg' and Pg have meaning as defined herein above, are known, or if they are novel they may be prepared using methods well known in the art, or modifications thereof, or as described herein in the illustrative Examples.

A resulting compound of formula (II), wherein $R_1$, $R_3$, $R_4$, m and Pg have meaning as defined herein above, may then be converted to a compound of formula (12), wherein $R_1$, $R_3$, $R_4$ and m have meaning as defined herein above, by removal of the protecting group (Pg) under conditions well known in the art. For example, a compound of formula (II), wherein $R_1$, $R_3$, $R_4$ and m have meaning as defined herein above, and Pg represents a trialkylsilyl group, e.g., t-butyldimethylsilyl group, may be treated with a fluoride reagent, such as tetra-n-butylammonium fluoride, in an organic solvent such as THF to afford a compound of formula (12), wherein $R_1$, $R_3$, $R_4$ and m have meaning as defined herein above. Preferably, the desilylation step is conducted at RT.

A resulting compound of formula (12), wherein $R_1$, $R_3$, $R_4$ and m have meaning as defined herein above, may then be converted to a compound of formula (13), wherein $R_1$, $R_3$, $R_4$ and m have meaning as defined herein above, and Lg represents a leaving group such as chloride, bromide, iodide, mesylate or tosylate, as described herein above in Scheme 1.

Finally, a resulting compound of formula (13), wherein $R_1$, $R_3$, $R_4$, m and Lg have meaning as defined herein above, may be converted to a compound of formula (I), wherein $R_1$ and $R_2$ have meaning as defined herein above, by reaction with a compound of formula (13a), wherein $R_5$, $R_6$, Q, Z and m have meaning as defined herein above, and Y is other than absent, in the presence of a base such as potassium carbonate ($K_2CO_3$), cesium carbonate ($Cs_2CO_3$), TEA, DIEA or 1,8-diazabicyclo[5.4.0]undec-7-ene (DBU) and an organic solvent such as DMF, acetone or acetonitrile. Preferably, the reaction is conducted by employing $K_2CO_3$ and acetone at a temperature of about 50° C.

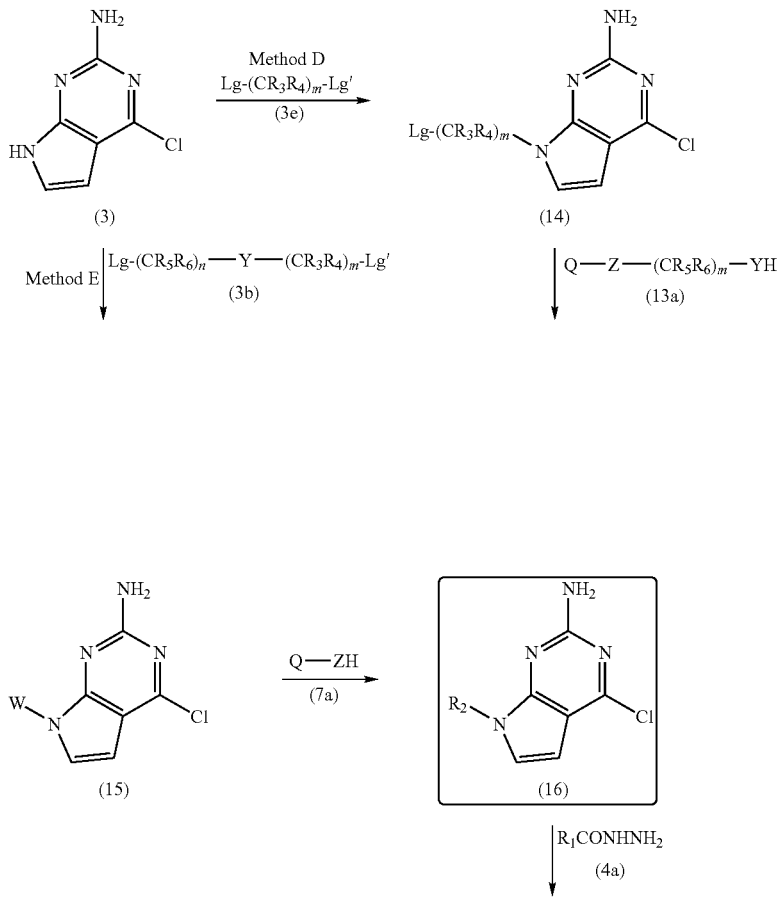

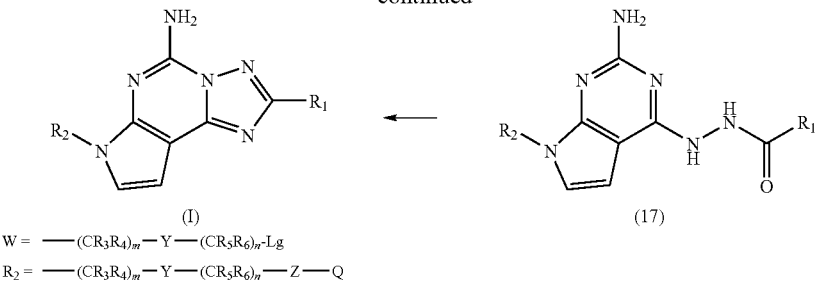

W = ——(CR$_3$R$_4$)$_m$—Y——(CR$_5$R$_6$)$_n$-Lg
R$_2$ = ——(CR$_3$R$_4$)$_m$—Y——(CR$_5$R$_6$)$_n$——Z—Q

Alternatively, as illustrated in Scheme 4 and designated herein as Method D, compounds of formula (I), wherein R$_1$ and R$_2$ have meaning as defined herein above, may also be prepared by treating 4-chloro-7H-pyrrolo[2,3-d]pyrimidin-2-amine of formula (3) with an alkylating agent of formula (3e), wherein R$_3$, R$_4$, m, Lg and Lg' have meaning as defined herein above, to afford a compound of formula (14), wherein R$_3$, R$_4$, m and Lg have meaning as defined herein above, under conditions well known in the art, or as described herein in the illustrative Examples. For example, 4-chloro-7H-pyrrolo[2,3-d]pyrimidin-2-amine of formula (3) may be treated with an alkylating agent of formula (3e), wherein R$_3$, R$_4$ and m have meaning as defined herein above, and Lg and Lg' represent halide, preferably bromide, in the presence of a base such as aqueous sodium hydroxide (NaOH) and a catalyst such as tetra-n-butylammonium bromide or tetra-n-butylammonium chloride, to afford a compound of formula (14), wherein R$_3$, R$_4$ and m have meaning as defined herein above, and Lg is halide, preferably bromide.

A resulting compound of formula (14), wherein R$_3$, R$_4$, m and Lg have meaning as defined herein above, may then be coupled with a compound of formula (13a), wherein R$_5$, R$_6$, Q, Z and m have meaning as defined herein above, and Y is other than absent, in the presence of a base such as K$_2$CO$_3$, Cs$_2$CO$_3$, TEA, DIEA or DBU and an organic solvent such as DMF, acetone or acetonitrile, to afford a compound of formula (16), wherein R$_2$ has meaning as defined herein above. Preferably, the reaction is conducted by employing K$_2$CO$_3$ and acetone at a temperature of about 50° C.

Alternatively, compounds of formula (16), wherein R$_2$ has meaning as defined herein above, designated herein as Method E, may be obtained by treating 4-chloro-7H-pyrrolo[2,3-d]pyrimidin-2-amine of formula (3) with an alkylating agent of formula (3b), wherein R$_3$, R$_4$, R$_5$, R$_6$, Y, m, n, Lg and Lg' have meaning as defined herein above, to afford a compound of formula (13), wherein W has meaning as defined herein above, in the presence of a base such as sodium hydride, and an organic solvent such as DMF. Preferably, the alkylation is conducted at a temperature ranging from about 0° C. to room temperature (RT).

A resulting compound of formula (15), wherein W has meaning as defined herein above, may then be coupled with a compound of formula (7a), wherein Q and Z have meaning as defined herein above, in the presence of a base such as potassium carbonate (K$_2$CO$_3$), cesium carbonate (Cs$_2$CO$_3$), TEA, DIEA or 1,8-diazabicyclo[5.4.0]undec-7-ene (DBU) and an organic solvent such as DMF, acetone or acetonitrile, to afford a compound of formula (16), wherein R$_2$ has meaning as defined herein above. Preferably, the reaction is conducted employing K$_2$CO$_3$ and acetone at a temperature of about 50° C.

A compound of formula (16), wherein R$_2$ has meaning as defined herein above, may then be condensed with a hydrazide of formula (4a), wherein R$_1$ has meaning as defined herein above, to afford a compound of formula (17), wherein R$_1$ and R$_2$ have meaning as defined herein above. Preferably, the condensation is carried out in an organic solvent such as NMP or a lower alcohol, e.g., n-BuOH, at a temperature near to the boiling point of the solvent.

Finally, a compound of formula (17), wherein R$_1$ and R$_2$ have meaning as defined herein above, may be cyclized in the presence of a base such as HMDS and a silylating agent such as BSA at a temperature of about 120° C., to afford a compound of formula (I), wherein R$_1$ and R$_2$ have meaning as defined herein above.

The processes described herein above may be conducted under inert atmosphere, preferably under nitrogen or argon atmosphere.

In starting compounds and intermediates which are converted to the compounds of the present invention in a manner described herein, functional groups present, such as amino, thiol, carboxyl and hydroxyl groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, RT or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts.

Compounds of the invention and intermediates can also be converted into each other according to methods generally known per se.

The present invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers, racemates or mixtures thereof. The aforesaid possible isomers or mixtures thereof are within the purview of the present invention.

Any resulting mixtures of isomers can be separated on the basis of the physicochemical differences of the constituents, into the pure geometric or optical isomers, diastereomers, for example, by fractional crystallization and/or chromatography, e.g., by high pressure liquid chromatography (HPLC) using a chiral adsorbent.

Finally, compounds of the invention are either obtained in the free form, or in a salt form thereof, preferably, in a pharmaceutically acceptable salt form thereof.

In particular, compounds of the invention which contain basic groups may be converted into acid addition salts, especially pharmaceutically acceptable acid addition salts. These are formed, e.g., with inorganic acids, such as mineral acids, e.g., sulfuric acid, phosphoric or hydrohalic acid, or with organic carboxylic acids, such as $C_1$-$C_4$ alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as $C_1$-$C_4$ alkylsulfonic acids, e.g., methanesulfonic acid; or arylsulfonic acids which are unsubstituted or substituted (for example by halogen). Preferred are salts formed with hydrochloric acid, maleic acid and methanesulfonic acid. Salts may be formed using conventional methods, advantageously in the presence of an ethereal or alcoholic solvent, such as a lower alkohol. From the solutions of the latter, the salts may be precipitated with ethers, e.g., with diethyl ether or petroleum ether. Resulting salts may be converted into the free compounds by treatment with a suitable base, e.g., sodium hydroxide. These or other salts can also be used for the purification of the compounds obtained.

In view of the close relationship between the free compounds and the compounds in the form of their salts, whenever a compound is referred to a corresponding salt is also intended, provided such is possible or appropriate under the circumstances.

The compounds, including their salts, can also be obtained in the form of their hydrates, or include other solvents used for their crystallization.

Furthermore, compounds of formula (I) may be obtained labeled with any suitable radiolabel. Examples of suitable radiolabels include tritium (3H) and carbon radioisotopes, e.g., $^{14}C$, but any substantially non-toxic radiolabel commonly used in pharmacokinetic studies may be employed. Means for incorporating radiolabels onto organic compounds are well known to those of ordinary skill in the art.

It has been established in the art, that $^3H$ and $^{14}C$ labeled compounds have binding affinity to the adenosine $A_1$, $A_{2A}$, $A_{2B}$, and $A_3$ receptor subtypes comparable to that of corresponding non-labeled forms and, thus, radiolabelled compounds of formula (I) may be employed as radioligands for studying biological activity associated with the adenosine receptors, in particular, the adenosine $A_{2A}$ receptor.

As described herein above, the compounds of the present invention are adenosine $A_{2A}$ receptor antagonists. Thus, the present invention provides a method for the modulation of the adenosine $A_{2A}$ receptor activity in mammals which method comprises administering to a mammal in need thereof a therapeutically effective amount of a compound of formula (I).

Furthermore, compounds of formula (I) may be employed for the treatment of conditions mediated by the adenosine $A_{2A}$ receptors. Accordingly, such compounds may be employed therapeutically for the treatment of diseases of the central nervous system such as depression, cognitive function diseases and neurodegenerative diseases such as Parkinson's disease, senile dementia as in Alzheimer's disease, psychoses and stroke; attention related disorders such as attention deficit disorder (ADD) and attention deficit hyperactivity disorder (ADHD); extra pyramidal syndrome, e.g., dystonia, akathisia, pseudoparkinsonism and tardive dyskinesia; and disorders of abnormal movement such as restless leg syndrome (RLS) and periodic limb movement in sleep (PLMS); cirrhosis, and fibrosis and fatty liver; dermal fibrosis in diseases such as scleroderma; and the mitigation of addictive behavior; by administering to a mammal in need thereof a therapeutically effective amount of a compound of the present invention. In particular, the compounds of the present invention may be employed to improve motor-impairment due to neurodegenerative diseases such as Parkinson's disease In a further aspect, the present invention provides a method as defined above comprising co-administration, e.g., concomitantly or in sequence, of a therapeutically effective amount of at least one compound of formula (I), or a pharmaceutically acceptable salt thereof, and one or more drug substances, said drug substances being agents useful in the treatment of Parkinson's disease, e.g., L-DOPA; a dopaminergic agonist such as quinpirole, ropinirole, pramipexole, pergolide and bromocriptine, in particular a dopamine $D_2$ agonist, e.g., apomorphine; an inhibitor of monoamine oxidase type B (MAO-B) such as deprenyl and selegiline; a DOPA decarboxylase inhibitor (DCI) such as carbidopa and benserazide; or a catechol-O-methyltransferase (COMT) inhibitor such as tolcapone and entacapone.

The invention also provides a method of treating restless leg syndrome (RLS) and periodic limb movement in sleep (PLMS) comprising administering a combination of at least one compound of formula (I) with one or more therapeutic agents useful in treating RLS or PLMS, such as levodopa/carbidopa, levodopa/benserazide, a dopamine agonist, a benzodiazepine, an opioid, an anticonvulsant or iron, to a paatient in need thereof.

The term "one or more" as used herein above means that one to three different drug substances/therapeutic agents, preferably one agent, may be employed in accordance of the methods of the present invention. Preferably, one agent is used in combination with one compound of formula (I).

The structure of the therapeutic agents identified by code numbers, generic or trade names may be taken from the actual edition of the standard compendium "The Merck Index" or from databases, e.g., Patents International (e.g. IMS World Publications).

The present invention further provides pharmaceutical compositions comprising a therapeutically effective amount of a compound of the present invention, alone or in combination with one or more pharmaceutically acceptable carriers.

The pharmaceutical compositions according to the invention are those suitable for enteral, such as oral or rectal, transdermal and parenteral administration to mammals, including man, for the treatment of conditions mediated by the adenosine $A_{2A}$ receptor. Such conditions include, but are not limited to, diseases of the central nervous system such as depression, cognitive function diseases and neurodegenerative diseases such as Parkinson's disease, senile dementia as in Alzheimer's disease, psychoses and stroke; attention related disorders such as attention deficit disorder (ADD) and attention deficit hyperactivity disorder (ADHD); extra pyramidal syndrome, e.g., dystonia, akathisia, pseudoparkinsonism and tardive dyskinesia; and disorders of abnormal movement such as restless leg syndrome (RLS) and periodic limb movement in sleep (PLMS); cirrhosis, and fibrosis and fatty liver; dermal fibrosis in diseases such as scleroderma; and the mitigation of addictive behavior. In particular, the compounds of the present invention may be employed to improve motor-impairment due to neurodegenerative diseases such as Parkinson's disease.

Thus, the compounds of the present invention may be employed in the manufacture of pharmaceutical compositions comprising a therapeutically effective amount thereof in conjunction or admixture with excipients or carriers suitable for either enteral or parenteral application. Preferred are tablets and gelatin capsules comprising the active ingredient together with: a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The compounds of the invention may be administered by inhalation from an inhaler, insufflator, atomizer or pressurized pack or other means of delivering an aerosol spray. Pressurized packs may use a suitable propellant such as carbon dioxide or other suitable gas. In the case of a pressurized aerosol, the dosage unit may be determined by providing a value to deliver a metered amount. The inhalers, insufflators, and atomizers are fully described in pharmaceutical reference books such as Remington's Pharmaceutical Sciences 18th edition (1990) Mack Publishing Co., Easton, Pa.

The amount of a compound of the present invention required for use in treatment will vary not only with the particular salt selected but also with the route of administration, the nature of the condition being treated and the age and condition of the patient and will be ultimately at the discretion of the administering physician or clinician. In general, a suitable dose will be in the range of from about 0.01 mg/kg/day to about 1000 mg/kg/day, preferably in the range of 0.1 mg/kg/day to about 100 mg/kg/day, and more preferably in the range of 1 mg/kg/day to 30 mg/kg/day. Generally, treatment is initiated with smaller dosages which are less than the optimum dose of the compound. Thereafter, the dosage is increased by small increments until the optimum effect under the circumstances is reached.

A unit dosage for a mammal of about 50 kg may contain between about 5 mg and 5000 mg, advantageously between about 50 mg to 1500 mg of the active ingredient. The therapeutically effective dosage of a compound of formula (I) is dependent on the species of warm-blooded animal (mammal), the body weight, age and individual condition, on the form of administration, and on the compound involved.

The desired dose may conveniently be presented in a single dose or as divided doses administered at appropriate intervals, for example, as two, three, four or more sub-doses per day. Dosages above or below the range cited herein above are within the scope of the present invention and may be administered to the individual patient if desired and necessary.

The doses and dosage regimen of L-DOPA, a dopaminergic agonist, in particular a dopamine $D_2$ agonist, e.g., apomorphine; a MAO-B inhibitor; a DCI inhibitor; and a COMT inhibitor, will be determined by the attending clinician in view of the approved doses and dosage regimen, e.g., in the package insert, taking into consideration the age, sex and condition of the patient and the severity of the disease. It is expected that when a combination of a compound of formula (I) and another therapeutic agent is administered, lower doses of the components will be effective compared to the doses of the components administered as monotherapy.

Accordingly, the present invention provides pharmaceutical compositions as described above for the treatment of conditions mediated by the adenosine $A_{2A}$ receptor including diseases of the central nervous system such as depression, cognitive function diseases and neurodegenerative diseases such as Parkinson's disease, senile dementia as in Alzheimer's disease, psychoses and stroke; attention related disorders such as attention deficit disorder (ADD) and attention deficit hyperactivity disorder (ADHD); extra pyramidal syndrome, e.g., dystonia, akathisia, pseudoparkinsonism and tardive dyskinesia; and disorders of abnormal movement such as restless leg syndrome (RLS) and periodic limb movement in sleep (PLMS); cirrhosis, and fibrosis and fatty liver; dermal fibrosis in diseases such as scleroderma; and the mitigation of addictive behavior. In particular, the compounds of the present invention may be employed to improve motor-impairment due to neurodegenerative diseases such as Parkinson's disease.

The pharmaceutical compositions may contain a therapeutically effective amount of a compound of the invention as defined above, either alone or in a combination with another therapeutic agents, e.g., each at an effective therapeutic dose as reported in the art. Such therapeutic agents include drug substances being an agent useful in the treatment of Parkinson's disease, e.g., dopamine; a dopaminergic agonist, in particular a dopamine $D_2$ agonist, e.g., apomorphine; an inhibitor of monoamine oxidase type B (MAO-B); a DOPA decarboxylase inhibitor (DCI); or a catechol-O-methyltransferase (COMT) inhibitor; and agents useful in treating RLS or PLMS, such as levodopa/carbidopa, levodopa/benserazide, a dopamine agonist, a benzodiazepine, an opioid, an anticonvulsant or iron.

As described above, a compound of the present invention may be administered either simultaneously, before or after the other active ingredients, either separately by the same or different route of administration or together in the same pharmaceutical formulation.

Accordingly, the present invention provides pharmaceutical compositions comprising a therapeutically effective amount of a compound of the invention in combination with a therapeutically effective amount of another therapeutic agent, preferably selected from drug substances being an agent useful in the treatment of Parkinson's disease, e.g., dopamine; a dopaminergic agonist, in particular a dopamine $D_2$ agonist, e.g., apomorphine; an inhibitor of monoamine oxidase type B (MAO-B); a DOPA decarboxylase inhibitor (DCI); or a catechol-O-methyltransferase (COMT) inhibitor; and agents useful in treating RLS or PLMS, such as levodopa/carbidopa, levodopa/benserazide, a dopamine agonist, a benzodiazepine, an opioid, an anticonvulsant or iron.

Since the present invention has an aspect that relates to treatment with a combination of compounds which may be co-administered separately, the invention also relates to combining separate pharmaceutical compositions in kit form. The kit comprises two or more separate pharmaceutical compositions, e.g.: (1) a composition comprising a compound of formula (I), or a pharmaceutically acceptable salt thereof, plus a pharmaceutically acceptable carrier or diluent; and (2) a composition comprising a drug substance being an agent useful in the treatment of Parkinson's disease, or an agents useful in treating RLS or PLMS, plus a pharmaceutically acceptable carrier or diluent. The amounts of (1) and (2) are such that, when co-administered separately, a beneficial therapeutic effect(s) is achieved. The kit comprises a container for containing the separate compositions such as a divided bottle or a divided foil packet, wherein each compartment contains a plurality of dosage forms (e.g., tablets) comprising (1) or (2). Alternatively, rather than separating the active ingredient-containing dosage forms, the kit may contain separate compartments each of which contains a whole dosage which in turn comprises separate dosage forms. An example of this type of kit is a blister pack wherein each individual blister contains two (or more) tablets, one (or more) tablet(s) comprising a pharmaceutical composition (1), and the second (or more) tablet(s) comprising a pharmaceutical composition (2). Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician. In the case of the present invention a kit therefore may comprise:

(1) a therapeutically effective amount of a composition comprising a compound of formula (I), or a pharmaceutically acceptable salt thereof, and a pharmaceutically acceptable carrier or diluent, in a first dosage form;

(2) a composition comprising a drug substance being an agent useful in the treatment of Parkinson's disease, or an agent useful in treating RLS or PLMS, in an amount such that, following administration, a beneficial therapeutic effect(s) is achieved, and a pharmaceutically acceptable carrier or diluent, in a second dosage form; and (3) a container for containing said first and second dosage forms.

The present invention further relates to pharmaceutical compositions as described above for use as a medicament.

Accordingly, the present invention further relates to use of pharmaceutical compositions or combinations as described above for the preparation of a medicament for the treatment of conditions mediated by the adenosine $A_{2A}$ receptor including diseases of the central nervous system such as depression, cognitive function diseases and neurodegenerative diseases such as Parkinson's disease, senile dementia as in Alzheimer's disease, psychoses and stroke; attention related disorders such as attention deficit disorder (ADD) and attention deficit hyperactivity disorder (ADHD); extra pyramidal syndrome, e.g., dystonia, akathisia, pseudoparkinsonism and tardive dyskinesia; and disorders of abnormal movement such as restless leg syndrome (RLS) and periodic limb movement in sleep (PLMS); cirrhosis, and fibrosis and fatty liver; dermal fibrosis in diseases such as scleroderma; and the mitigation of addictive behavior. In particular, the compounds of the present invention may be employed to improve motor-impairment due to neurodegenerative diseases such as Parkinson's disease.

Thus, the present invention also relates to a compound of formula (I) for use as a medicament, to the use of a compound of formula (I) for the preparation of a pharmaceutical composition for the treatment of conditions mediated by the adenosine $A_{2A}$ receptor, and to a pharmaceutical composition for use in conditions mediated by the adenosine $A_{2A}$ receptor comprising a compound of formula (I), or a pharmaceutically acceptable salt thereof, in association with a pharmaceutically acceptable diluent or carrier therefore.

Finally, the present invention provides a method or use which comprises administering a therapeutically effective amount of a combination of a compound of formula (I) and a drug substance being an agent useful in the treatment of Parkinson's disease, or an agent useful in treating RLS or PLMS.

Ultimately, the present invention provides a method or use which comprises administering a compound of formula (I) in the form of a pharmaceutical composition as described herein.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-2}$ molar and $10^{-9}$ molar concentrations. A therapeutically effective amount in vivo may range depending on the route of administration, between about 0.01 mg/kg and 1000 mg/kg, preferably between about 0.1 mg/kg and 100 mg/kg, more preferably between about 1 mg/kg and 30 mg/kg.

The activity of compounds according to the invention may be assessed using methods well-described in the art, e.g., as described herein below:

CHO Membranes Preparation

The human adenosine receptors have been transfected in CHO cells according with the method previously described by Klotz et al. (*Naunyn-Schmied. Arch Pharm.* 1998, 357: 1-9). Briefly, the cells are grown adherently and maintained in Dulbecco's Modified Eagles Medium with nutrient mixture F12 (DMEM/F12) without nucleosides, containing 10% fetal calf serum, penicillin (100 U/mL), streptomycin (100 µg/mL), L-glutamine (2 mM) and Geneticin (G418, 0.2 mg/ml) at 37° C. in 5% $CO_2$/95% air. For membrane preparation the culture medium is removed and the cells are ished with phosphate-buffered saline and scraped off T75 flasks in ice-cold hypo tonic buffer (5 mM Tris HCl, 1 mM EDTA, pH 7.4). The cell suspension is homogenized with Polytron, the homogenate is spun for 10 min at 1000×g and the supernatant is then centrifuged for 30 min at 100,000×g. The membrane pellet is suspended in 50 mM Tris HCl buffer (pH 7.4) for $A_1$ adenosine receptors, in 50 mM Tris HCl, 10 mM $MgCl_2$ (pH 7.4) for $A_{2A}$ adenosine receptors, in 50 mM Tris HCl, 10 mM $MgCl_2$, 1 mM EDTA (pH 7.4) for $A_{2B}$ and $A_3$ adenosine receptors.

Human Cloned $A_1$, $A_{2A}$, $A_{2B}$ and $A_3$ Adenosine Receptor Binding Assay All new synthesized compounds have been tested to evaluate their affinity to human $A_1$, $A_{2A}$, $A_{2B}$ and $A_3$ adenosine receptors. Displacement experiments of [$^3$H]DPCPX to CHO cells transfected with the human recombinant $A_1$ adenosine receptors are performed for 120 min at 25° C. incubating diluted membranes (50 µg of protein/assay) and at least 6-8 different concentrations of examined antagonists (Varani et al., *Mol. Pharmacol.*, 2000, 57: 968-975). Non-specific binding is determined in the presence of 10 µM of CHA and this is always $\leq$10% of the total binding. Binding of [$^3$H] ZM241385 to CHO cells transfected with the human recombinant $A_{2A}$ adenosine receptors is performed using a suspension of membranes (50 µg of protein/assay) and at least 6-8 different concentrations of studied antagonists for an incubation time of 60 min at 4° C. Non-specific binding is determined in the presence of 1 µM ZM 241385 and is about 20% of total binding. Competition binding experiments of [H]MRE-2029F20 to CHO cells transfected with the human recombinant $A_{2B}$ adenosine receptors are carried out incubating for 120 min at 4° C. diluted membranes (50 µg of protein/assay) and at least 6-8 different concentrations of examined compounds. Non-specific binding is defined as binding in the presence of 1 µM MRE-3029F20 and is about 25% of total binding. Competition binding experiments of [$^3$H]MRE-3008F20 to CHO cells transfected with the human recombinant $A_3$ adenosine receptors are carried out by incubating for 120 min at 4° C. diluted membranes (50 µg of protein/assay) and at least 6-8 different concentrations of examined ligands. Non-specific binding is defined as binding in the presence of 1 µM MRE-3008F20 and is about 25% of total binding. Bound and free radioactivity are separated by filtering the assay mixture through Whatman GF/B glass fiber filters using a Micro-Mate 196 cell harvester (Packard Instrument Co.). The filter bound radioactivity is counted on a Top Count (efficiency 57%) with Micro-Scint 20.

Measurement of Cyclic AMP Levels in CHO Cells Transfected with Human $A_{2A}$ Adenosine Receptors CHO cells transfected with human $A_{2A}$ adenosine receptors are washed with phosphate-buffered saline, diluted trypsine and centrifuged for 10 min at 200 g. The pellet containing the CHO cells (1×10$^6$ cells/assay) is suspended in 0.5 mL of incubation mixture: NaCl 150 mM, KCl 2.7 mM, $NaH_2PO_4$ 0.37 mM, $MgSO_4$ 1 mM, $CaCl_2$ 1 mM, Hepes 5 mM, $MgCl_2$ 10 mM, glucose 5 mM, pH 7.4 at 37° C. Then 2.0 IU/mL adenosine deaminase and 0.5 mM 4-(3-butoxy-4-methoxybenzyl)-2-imidazolidinone (Ro 20-1724) as phosphodiesterase inhibitor are added and preincubated for 10 min in a shaking bath at 37° C. The potency of antagonists studied are determined by antagonism of NECA (100 nM)-induced stimulation of cyclic AMP levels. The reaction is terminated by the addition of cold 6% thrichloroacetic acid (TCA). The TCA suspension is centrifuged at 2000 g for 10 min at 4° C. and the supernatant is extracted four times with water saturated diethyl ether. The final aqueous solution is tested for cyclic AMP levels by a competition protein binding assay. Samples of cyclic AMP standard (0-10 pmol) are added to each test tube containing the incubation buffer (trizma base 0.1 M, aminophylline 8.0 mM, 2-mercaptoethanol 6.0 mM (pH 7.4) and [$^3$H]cyclic AMP in a total volume of 0.5 mL. The binding protein previously prepared from beef adrenals, is added to the samples previously incubated at 4° C. for 150 min, and after the addition of charcoal are centrifuged at 2000 g for 10 min. The clear supernatant is counted with 4 mL of Atomlight liquid scintillator and counted in a Tri Carb Packard 2500 TR scintillation counter.

Data Analysis

The protein concentration is determined according to a Bio-Rad method (Bradford, *Anal Biochem.* 1976, 72: 248-254) with bovine albumin as a standard reference. Inhibitory binding constant, $K_i$, values are calculated from those of $IC_{50}$ according to Cheng & Prusoff equation (*Biochem. Pharmacol.* 1973, 22: 3099-3108):

$$K_i = IC_{50}/(1+[C^*]/K_D^*)$$

where [$C^*$] is the concentration of the radioligand and $K_D^*$ its dissociation constant. A weighted non linear least-squares curve fitting program LIGAND (Munson et al., *Anal. Biochem.* 1980, 107: 220-239) is used for computer analysis of inhibition experiments. Data are expressed as geometric mean with 95% confidence limits in parentheses.

Selectivity for the $A_{2A}$ receptor may determined by dividing the $K_i$ for the other adenosine receptors by the $K_i$ for $A_{2A}$ receptor. Preferred compounds of the present invention have a selectivity ranging from about 100 to about 10,000.

Haloperidol-Induced Catalepsy in the Rat

Male Sprague-Dawley rats (Charles River, Calco, Italy) weighing 175-200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rats are placed on the grid with all four legs abducted and extended ("frog posture"). The use of such an unnatural posture is essential for the specificity of this test for catalepsy. The time span from placement of the paws until the first complete removal of one paw (descent latency) is measured maximally for 120 seconds.

The selective $A_{2A}$ adenosine antagonists under evaluation are administered orally at doses ranging between 0.03 and 3 mg/kg, 1 and 4 h before scoring the animals.

6-OHDA Lesion of the Middle Forebrain Bundle in Rats

Protocol A:

Adult male Sprague-Dowley rats (Charles River, Calco, Como, Italy), weighing 275-300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described by Ungerstedt et al. (*Brain Research*, 24, 485-493, 1970; *European Journal of Pharmacology*, 5, 107-

110, 1968), with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame.

The skin over the skull is reflected and the stereotaxic coordinates [−2.2 posterior from bregma (AP), +1.5 lateral from bregma (ML), 7.8 ventral from dura (DV)] are taken, according to the atlas of Pellegrino et al. (A Stereotaxic Atlas of the Rat Brain, 1979, New York: Plenum Press). A burr hole is then placed in the skull over the lesion site and a needle, attached to a Hamilton syringe, is lowered into the left MFB. Then 8 µg 6-OHDA-HCl is dissolved in 4 µL of saline with 0.05% ascorbic acid as antioxidant, and infused at the constant flow rate of 1 µL/1 min using an infusion pump. The needle is withdrawn after additional 5 min and the surgical wound is closed and the animals left to recover for 2 weeks.

Two weeks after the lesion, the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonists are administered orally at dose levels ranging between 1 and 30 mg/kg at different time points (i.e., 1, 6 and 12 h) before the injection of a subthreshold dose of L-DOPA (4 mpk, ip) plus benserazide (4 mpk, ip) and the evaluation of turning behavior.

Protocol B:

Adult male Sprague-Dowley rats (Harlan UK ltd., Bicester, Oxon, UK), weighing 255±15 g, are used in all experiments. The rats are housed in groups of up to 5 per cage, and the animals are fed an expanded rodent diet of RM1(E) SQC (Special Diets Services, Witham, UK) ab libitum, and allowed free access to water, under controlled temperature and 12 hour light-dark cycle.

The test compounds are formulated for dosing by initially wet grinding a known amount in approximately 10% of the final volume of vehicle, i.e., propylene glycol/polyethylene glycol (PEG400)/glucose (D5W)-15/15/70 v %, in a mortal and pestle. Once suitably wetted, approximately 30% of the remaining vehicle is added, stirred for up to 10 min, and then sonicated for approximately 5 min. This step is repeated twice, using remaining vehicle to provide even suspensions of 0.6, 2 and 6 mg/mL. No correction factor is applied. All test substance formulations are clear to light tan colored suspensions, stored at RT and protected from light until dosing. The dose volume for the test compounds is 5 mL/kg to provide dosages of 3, 10 and 30 mg/kg, respectively.

Apomorphine hydrochloride (HCl) hemihydrate (Sigma, UK) is formulated for dosing by dissolving a known amount in 0.9% w/v sodium chloride (Baxter Healthcare Ltd., UK) to produce a clear, colorless solution of 0.02 mg/mL. A correction factor of 1.03 is applied to enable the doses of apomorphine HCl to be corrected for water content. All formulations are freshly prepared on each day of dosing, stored at RT and protected from light until use. The dose volume for apomorphine is 1 mL/kg.

6-OHDA hydrobomide (HBr, Sigma, UK) is formulated by dissolving a known amount in sterile 0.9% w/v sodium chloride containing ascorbic acid (Aldrich Chemical Co., UK) to produce a 3 mg/mL solution. Desipramine HCl (Sigma, UK) is formulated for dosing by dissolving a known amount in sterile water (Baxter Healthcare, UK) to produce a 25 mg/mL solution. Pargyline HCl (Sigma, UK) is formulated for dosing by dissolving a known amount in sterile water to produce a 50 mg/mL solution. No correction factors are applied during the formulation of 6-OHDA, desipramine HCl or pargyline HCl. All solutions are prepared freshly on each day of surgery, stored at RT and protected from light until use.

Each rat is given a dose of desipramine HCl (25 mg/kg i.p.) and pargyline HCl (50 mg/kg i.p.) immediately prior to being anaesthetized with isofluorine in oxygen. After shaving the scalp, the head is fixed in stereotaxic frame according to the atlas of Paxinos and Watson (1986). A midline longitudinal incision is made, and the skin flap retracted to reveal the surface of the skull. With the aid of an operating microscope, a small burr-hole is drilled overlying the left medial forebrain bundle (stereotaxic co-ordinates: AP-3.8 mm from bregma; L1.0 mm). The tip of an injection cannula (backfilled with injectate) is lowered to a depth of 8 mm below the surface of the skull so that the tip is located in the medial forebrain bundle. 6-OHDA HBr (6 µg in 2 µL) is injected over 5 min, with the cannula left in place for further 5 min. After removal of the cannula, the scalp wound is closed with sutures. Prior to recovery from anaesthesia, the animals are given 0.2 mg/kg of Metacam, and housed in groups of up to 3 during the subsequent recovery period, and allowed to recover for at least 14 days prior to the start of behavioral testing.

In order to help prevent the animals' overall condition to deteriorate significantly during the initial weight loss period of post-lesion recovery, each rat is given access to sunflower seeds, rasins, fresh banana sections, weetabix and RM1(E) SQC soaked in warm water and subcutaneous fluids, in the case of dehydration.

A 15-channel Rotometry System (Letica Scientific Instruments, Barcelona, Spain) is used for the circling tests. Prior to behavioral testing with apomorphine, each rat is placed in a swivel-harness in a rotometry bowl (diameter 24 cm) and allowed 5 min to spontaneously rotate. For each rat, the clockwise rotations are subtracted from the anticlockwise rotations to give the net spontaneous ipsilateral (anticlockwise) rotations. Immediately following the spontaneous rotations each rat is tested with apomorphine HCl (0.3 mg/kg i.p.). Clockwise and anticlockwise rotations are logged automatically for 60 min post-apomorphine administration.

Animals are arbitrarily allocated to the treatment groups prior to dosing based on the pre-dose contralateral baseline values for the rotometry test (Day 14 PO). Animals are allocated such that the mean apomorphine response is approximately equal throughout all the treatment groups. Only animals which turn ≧200 times, in the 60 min following apomorphine administration, are included in the study.

The allocated animals each receive a single intraperitoneal dose, by gavage, of a test compound or vehicle on approximately Days 21 and 30 PO (acute dose). On approximately Days 28 and 29 PO (chronic dosing), each animal receive 2 intraperitoneal doses, by gavage, and each injection is separated by approximately 8 h. Assessment of rotation behavior is performed on approximately Days 21 and 30 PO, immediately after a threshold dose of apomorphine HCl (0.02 mg/kg i.p.) is administered to each animal. Behavioral testing is performed at approximately 90 min post a test compound or vehicle administration, to investigate treatment effect.

Illustrative of the invention, the compounds of Examples 4, 29 and 30 bind to the human adenosine $A_{2A}$ receptor with $K_i$ values of about 1 nM, about 28 nM and about 5 nM, respectively. Furthermore, as illustrated in FIG. 1, the compound of Example 30 exhibits a significant increase in the number of contralateral rotations (228±38; p≦0.05) at 30 mg/kg when tested in the 6-OHDA lesion rats challenged with a threshold dose of apomorphine (0.02 mg/kg i.p.).

The Examples disclosed herein are intended to illustrate the invention and are not to be construed as being limitations thereon. If not mentioned otherwise, all evaporations are performed under reduced pressure, preferably between about 10 mmHg and 100 mmHg. The structure of final products, intermediates and starting materials is confirmed by standard analytical methods, e.g., microanalysis, melting point (m.p.) and spectroscopic characteristics, e.g., MS, IR and NMR. Abbreviations used are those conventional in the art.

Example 1

7-(2-(4-(2,5-Difluorophenyl)piperazin-1-yl)ethyl)-2-(furan-2-yl)-7H-pyrrolo[3,2-e][1,2,4]triazolo[1,5-c]pyrimidin-5-amine, Method A

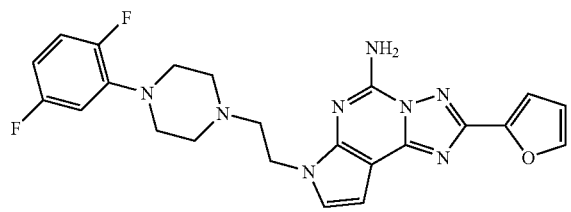

A. 7-[2-(t-Butyldimethylsilanyloxy)ethyl]-4-chloro-7H-pyrrolo[2,3-d]pyrimidin-2-amine To a suspension of NaH (0.618 g, 15.45 mmol) in anhydrous DMF (15 mL) at 0° C. is added slowly a solution of 4-chloro-7H-pyrrolo[2,3-d]pyrimidin-2-amine (2 g, 11.86 mmol) in 5 mL of anhydrous DMF. The mixture is stirred at this temperature under $N_2$ for 15 min, then (2-bromoethoxy)-t-butyldimethylsilane (4.0 mL, 18.64 mmol) is added at 0° C. The mixture is stirred at RT overnight. The reaction mixture is poured into water and extracted with ethyl acetate (EtOAc; 4×). The organic layer is dried over anhydrous magnesium sulfate ($MgSO_4$), filtered and concentrated in vacuo. The crude product is purified by flash cromatography using EtOAc/cyclohexane (1/1) as eluent to yield 7-[2-(t-butyldimethylsilanyloxy)ethyl]-4-chloro-7H-pyrrolo[2,3-d]pyrimidin-2-amine as white needles: LC/MS (M+1=327). $^1$H NMR ($CDCl_3$, 400 MHz) δ −0.08 (s, 6H), 0.84 (s, 9H), 3.88 (t, 2H, J=5.2 Hz), 4.17 (t, 2H, J=5.2 Hz), 4.89 (s, 2H, $NH_2$), 6.35 (d, 1H, J=3.6 Hz), 6.90 (d, 11, J=16 Hz).

B. Furan-2-carboxylic acid N'-{2-amino-7-[2-(t-butyldimethylsilanyloxy)ethyl]-7H-pyrrolo[2,3-d]pyrimidin-4-yl}-hydrazide The title A compound, 7-[2-(t-Butyldimethylsilanyloxy)ethyl]-4-chloro-7H-pyrrolo[2,3-d]pyrimidin-2-amine (100 mg, 0.3 mmol) and 2-furoic acid hydrazide (76 mg, 0.6 mmol) are taken into 3 mL of n-butanol. The mixture is stirred at 120° C. under $N_2$ for 2 h. The solvent is evaporated under vacuum and the residue is purified by flash chromatography using EtOAc/MeOH (95/5) as eluent to give furan-2-carboxylic acid N'-{2-amino-7-[2-(t-butyldimethylsilanyloxy) ethyl]-7H-pyrrolo[2,3-d]pyrimidin-4-yl}-hydrazide: LC/MS (M+1=417). $^1$H NMR ($CDCl_3$, 400 MHz) δ −0.08 (s, 6H), 0.84 (s, 9H), 3.85 (t, 2H, J=4.8 Hz), 4.12 (t, 2H, J=4.8 Hz), 4.81 (brs, 2H, $NH_2$), 6.26 (d, 1H, J=2.4 Hz), 6.51 (m, 1H), 6.74 (d, 1H, J=2.4 Hz), 7.20 (d, 1H, J=2.8 Hz), 7.27 (d, 1H, J=2.8 Hz), 7.49 (s, 1H).

C. 2-{5-Amino-2-(furan-2-yl)-7H-pyrrolo[3,2-e][1,2,4]triazolo[1,5-c]pyrimidin-7-yl}ethanol A mixture of the title B compound, 2-carboxylic acid N'-{2-amino-7-[2-(t-butyldimethylsilanyloxy)ethyl]-7H-pyrrolo[2,3-d]pyrimidin-4-yl}-hydrazide (2 g, 4.8 mmol), N,O-bis(trimethylsilyl)acetamide (6.10 g, 30 mmol) and 5 mL of hexamethyldisilazide is heated at 120° C. overnight. After removing volatiles under vacuum, the residue is dissolved in 10 mL of EtOH, and 2 mL of 6N aqueous hydrochloric acid (HCl) are added at 0° C. The reaction mixture is stirred at RT for 0.5 h. The precipitate is collected by filtration to give 2-{5-amino-2-(furan-2-yl)-7H-pyrrolo[3,2-e][1,2,4]triazolo[1,5-c]pyrimidin-7-yl}ethanol as a white solid: LC/MS (M+1=285). $^1$H NMR (DMSO-$d_6$, 400 MHz) δ 3.74 (t, 2H, J=6.4 Hz), 4.18 (t, 2H, J=6.4 Hz), 6.59 (d, 1H, J=3.6 Hz), 6.72 (m, 1H), 7.13 (d, 1H, J=3.6 Hz), 7.21 (d, 1H, J=3.2 Hz), 7.51 (br s, 2H, $NH_2$), 7.92 (s, 1H).

D. 2-{5-Amino-2-(furan-2-yl)-7H-pyrrolo[3,2-e][1,2,4]triazolo[1,5-c]pyrimidin-7-yl}ethyl methanesulfonate To a solution of the title C compound, 2-{5-amino-2-(furan-2-yl)-7H-pyrrolo[3,2-e][1,2,4]triazolo[1,5-c]pyrimidin-7-yl}ethanol (15 g, 5.28 mmol) in 45 mL of dry THF is added 75 mL of TEA, 75 mL of pyridine and methanesulfonyl chloride (0.6 mL, 7.75 mmol) at 0° C. The mixture is stirred at RT under $N_2$ for 12 h. The solvent is evaporated in vacuo and the residue is purified by flash chromatography using EtOAc as eluent to give 2-{5-amino-2-(furan-2-yl)-7H-pyrrolo[3,2-e][1,2,4]triazolo[1,5-c]pyrimidin-7-yl}ethyl methanesulfonate as a white solid: LC/MS (M+1=363.4). $^1$H NMR (DMSO-$d_6$, 400 MHz) δ 3.07 (s, 3H), 4.47 (t, 2H, J=5.2 Hz), 4=59 (t, 2H) J=5.2 Hz), 6.65 (d, 1H, J=3.6 Hz), 6.72 (dd, 1H, J=3.2 Hz and 1.6 Hz), 7.18 (d, 1H, J=3.6 Hz), 7.20 (d, 1H, J=3.2 Hz), 7.60 (s, 2H), 7.92 (d, 1H, J=1.2 Hz).

E. 1-(2,5-Difluorophenyl)piperazine hydrochloride 0.03 Mol of 2,5-difluoroaniline and 0.03 mol of bis-(2-chloroethyl)amine hydrochloride are suspended in 50 mL of xylene and 15 mL of NMP. The mixture is heated at 130° C. for 25 h while stirring, then cooled to RT and the solvents are evaporated. The residue is dissolved in water and 1 equivalent of 2N aqueous sodium hydroxide (NaOH) is added. The mixture is extracted with dichloromethane (DCM), and the organic layer is dried over anhydrous $MgSO_4$, filtered and evaporated to dryness in vacuo. The residue is dissolved in acetone and 1 equivalent of HCL in diethyl ether ($Et_2O$) is added. The precipitated product is collected by filtration and recrystallized from isopropanol to afford 1-(2,5-difluorophenyl)piperazine hydrochloride: m.p. 195° C. LC/MS (M+1=199.1). $^1$H NMR (DMSO-$d_6$, 400 MHz) δ 3.22 (m, 4H), 3.28 (m, 4H), 6.83 (m, 1H), 6.97 (m, 1H), 7.22 (m, 1H), 9.46 (br s, NH).

F. 7-(2-(4-(2,5-Difluorophenyl)piperazin-1-yl)ethyl)-2-(furan-2-yl)-7H-pyrrolo[3,2-e][1,2,4]triazolo[1,5-c]pyrimidin-5-amine To a solution of the title D compound, 2-{5-amino-2-(furan-2-yl)-7H-pyrrolo[3,2-e][1,2,4]triazolo[1,5-c]pyrimidin- 7-yl}ethyl methanesulfonate (0.06 g, 0.165 mmol) in dry DMF (5 mL), the title E compound, 1-(2,5-difluorophenyl)piperazine hydrochloride (0.33 mmol) and 0.06 mL of DIEA are added and the solution is stirred at 100° C. for 5 h. The reaction mixture is cooled to RT, and the solvent is removed under reduced pressure. To the residue, acetonitrile is added and the solution is stirred at 60° C. for 0.5 h. The solution is then cooled to RT, and the resulting solids are collected by filtration to give 7-(2-(4-(2,5-difluorophenyl)piperazin-1-yl)ethyl)-2-(furan-2-yl)-7H-pyrrolo[3,2-e][1,2,4]triazolo[1,5-c]pyrimidin-5-amine: LC/MS (M+1=465.2). $^1$H NMR (DMSO-$d_6$, 400 MHz) δ 2.64 (m, 4H), 2.76 (t, 2H, J=64 Hz), 3.01 (m, 4H), 4.28 (t, 2H, J=6.4 Hz), 6.60 (d, 1H, J=3.2 Hz), 6.72 (m, 1H), 6.75 (m, 1H), 6.80-6.85 (m, 1H), 7.12 (m, 1H), 7.18 (m, 2H), 7.51 (br s, 2H), 7.91 (s, 1H). Anal. calculated for ($C_{23}H_{22}F_2N_8O$): C, 59.48; H, 4.77; F, 8.18; N, 24.12; 0, 3.44. Found C, 59.45; H, 4.70; N, 24.19.

Example 2

7-(2-(4-(2,4-Difluorobenzyl)piperazin-1-yl)ethyl)-2-(furan-2-yl)-7H-pyrrolo[3,2-e][1,2,4]triazolo[1,5-c]pyrimidin-5-amine, Method A

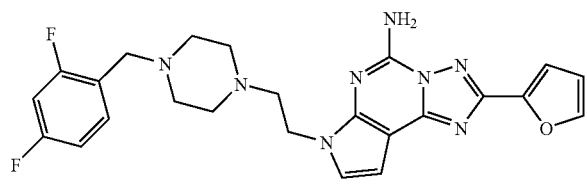

A. t-Butyl 4-(2,4-difluorobenzyl)piperazine-1-carboxylate

A mixture of 2,4-difluorobenzaldehyde (3.0 g, 21.1 mmol) and t-butyl piperazine-1-carboxylate (4.3 g, 23.1 mmol) in 30 mL of dry DCM is stirred for 2 h at RT, and NaHB(OAc)$_3$ (6.7 g, 31.6 mmol) is added in portions with stirring. After the addition, the reaction mixture is stirred further overnight at RT. Water is added and the resulting mixture is extracted twice with DCM. The organic layer is dried over anhydrous MgSO$_4$, filtered and concentrated in vacuo to obtain t-butyl 4-(2,4-difluorobenzyl)piperazine-1-carboxylate as a colorless oil: $^1$H NMR (CDCl$_3$, 400 MHz) δ 1.46 (s, 9H), 2.40 (m, 4H), 3.42 (m, 4H), 3.54 (s, 2H), 6.78 (dt, 1H, J=10.0 Hz and 2.4 Hz), 6.85 (dt, 1H, J=8.4 Hz and 2.4 Hz), 7.33 (dd, 1H, J=15.2 Hz and 8.0 Hz).

B. 4-(2,4-Difluorobenzyl)piperazine dihydrochloride

To a solution of 6.2 g (19.85 mmol) of the title A compound, t-butyl 4-(2,4-difluorobenzyl)piperazine-1-carboxylate in 50 mL of DCM at 0° C. is added 15 mL of trifluoroacetic acid. The reaction mixture is warmed to RT and stirred for 1 h, and 10 mL of 1N aqueous sodium hydroxide (NaOH) are added. The mixture is extracted with 2×100 mL of DCM and the organic layer is washed with water, dried over anhydrous MgSO$_4$ and evaporated to dryness in vacuo. The residue is dissolved in a mixture of DCM-Et$_2$O and two equivalents of HCl in Et$_2$O are added, the precipitate solid is collected by filtration and washed with acetone to afford 4-(2,4-difluorobenzyl)piperazine dihydrochloride as a white solid: m.p=237° C. LC/MS (M+1=213.1). $^1$H NMR (DMSO-$d_6$, 400 MHz) δ 3.44 (m, 8H), 4.39 (s, 2H), 7.25 (dt, 1H, J=8.4 Hz and 1.6 Hz), 7.43 (dt, 1H, J=9.2 Hz and 2.0 Hz), 7.84 (dd, 1H, J=15.2 Hz and 8.4 Hz), 9.84 (br s, NH). Anal. calculated for ($C_{11}H_{14}F_2N_2$, 2HCl+0.25H$_2$O) C, 45.61; H, 5.74; Cl, 24.48; F, 13.12; N, 9.67; O, 1.38. Found C, 45.56; H, 5.90; N, 9.68.

C. 7-(2-(4-(2,4-Difluorobenzyl)piperazin-1-yl)ethyl)-2-(furan-2-yl)-7H-pyrrolo[3,2-e][1,2,4]triazolo[1,5-c]pyrimidin-5-amine To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), the title B compound, 4-(2,4-difluorobenzyl)piperazine dihydrochloride (0.33 mmol) and 0.06 mL of DIEA are added and the solution is stirred at 100° C. for 5 h. The reaction mixture is cooled to RT, and the solvent is removed under reduced pressure. To the residue, acetonitrile is added and the solution is stirred at 60° C. for 0.5 h. The solution is then cooled to RT, and the resulting solids are collected by filtration to give 7-(2-(4-(2,4-difluorobenzyl)piperazin-1-yl)ethyl)-2-(furan-2-yl)-7H-pyrrolo[3,2-e][1,2,4]triazolo[1,5-c]pyrimidin-5-amine: LC/MS (M+1=478.2). $^1$H NMR (DMSO-$d_6$, 400 MHz) δ 2.30 (m, 4H), 2.36 (m, 4H), 2.67 (t, 2H, J=6.8 Hz), 3.47 (s, 2H), 4.22 (t, 2H, J=6.8 Hz), 6.58 (d, 1H, J=3.6 Hz), 6.72 (m, 1H), 7.06 (dt, 1H, J=8.4 Hz and 2.0 Hz), 7.14 (d, 1H, J=3.2 Hz), 7.20 (m, 2H), 7.42 (dd, 1H, J=15.2 Hz and 8.0 Hz), 7.54 (br s, NH$_2$), 7.93 (s, 1H). Anal. calculated for ($C_{24}H_{24}F_2N_8O$+0.5H$_2$O): C, 59.13; H, 5.17; F, 7.79; N, 22.98; 0, 4.92. Found C, 58.84; H, 4.97; N, 22.63.

Example 3

2-(Furan-2-yl)-7-(2-(4-((3-methylbenzo[b]thiophen-2-yl)methyl)piperazin-1-yl)ethyl)-7H-pyrrolo[3,2-e][1,2,4]triazolo[1,5-c]pyrimidin-5-amine, Method A

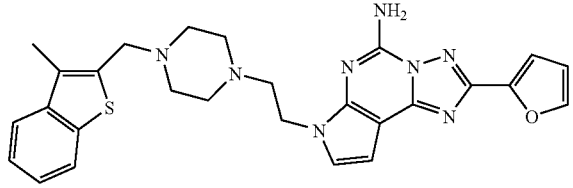

A. t-Butyl 4-((3-methylbenzo[b]thiophen-2-yl)methyl)piperazine-1-carboxylate

To a solution of 3-methylbenzo[b]thiophene-2-carbaldehyde (0.029 mol) in dry DCM (100 mL) is added t-butyl piperazine-1-carboxylate (0.0319 mol), and the mixture is stirred at RT for 1 h. 0.042 Mol of NaBH(OAc)$_3$ is added in portions, and the reaction mixture is stirred overnight at RT. The resulting solution is concentrated under vacuum, and the residue is partitioned between DCM and aqueous sodium bicarbonate solution. The organic phase is separated, washed with water, dried (MgSO$_4$) and evaporated in vacuo. The residue is purified by column chromatography on silica gel by eluting with DCM/MeOH (9/1) to afford t-butyl 4-((3-methylbenzo[b]thiophen-2-yl)methyl)piperazine-1-carboxylate.

B. 1-((3-Methylbenzo[b]thiophen-2-yl)methyl)piperazine dihydrochloride

The title A compound, t-butyl 4-((3-methylbenzo[b]thiophen-2-yl)methyl)piperazine-1-carboxylate is dissolved in dry DCM (50 mL), and 5 equiv. of TFA are added at 0° C. The reaction mixture is stirred at RT for 3 h. After the solvent is evaporated in vacuo, the residue is triturated in $Et_2O$, and the precipitate that forms is collected by filtration, washed with EtOH and dried in a vacuum oven at 40° C. overnight to give a hygroscopic solid. The solid is treated with sodium bicarbonate solution, and extracted with EtOAc. The organic layer is evaporated in vacuo, and the residue is dissolved in $Et_2O$ and treated with a solution of hydrochloric acid in $Et_2O$. The precipitated solid is collected by filtration and dried to give 1-((3-methylbenzo[b]thiophen-2-yl)methyl)piperazine dihydrochloride: LC/MS (M+1=247.1). $^1$H NMR (DMSO-$d_6$, 200 MHz) δ 2.48 (s, 3H), 3.39 (m, 4H), 3.54 (m, 4H), 4.63 (s, 2H), 7.45 (m, 2H), 7.84 (d, 1H, J=7.2 Hz), 7.95 (d, 1H, J=7.2 Hz), 9.52 (br s, NH). Anal. calculated for ($C_{14}H_{18}N_2S$ 2HCl): C, 52.66; H, 6.31; Cl, 22.21; N, 8.77; S, 10.04. Found: C, 52.70; H, 6.58; N, 8.77; S, 9.70.

C. 2-(Furan-2-yl)-7-(2-(4-((3-methylbenzo[b]thiophen-2-yl)methyl)piperazin-1-yl)ethyl)-7H-pyrrolo[3,2-e][1,2,4]triazolo[1,5-c]pyrimidin-5-amine To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), the title B compound, 1-[(3-methylbenzo[b]thiophen-2-yl)methyl]piperazine dihydrochloride (0.33 mmol) and 0.06 mL of DIEA are added, and the solution is stirred at 100° C. for 5 h. The reaction mixture is cooled to RT, and the solvent is removed under reduced pressure. To the residue, acetonitrile is added and the solution is stirred at 60° C. for 0.5 h. The solution is then cooled to RT, and the resulting solids are collected by filtration to give 2-(furan-2-yl)-7-(2-(4-((3-methylbenzo[b]thiophen-2-yl)methyl)piperazin-1-yl)ethyl)-7H-pyrrolo[3,2-e][1,2,4]triazolo[1,5-c]pyrimidin-5-amine: LC/MS (M+1=513.2). $^1$H NMR (DMSO-$d_6$, 400 MHz) δ 2.32 (s, 3H), 2.50 (m, 8H), 2.69 (t, 2H, J=6.4 Hz), 3.72 (s, 2H), 4.23 (t, 2H, J=6.4 Hz), 6.58 (d, 1H, J=3.2 Hz), 6.71 (m, 1H), 7.15 (d, 1H, J=3.6 Hz), 7.18 (d, 1H, J=3.2 Hz), 7.28-7.38 (m, 2H), 7.50 (br s, 2H), 7.68 (d, 1H, J=7.6 Hz), 7.85 (d, 1H, J=7.6 Hz), 7.92 (d, 1H, J=0.8 Hz).

Example 4

(4-(2-(5-Amino-2-(furan-2-yl)-7H-pyrrolo[3,2-e][1,2,4]triazolo[1,5-c]pyrimidin-7-yl)ethyl)piperazin-1-yl)(2,4-difluorophenyl)methanone, Method A

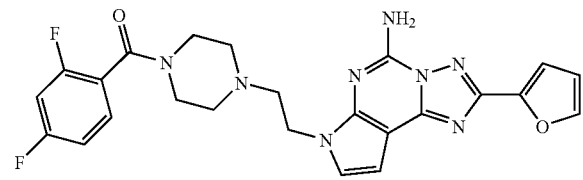

A. t-Butyl 4-(2,4-difluorobenzoyl)piperazine-1-carboxylate

To a solution of 3.0 g (19 mmol) of 2,4-difluorobenzoic acid and 4 mL of DIEA (1.2 equiv.) in 40 mL of dry DCM is added 3.08 g (1.2 equiv) of HOBt and 4.2 g (22.55 mmol) of t-butyl piperazine-1-carboxylate, and the mixture was stirred at RT for 30 min. 4.4 g (11 equiv.) of EDCl are added and the reaction mixture is stirred overnight at RT. Water is added and the resulting mixture is extracted with DCM. The organic layer is dried over anhydrous $MgSO_4$, filtered and concentrated in vacuo to obtain t-butyl 4-(2,4-difluorobenzoyl)piperazine-1-carboxylate as a yellow oil: $^1$H NMR (CDCl$_3$, 400 MHz) δ 1.47 (s, 9H), 3.30 (m, 2H), 3.41 (m, 2H), 3.53 (m, 2H), 3.76 (m, 2H), 6.86 (dt, 1H, J=8.8 Hz and 0.8 Hz), 6.97 (dt, 1H, J=8.8 Hz and 0.8 Hz), 7.41 (dd, 1H, J=14.4 Hz and 7.2 Hz).

B. (2,4-Difluorophenyl)piperazin-1-yl-methanone hydrochloride

The title compound, (2,4-difluorophenyl)piperazin-1-yl-methanone hydrochloride is obtained analogously to the title B compound of Example 2: m.p.=227° C. LC/MS (M+1=227.1). $^1$H NMR (DMSO-$d_6$, 400 MHz) δ 3.05 (m, 2H), 3.17 (m, 2H), 3.50 (m, 2H), 3.87 (m, 2H), 7.23 (dt, 1H, J=8.4 Hz and 2.0 Hz), 7.41 (dt, 1H, J=92 Hz and 2.0 Hz), 7.58 (dd, 1H, J=15.2 Hz and 7.2 Hz), 9.59 (br s, NH). Anal. calculated for ($C_{11}H_{12}F_2N_2O$·HCl+0.25$H_2O$): C, 49.45; H, 5.09; Cl, 13.27; F, 14.22; N, 10.48; 0, 7.48. Found C, 49.38; H, 5.15; N, 10.51.

C. (4-(2-(5-Amino-2-(furan-2-yl)-7H-pyrrolo[3,2-e][1,2,4]triazolo[1,5-c]pyrimidin-7-yl)ethyl)piperazin-1-yl)(2,4-difluorophenyl)methanone To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), the title B compound, (2,4-difluorophenyl)piperazin-1-yl-methanone hydrochloride (0.33 mmol) and 0.06 mL of DIEA are added, and the solution is stirred at 100° C. for 5 h. The reaction mixture is cooled to RT, and the solvent is removed under reduced pressure. To the residue, acetonitrile is added and the solution is stirred at 60° C. for 0.5 h. The solution is then cooled to RT, and the resulting solids are collected by filtration to give (4-(2-(5-amino-2-(furan-2-yl)-7H-pyrrolo[3,2-e][1,2,4]triazolo[1,5-c]pyrimidin-7-yl)ethyl)piperazin-1-yl)(2,4-difluorophenyl)methanone: LC/MS (M+1=493.1). $^1$H NMR (DMSO-$d_6$, 400 MHz) δ 2.42 (m, 2H), 2.72 (t, 2H, J=6.0 Hz), 3.17 (m, 2H), 3.34 (m, 2H), 3.60 (m, 2H), 4.25 (t, 2H, J=6.0 Hz), 6.59 (d, 1H, J=3.2 Hz), 6.72 (m, 1H), 7.18 (m, 3H), 7.38 (m, 1H), 7.46 (m, 1H), 7.54 (brs, 2H, $NH_2$), 7.93 (s, 1H). Anal. calculated for ($C_{24}H_{22}F_2N_8O_2$+0.5$H_2O$): C, 57.48; H, 4.62; F, 7.58; N, 22.34; 0, 7.98. Found C, 57.40; H, 4.46; N, 22.29.

Example 5

1-(4-(2-(5-Amino-2-(furan-2-yl)-7H-pyrrolo[3,2-e][1,2,4]triazolo[1,5-c]pyrimidin-7-yl)ethyl)piperazin-1-yl)-2-(2,4-difluorophenyl)ethanone, Method A

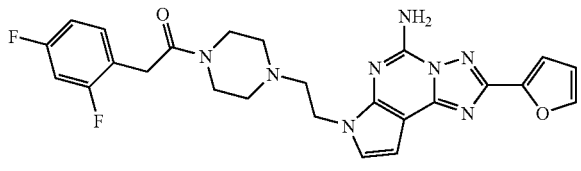

A. (2,4-Difluorophenyl)piperazin-1-yl-ethanone hydrochloride

The title A compound, (2,4-difluorophenyl)piperazin-1-yl-ethanone hydrochloride is obtained analogously to the title B compound of Example 4 starting from 2,4-difluorophenylacetic acid: m.p.=228° C. LC/MS (M+1=241.1). $^1$H NMR (DMSO-$d_6$, 400 MHz) δ 3.04 (m, 2H), 3.13 (m, 2H), 3.69 (m, 2H), 3.78 (m, 2H), 3.79 (s, 2H), 7.04 (dt, 1H, J=8.4 Hz and 2.4 Hz), 7.19 (dt, 1H, J=9.6 Hz and 2.4 Hz), 7.29 (dd, 1H, J=15.2 Hz and 8.4 Hz), 9.60 (brs, NH). Anal. calculated for ($C_{12}H_{14}F_2N_2O$, HCl): C, 52.09; H, 5.46; $C_{1-12.81}$; F, 13.73; N, 10.12; 0, 5.78. Found C, 52.00; H, 5.50; N, 10.13.

B. 1-(4-(2-(5-Amino-2-(furan-2-yl)-7H-pyrrolo[3,2-e][1,2,4]triazolo[1,5-c]pyrimidin-7-yl)ethyl)piperazin-1-yl)-2-(2,4-difluorophenyl)ethanone To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), the title A compound, (2,4-difluorophenyl)piperazin-1-yl-ethanone hydrochloride (0.33 mmol) and 0.06 mL of DIEA are added, and the solution is stirred at 100° C. for 5 h. The reaction mixture is cooled to RT, and the solvent is removed under reduced pressure. To the residue, acetonitrile is added and the solution is stirred at 60° C. for 0.5 h. The solution is then cooled to RT, and the resulting solids are collected by filtration to give 1-(4-(2-(5-amino-2-(furan-2-yl)-7H-pyrrolo[3,2-e][1,2,4]triazolo[1,5-c]pyrimidin-7-yl)ethyl)piperazin-1-yl)-2-(2,4-difluorophenyl)ethanone: LC/MS (M+1=507.2). $^1$H NMR (DMSO-$d_6$, 400 MHz) δ 2.45 (m, 4H), 2.72 (t, 2H, J=6.4 Hz), 3.43 (m, 2H), 3.48 (m, 2H), 3.69 (s, 2H), 4.26 (t, 2H, J=6.4 Hz), 6.59 (d, 1H, J=32 Hz), 6.71 (m, 1H), 7.01 (dt, 1H, J=8.4 Hz and 1.6 Hz), 7.17 (m, 3H), 7.28 (m, 1H), 7.49 (br s, 2H, NH$_2$), 7.91 (s, 1H). Anal. calculated for ($C_{25}H_{24}F_2N_8O_2$+⅓$H_2O$): C, 58.59; H, 4.85; F, 7.41; N, 21.86; 0, 7.28. Found C, 58.73; H, 5.06; N, 21.22.

Example 6

1-(4-(2-(5-Amino-2-(furan-2-yl)-7H-pyrrolo[3,2-e][1,2,4]triazolo[1,5-c]pyrimidin-7-yl)ethyl)piperazin-1-yl)-3-(2,4-difluorophenyl)propan-1-one, Method A

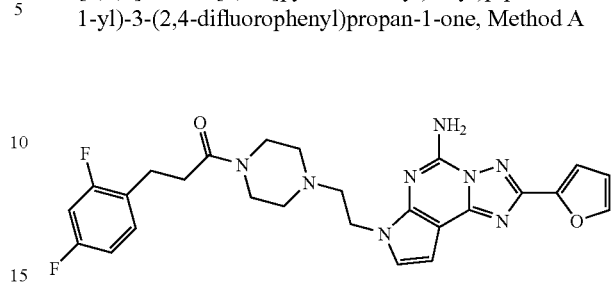

A. (2,4-Difluorophenyl)piperazin-1-yl-propanone hydrochloride

A solution of 5.0 g (27.15 mmol) of 3-(2,4-difluorophenyl)acrylic acid in EtOH (50 mL) is hydrogenated over PtO$_2$ catalyst under atmospheric pressure and stirred overnight at RT. After filtration to remove the catalyst, the filtrate is concentrated in vacuo to afford 3-(2,4-difluorophenyl)propanoic acid as a white solid: m.p. 104° C. $^1$H NMR (CDCl$_3$, 400 MHz) δ 2.67 (t, 2H, J=7.6 Hz), 2.94 (t, 2H, J=7.6 Hz), 6.80 (m, 2H), 7.18 (dd, 1H, J=14.8 Hz and 8.0 Hz). The title A compound, (2,4-difluorophenyl)piperazin-1-yl-propanone hydrochloride is obtained analogously to the title B compound of Example 4 as a white solid: m.p=221° C. LC/MS (M+1=255.1). $^1$H NMR (DMSO-$d_6$, 400 MHz) δ 2.66 (t, 2H, J=7.6 Hz), 2.81 (t, 2H, J=7.6 Hz), 3.01 (m, 2H), 3.05 (m, 2H), 3.69 (m, 4H), 7.02 (dt, 1H, J=8.4 Hz and 2.4 Hz), 7.18 (dt, 1H, J=10.0 Hz and 28 Hz), 7.29 (dd, 1H, J=15.6 Hz and 8.8 Hz), 9.65 (br s, NH). Anal. calculated for ($Cl_3H_{16}F_2N_2O$ HCl+0.2$H_2O$): C, 53.05; H, 5.96; Cl, 12.04; F, 12.91; N, 9.52; O, 6.52. Found C, 53.01; H, 5.96; N, 9.74.

B. 1-(4-(2-(5-Amino-2-(furan-2-yl)-7H-pyrrolo[3,2-e][1,2,4]triazolo[1,5-c]pyrimidin-7-yl)ethyl)piperazin-1-yl)-3-(2,4-difluorophenyl)propan-1-one To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), the title A compound, (2,4-difluorophenyl)piperazin-1-yl-propanone hydrochloride (0.33 mmol) and 0.06 mL of DIEA are added, and the solution is stirred at 100° C. for 5 h. The reaction mixture is cooled to RT, and the solvent is removed under reduced pressure. To the residue, acetonitrile is added and the solution is stirred at 60° C. for 0.5 h. The solution is then cooled to RT, and the resulting solids are collected by filtration to give 1-(4-(2-(5-amino-2-(furan-2-yl)-7H-pyrrolo[3,2-e][1,2,4]triazolo[1,5-c]pyrimidin-7-yl)ethyl)piperazin-1-yl)-3-(2,4-difluorophenyl)propan-1-one: LC/MS (M+1=521.2). $^1$H NMR (DMSO-$d_6$, 400 MHz), δ 2.40 (m, 4H), 2.58 (t, 2H, J=7.2 Hz), 2.68 (t, 2H, J=6.4 Hz), 2.79 (t, 2H, J=7.2 Hz), 3.37 (m, 2H), 3.41 (m, 2H), 4.25 (t, 2H, J=6.4 Hz), 6.59 (d, 1H, J=3.2 Hz), 6.71 (m, 1H), 6.99 (dt, 1H, J=8.4 Hz and 2.0 Hz), 7.15 (m, 2H), 7.18 (d, 1H, J=3.6 Hz), 7.36 (m, 1H), 7.49 (br s, 2H, NH$_2$), 7.91 (s, 1H). Anal calculated for ($C_{26}H_{26}F_2N_8O_2$+⅓$H_2O$): C, 59.31; H, 5.10; F, 7.22; N, 21.28; 0, 7.09. Found C, 59.16; H, 4.81; N, 20.98.

Example 7

7-(2-(4-(2,4-Difluorophenethyl)piperazin-1-yl)ethyl)-2-(furan-2-yl)-7H-pyrrolo[3,2-e][1,2,4]triazolo[1,5-c]pyrimidin-5-amine, Method A

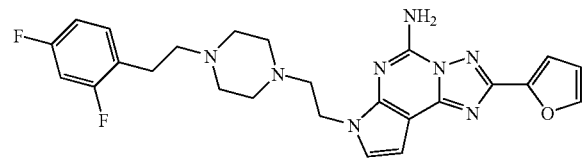

A. 1-(2,4-Difluorophenethyl)piperazine dihydrochloride

To a mixture of 15 mL of 2N $BH_3$ dimethylsulfide in THF is added dropwise a solution of 0.35 g (1.5 mmol) of the title A compound of Example 5 in 10 mL of dry THF, and the resulting mixture is stirred overnight at RT. The reaction mixture is poured into MeOH and a solution of hydrochloric acid in isopropanol. After stirring for 5 min, solvents are evaporated to dryness in vacuo and the residue is triturated in acetone to afford 1-(2,4-difluorophenethyl)piperazine dihydrochloride as a white solid: m.p.=280° C. LC/MS (M+1=227.1). $^1$H NMR (DMSO-$d_6$, 400 MHz) δ 3.10 (m, 2H), 3.34 (m, 4H), 3.46 (m, 4H), 3.74 (m, 2H), 7.09 (dt, 1H, J=8.4 Hz and 2.4 Hz), 7.26 (dt, 1H, J=10.0 Hz and 2.4 Hz), 7.46 (dd, 1H, J=15.6 Hz and 8.8 Hz), 9.90 (br s, NH). Anal. calculated for ($C_{12}H_{16}F_2N_2$ 2HCl+0.2$H_2O$): C, 47.60; H, 6.13; Cl, 23.42; F, 12.55; N, 9.25; 0, 1.06. Found C, 47.64; H, 5.94; N, 9.33.

B. 7-(2-(4-(2,4-Difluorophenethyl)piperazin-1-yl)ethyl)-2-(furan-2-yl)-7H-pyrrolo[3,2-e][1,2,4]triazolo[1,5-c]pyrimidin-5-amine To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), the title A compound, 1-(2,4-difluorophenethyl)piperazine dihydrochloride (0.33 mmol) and 0.06 mL of DIEA are added, and the solution is stirred at 100° C. for 5 h. The reaction mixture is cooled to RT, and the solvent is removed under reduced pressure. To the residue, acetonitrile is added and the solution is stirred at 60° C. for 0.5 h. The solution is then cooled to RT, and the resulting solids are collected by filtration to give 7-(2-(4-(2,4-difluorophenethyl)piperazin-1-yl)ethyl)-2-(furan-2-yl)-7H-pyrrolo[3,2-e][1,2,4]triazolo[1,5-c]pyrimidin-5-amine: LC/MS (M+1=493.2). $^1$H NMR (CDCl$_3$, 400 MHz) δ 2.55 (m, 10H), 2.78 (t, 4H, J=6.8 Hz), 4.28 (t, 2H, J=6.8 Hz), 5.67 (s, 2H), 6.58 (d, 1H, J=3.6 Hz), 6.73-6.80 (m, 3H), 6.97 (m, 1H), 7.15 (m, 1H), 7.24 (m, 1H), 7.61 (s, 1H).

Example 8

7-(2-(4-(3-(2,4-Difluorophenyl)propyl)piperazin-1-yl)ethyl)-2-(furan-2-yl)-7H-pyrrolo[3,2-e][1,2,4]triazoio[1,5-c]pyrimidin-5-amine, Method A

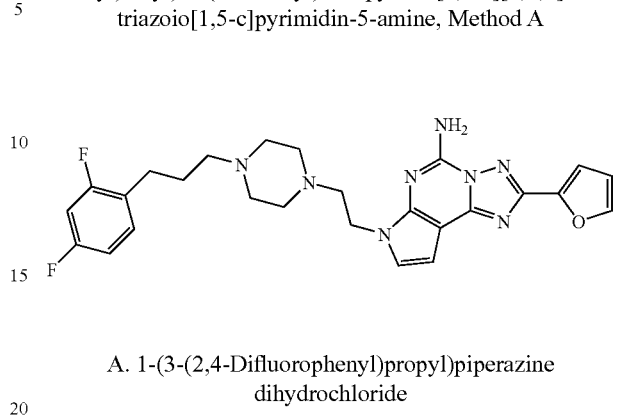

A. 1-(3-(2,4-Difluorophenyl)propyl)piperazine dihydrochloride

The title A compound, 1-(3-(2,4-difluorophenyl)propyl)piperazine dihydrochloride is obtained analogously to the title A compound of Example 7 by reduction of the title A compound of Example 6: m.p.=245° C. LC/MS (M+1=241.1). $^1$H NMR (DMSO-$d_6$, 400 MHz) δ1.99 (quintuplet, 2H, J=7.6 Hz), 2.65 (t, 2H, J=7.6 Hz), 3.15 (m, 2H), 3.27 (m, 2H), 3.44 (m, 4H), 3.67 (m, 2H), 7.06 (dt, 1H, J=8.4 Hz and 2.4 Hz), 7.22 (dt, 1H, J=10.4 Hz and 2.4 Hz), 7.40 (dd, 1H, J=15.6 Hz and 8.8 Hz), 9.85 (br s, NH). Anal. calculated for ($C_{13}H_{18}F_2N_2$ 2HCl+0.5$H_2O$): C, 48.46; H, 6.57; Cl, 22.00; F, 11.79; N, 8.69; 0, 2.48. Found C, 48.22; H, 6.45; N, 8.68.

B. 7-(2-(4-(3-(2,4-Difluorophenyl)propyl)piperazin-1-yl)ethyl)-2-(furan-2-yl)-7H-pyrrolo[3,2-e][1,2,4]triazolo[1,5-c]pyrimidin-5-amine To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), the title A compound, 1-(3-(2,4-difluorophenyl)propyl)piperazine dihydrochloride (0.33 mmol) and 0.06 mL of DIEA are added, and the solution is stirred at 100° C. for 5 h. The reaction mixture is cooled to RT, and the solvent is removed under reduced pressure. The crude product is purified by flash chromatography using DCM/MeOH/$NH_4OH$-95/5.0/0.5 as eluent to give 7-(2-(4-(3-(2,4-difluorophenyl)propyl)piperazin-1-yl)ethyl)-2-(furan-2-yl)-7H-pyrrolo[3,2-e][1,2,4]triazolo[1,5-c]pyrimidin-5-amine: LC/MS (M+1=507.2). $^1$H NMR (DMSO-$d_6$, 400 MHz) δ 1.66 (quintuplet, 2H, J=7.2 Hz), 2.24 (t, 2H, J=7.2 Hz), 2.32 (m, 4H), 2.45 (m, 4H), 2.58 (t, 2H, J=7.2 Hz), 2.67 (t, 2H, J=6.4 Hz), 4.22 (t, 2H, J=6.4 Hz), 6.58 (d, 1H, J=3.2 Hz), 6.71 (m, 1H), 6.99 (dt, 1H, J=8.4 Hz and 1.6 Hz), 7.14 (m, 2H), 7.18 (d, 1H, J=3.2 Hz), 7.32 (m, 1H), 7.48 (br s, 2H, $NH_2$), 7.91 (s, 1H). Anal. calculated for ($C_{26}H_{28}F_2N_8O$): C, 61.65; H, 5.57; F, 7.50; N, 22.12; 0, 3.16. Found C, 61.38: H, 5.66; N, 22.07.

Example 9

7-(2-(4-(2,4-Difluorophenyl)-1,4-diazepan-1-yl)ethyl)-2-(furan-2-yl)-7H-pyrrolo[3,2-e][1,2,4]triazolo[1,5-c]pyrimidin-5-amine, Method A

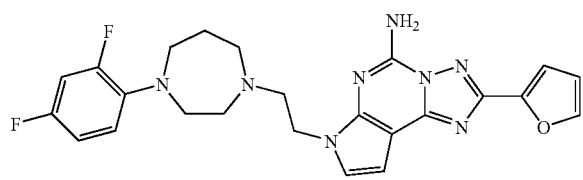

A. 1-(2,4-Difluorophenyl)-1,4-diazepane 2,4-Difluorobromobenzene (2 mmol), t-butyl 1,4-diazepane-1-carboxylate (3 mmol), $Pd_2(dba)_3$ (0.04 mmol, 4 mol % Pd, 36 mg), BINAP (0.08 mmol, 50 mg), potassium t-butoxide (KO-t-Bu, 2.8 mmol, 314 mg), and toluene (10 mL) are added to an oven-dried Schlenk flask that is purged with argon for approximately 15 min. The reaction mixture is then heated to 90° C. under argon until all of 2,4-difluorobromobenzene is consumed as determined by GC analysis. The reaction mixture is then allowed to cool to RT, diluted with EtOAc (20 mL) and filtered through a Celite pad. The filtrate is evaporated, and purified by silica gel column chromatography to afford t-butyl 4-(2,4-difluorophenyl)-1,4-diazepane-1-carboxylate which is deprotected by TFA in DCM. The reaction mixture is concentrated and the residue is extracted twice with DCM to afford 1-(2,4-difluorophenyl)-1,4-diazepane as a yellow oil: LC/MS (M+1=213.31). $^1$H NMR ($CDCl_3$, 400 MHz) δ 1.82 (br s, 1H, NH), 1.91 (quintuplet, 2H, J=6.0 Hz), 2.97 (t, 2H, J=5.6 Hz), 3.05 (t, 2H, J=5.2 Hz), 3.33 (m, 4H), 6.70-6.87 (m, 3H).

B. 7-(2-(4-(2,4-Difluorophenyl)-1,4-diazepan-1-yl)ethyl)-2-(furan-2-yl)-7H-pyrrolo[3,2-e][1,2,4]triazolo[1,5-c]pyrimidin-5-amine To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), the title A compound, 1-(2,4-difluorophenyl)-1,4-diazepane (0.33 mmol) and 0.06 mL of DIEA are added, and the solution is stirred at 100° C. for 5 h. The reaction mixture is cooled to RT, and the solvent is removed under reduced pressure. The crude product is purified by flash chromatography using a 95/5.0/0.5-mixture of DCM/MeOH/$NH_4OH$ as eluent to give 7-(2-(4-(2,4-difluorophenyl)-1,4-diazepan-1-yl)ethyl)-2-(furan-2-yl)-7H-pyrrolo[3,2-e][1,2,4]triazolo[1,5-c]pyrimidin-5-amine: LC/MS (M+1=479.01). $^1$H NMR (DMSO-$d_6$, 400 MHz) δ 1.82 (m, 2H), 2.71 (m, 2H), 2.82 (m, 2H), 2.88 (t, 2H, J=6.4 Hz), 3.24 (m, 4H), 4.22 (t, 2H, J=6.4 Hz), 6.57 (d, 1H, J=3.6 Hz), 6.71 (m, 1H), 6.85-6.94 (m, 2H), 7.09 (m, 1H), 7.14 (d, 1H, J=3.6 Hz), 7.19 (d, 1H, J=3.2 Hz), 7.51 (br s, 2H, $NH_2$), 7.92 (s, 1H).

Example 10

7-(2-(4-(2,4-Difluorophenyl)piperidin-1-yl)ethyl)-2-(furan-2-yl)-7H-pyrrolo[3,2-e][1,2,4]triazolo[1,5-c]pyrimidin-5-amine, Method A

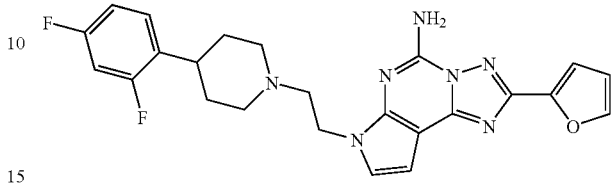

To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), 4-(2,4-difluorophenyl)piperidine (0.33 mmol) and 0.06 mL of DIEA are added, and the solution is stirred at 100° C. for 5 h. The reaction mixture is cooled to RT, and the solvent is removed under reduced pressure. The crude product is purified by flash chromatography using a 95/5.0/0.5-mixture of DCM/MeOH/$NH_4OH$ as an eluent to give 7-(2-(4-(2,4-difluorophenyl)piperidin-1-yl)ethyl)-2-(furan-2-yl)-7H-pyrrolo[3,2-e][1,2,4]triazolo[1,5-c]pyrimidin-5-amine: LC/MS (M+1=463.98). $^1$H NMR (DMSO-$d_6$, 400 MHz), δ 1.68 (m, 4H), 2.12 (m, 2H), 2.55 (m, 1H), 2.73 (t, 2H, J=6.0 Hz), 3.04 (m, 2H), 4.26 (t, 2H, J=6.4 Hz), 6.59 (d, 1H, J=3.6 Hz), 6.71 (m, 1H), 7.09 (m, 1H), 7.18 (m, 2H), 7.26 (m, 1H), 7.33 (m, 1H), 7.49 (br s, 2H, $NH_2$), 7.91 (s, 1H).

Example 11

7-(2-(2,4-Difluorophenoxy)ethyl)-2-(furan-2-yl)-7H-pyrrolo[3,2-e][1,2,4]triazolo[1,5-c]pyrimidin-5-amine, Method A

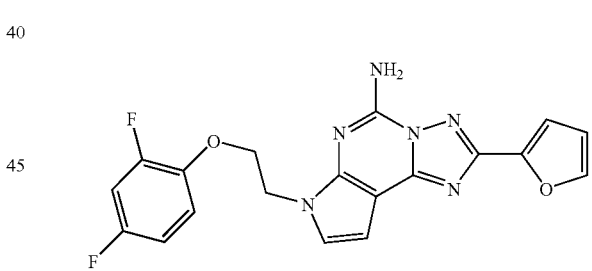

To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), 2,4-difluorophenol (0.33 mmol) and 0.06 mL of DIEA are added, and the solution is stirred at 100° C. for 5 h. The reaction mixture is cooled to RT, and the solvent is removed under reduced pressure. To the residue, acetonitrile is added and the solution is stirred at 60° C. for 0.5 h. The solution is then cooled to RT, and the resulting solids are collected by filtration to give 7-(2-(2,4-difluorophenoxy)ethyl)-2-(furan-2-yl)-7H-pyrrolo[3,2-e][1,2,4]triazolo[1,5-c]pyrimidin-5-amine: LC/MS (M+1=397.1). $^1$H NMR (DM50-$d_6$, 400 MHz) δ 4.41 (m, 2H), 4.53 (m, 2H), 6.63 (m, 1H), 6.72 (m, 1H), 6.99 (m, 1H), 7.23 (m, 4H), 7.55 (br s, 2H, $NH_2$), 7.92 (s, 1H). Anal. calculated for ($C_{19}H_{14}F_2N_6O_2$+0.5$H_2O$): C, 56.30; H, 3.73; F, 9.37; N, 20.73; 0, 9.87. Found C, 56.36; H, 3.59; N, 18.51.

Example 12

7-(2-(2,4-Difluorophenylthio)ethyl)-2-(furan-2-yl)-7H-pyrrolo[3,2-e][1,2,4]triazolo[1,5-c]pyrimidin-5-amine, Method A

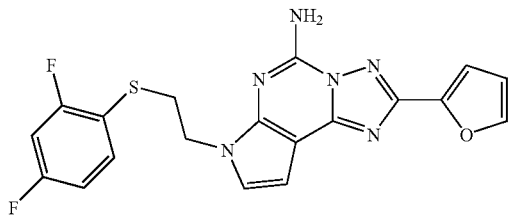

To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), 2,4-difluorobenzenethiol (0.33 mmol) and 0.06 mL of DIEA are added, and the solution is stirred at 10° C. for 5 h. The reaction mixture is cooled to RT, and the solvent is removed under reduced pressure. To the residue, acetonitrile is added and the solution is stirred at 60° C. for 0.5 h. The solution is then cooled to RT, and the resulting solids are collected by filtration to give 7-(2-(2,4-difluorophenylthio)ethyl)-2-(furan-2-yl)-7H-pyrrolo[3,2-e][1,2,4]triazolo[1,5-c]pyrimidin-5-amine: LC/MS (M+1=412.91). $^1$H NMR (DMSO-$d_6$, 400 MHz) δ 3.40 (m, 2H), 4.32 (m, 2H), 6.56 (m, 1H), 6.72 (m, 1H), 7.05 (m, 1H), 7.12 (m, 1H), 7.22 (m, 2H), 7.53 (m, 3H), 7.92 (s, 1H). Anal. calculated for ($C_{19}H_{14}F_2N_6OS$): C, 55.33; H, 3.42; F, 9.21; N, 20 38; 0, 3.88; S, 7.77. Found C, 55.01; H, 3 75; N, 21.95; S, 6.89.

Example 13

7-(2-(2,4-Difluorophenylamino)ethyl)-2-(furan-2-yl)-7H-pyrrolo[3,2-e][1,2,4]triazolo[1,5-c]pyrimidin-5-amine, Method A

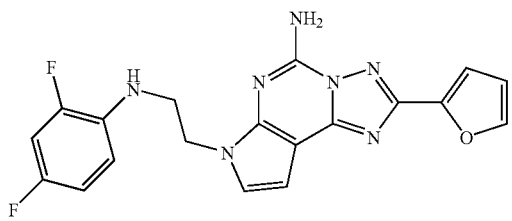

To a solution of the title D compound of Example 1, 2-{5-amino-2-(furan-2-yl)-7H-pyrrolo[3,2-e][1,2,4]triazolo[1,5-c]pyrimidin-7-yl}ethyl methanesulfonate (0.06 g, 0.165 mmol) in dry DMF (5 mL), 2,4-difluoroaniline (0.33 mmol) and 0.06 mL of DIEA are added, and the solution is stirred at 100° C. for 5 h. The reaction mixture is cooled to RT, and the solvent is removed under reduced pressure. The crude product is purified by HPLC to give 7-(2-(2,4-difluorophenylamino)ethyl)-2-(furan-2-yl)-7H-pyrrolo[3,2-e][1,2,4]triazolo[1,5-c]pyrimidin-5-amine: LC/MS (M+1=396.53).

Example 14

7-(2-(4-(2,4-Difluorophenyl)piperazin-1-yl)propyl)-2-(furan-2-yl)-7H-pyrrolo[3,2-e][1,2,4]triazolo[1,5-c]pyrimidin-5-amine, Method A

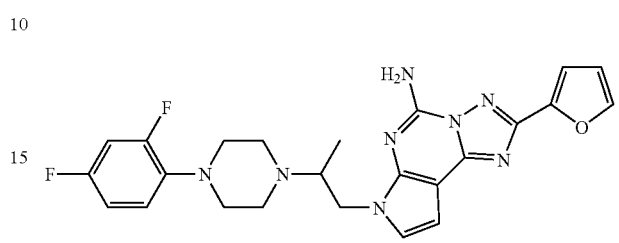

To a suspension of NaH (13.0 mg, 60 wt % in mineral oil, 0.3 mmol) in 2.0 mL of anhydrous DMF is added 2,4-difluorophenylpiperazine (63 mg, 0.32 mmol). After stirring the solution at RT for 15 min, a solution of 1-(5-amino-2-(furan-2-yl)-7H-pyrrolo[3,2-e][1,2,4]triazolo[1,5-c]pyrimidin-7-yl)propan-2-yl methanesulfonate (80 mg, 0.21 mmol) in 1.5 mL of anhydrous DMF is added. The reaction is stirred at RT under $N_2$ for 12 h. However, very little of product formation is seen by LC/MS. The reaction is then heated at 100° C. for 12 h to complete the reaction as detected by LC/MS. The crude reaction mixture is purified by chromatography to afford 7-(2-(4-(2,4-difluorophenyl)piperazin-1-yl)propyl)-2-(furan-2-yl)-7H-pyrrolo[3,2-e][1,2,4]triazolo[1,5-c]pyrimidin-5-amine: $^1$H NMR (400 MHz, $CD_2Cl_2$) δ 1.05 (d, 3H, J=6.83 Hz), 2.62-272 (m, 2H), 2.83-3.05 (m, 8H), 3.13-3.22 (m, 1H), 4.10 (dd, 1H, J=14.06 Hz and 6.64 Hz), 4.27 (dd, 1H, J=13.96 Hz and 7.52 Hz), 6.61 (dd, 1H, J=3.51 Hz and 1.76 Hz), 6.73 (d, 1H, J=3.51 Hz), 6.76-6.96 (m, 4H), 7.00 (d, 1H, J=3.32 Hz), 7.22 (dd, 1H, J=3.51 Hz and 0.78 Hz), 7.63 (dd, 1H, J=1.76 HZ and 0.78 Hz).

Example 15

7-(3-(4-(2,4-Difluorophenyl)piperazin-1-yl)butyl)-2-(furan-2-yl)-7H-pyrrolo[3,2-e][1,2,4]triazolo[1,5-c]pyrimidin-5-amine, Method A

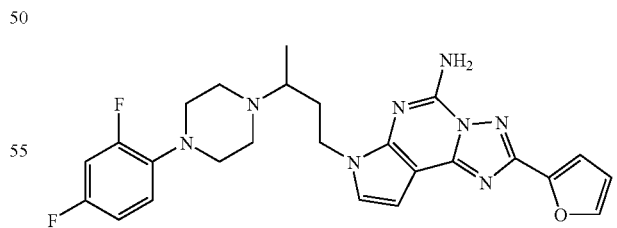

The title compound is prepared analogously as described for Example 14: $^1$H NMR (400 MHz, $CD_2Cl_2$) δ 1.01 (d, 3H, J=6.64 Hz), 1.78-2.07 (m, 2H), 2.47-2.67 (m, 3H), 2.71-2.82 (m, 2H), 2.94-3.12 (m, 5H), 4.18-4.37 (m, 2H), 5.54-5.75 (m, 2H), 6.61 (dd, 1H, J=3.32 Hz and 1.76 Hz), 6.72 (d, 1H, J=3.32 Hz), 6.76-7.03 (m, 5H), 7.20 (d, 1H, J=3.32 Hz), 7.63 (s, 1H).

Example 16

The following compounds are prepared analogously as described for the previous Examples (Method A).

TABLE 1

Method A

[Structure: R-piperazine-ethyl-N-pyrrolo-triazolo-pyrimidine with NH2 and furan substituents]

| Example No. | R | LC/MS (M + 1) | ¹H NMR δ (DMSO-d₆) |
|---|---|---|---|
| 16-1 | Methyl | 367.1 | 2.30 (s, 3 H), 2.49 (m, 4 H), 2.59 (m, 4 H), 2.79 (t, 2 H, J = 6.8 Hz), 4.28 (t, 2 H, J = 6.8 Hz), 5.86 (br s, 2 H, NH₂), 6.59 (d, 1 H, J = 12 Hz), 6.80 (m, 1 H), 6.96 (d, 1 H, J = 12 Hz), 7.25 (m, 1 H), 7.62 (s, 1 H)ª |
| 16-2 | i-Propyl | 395.2 | 1.4 (s, 6 H), 2.57 (m, 8 H), 2.63 (m, 1 H), 2.78 (t, 2 H, J = 6.4 Hz), 4.28 (t, 2 H, J = 6.4 Hz), 5.67 (br s, 2 H, NH₂), 6.58 (m, 1 H), 6.78 (m, 1 H), 6.96 (d, 1 H, J = 3.2 Hz), 7.25 (m, 1 H), 7.62 (s, 1 H)ª |
| 16-3 | Cyclopentyl | 421.2 | 1.29 (m, 2 H), 1.47 (m, 2 H), 1.58 (m, 2 H), 1.74 (m, 2 H), 2.38 (m, 8 H), 2.51 (m, 1 H), 2.65 (m, 2 H), 4.22 (m, 2 H), 6.59 (m, 1 H), 6.72 (m, 1 H), 7.17 (m, 2 H), 7.25 (br s, 2 H), 7.92 (s, 1 H) |
| 16-4 | Cyclohexyl | 435.2 | 1.15 (m, 4 H), 1.54 (m, 1 H), 1.70 (m, 4 H), 2.13 (m, 1 H), 2.45 (m, 9 H), 2.50 (t, 2 H, J = 6.0 Hz), 4.22 (t, 2 H, J = 6.0 Hz), 6.58 (d, 1 H, J = 3.2 Hz), 6.71 (m, 1 H), 7.14 (d, 1 H, J = 3.6 Hz), 7.19 (d, 1 H, J = 3.2 Hz), 7.49 (br s, 2 H, NH₂), 7.91 (s, 1 H) |
| 16-5 | Cycloheptyl | 449.2 | 1.22-1.50 (m, 8 H), 1.51-1.64 (m, 2 H), 1.65-1.75 (m, 2 H), 2.41 (m, 9 H), 2.65 (t, 2 H, J = 6.0 Hz), 4.22 (t, 2 H, J = 6.0 Hz), 6.58 (d, 1 H, J = 3.2 Hz), 6.72 (m, 1 H), 7.14 (d, 1 H, J = 3.2 Hz), 7.19 (d, 1 H, J = 3.6 Hz), 7.54 (bs, 2 H, NH₂), 7.92 (s, 1 H) |
| 16-6 | Cyclooctyl | 463.2 | 1.41 (m, 7 H), 1.54 (m, 3 H), 1.65 (m, 4 H), 2.44 (m, 8 H), 2.55 (m, 1 H), 2.66 (t, 2 H, J = 6.4 Hz), 4.22 (t, 2 H, J = 6.4 Hz), 6.59 (d, 1 H, J = 3.6 Hz), 6.12 (m, 1 H), 7.15 (d, 1 H, J = 3.2 Hz), 7.19 (d, 1 H, J = 12 Hz), 7.51 (bs, 2 H, NH₂), 7.92 (s, 1 H) |
| 16-7 | Phenyl | 429.2 | 2.61 (m, 4 H), 2.75 (t, 2 H, J = 6.8 Hz), 3.10 (m, 4 H), 4.29 (t, 2 H, J = 6.8 Hz), 6.59 (d, 1 H, J = 3.2 Hz), 6.11 (dd, 1 H, J = 3.2 Hz and 1.6 Hz), 6.76 (t, 1 H, J = 7.2 Hz), 6.91 (d, 2 H, J = 8.4 Hz), 7.17-7.22 (m, 4 H), 7.51 (br s, 2 H), 7.91 (s, 1 H) |
| 16-8 | 2-Fluorophenyl | 447.56 | 2.61 (m, 4 H), 2.74 (t, 2 H, J = 6.4 Hz), 2.94 (m, 4 H), 4.26 (t, 2 H, J = 6.4 Hz), 6.61 (d, 1 H, J = 3.6 Hz), 6.70 (m, 1 H), 6.93-7.00 (m, 2 H), 7.05 (m, 2 H), 7.15 (d, 1 H, J = 3.6 Hz), 7.21 (d, 1 H, J = 3.2 Hz), 7.39 (s, 2 H), 7.86 (s, 1 H) |
| 16-9 | 3-Fluorophenyl | 447.2 | 2.59 (m, 4 H), 2.74 (t, 2 H, J = 5 6 Hz), 3.14 (m, 4 H), 4.29 (t, 2 H, J = 5.6 Hz), 6.53 (m, 1 H), 6.60 (m, 1 H), 6.71-6.75 (m, 3 H), 7.18-7.20 (m, 3 H), 7.53 (br s, 2 H), 7.92 (s, 1 H) |
| 16-10 | 4-Fluorophenyl | 447.2 | 2.59 (m, 4 H), 2.75 (m, 2 H), 3.03 (m, 4 H), 4.28 (t, 2 H, J = 6 0 Hz), 6.60 (d, 1 H, J = 3.2 Hz), 6.71 (m, 1 H), 6.92 (m, 2 H), 7.02 (m, 2 H), 7.18 (m, 2 H), 7.51 (s, 2 H), 7.91 (s, 1 H) |
| 16-11 | 2,3-Difluorophenyl | 465.2 | 2.64 (m, 4 H), 2.76 (t, 2 H, J = 6.4 Hz), 3.02 (m, 4 H), 4.28 (t, 2 H, J = 6.4 Hz), 6.59 (d, 1 H = 3.6 Hz), 6.71 (m, 1 H), 6.83 (t, 1 H J = 8.0 Hz), 6.95 (m, 1 H), 7.07 (m, 1 H), 7.19 (m, 2 H), 7.51 (br s, 2 H), 7.92 (s, 1 H) |

TABLE 1-continued

Method A

| Example No. | R | LC/MS (M + 1) | ¹H NMR δ (DMSO-d$_6$) |
|---|---|---|---|
| 16-12 | 2,6-Difluorophenyl | 465.2 | 2.59 (m, 4 H), 2.75 (t, 2 H, J = 6.4 Hz), 3.09 (m, 4 H), 4.27 (t, 2 H, J = 6.4 Hz), 6.60 (d, 1 H, J = 3.2 Hz), 6.71 (m, 1 H), 6.99-7.06 (m, 3 H), 7.19 (m, 2 H), 7.51 (s, 2 H), 7.92 (s, 1 H) |
| 16-13 | 2,4,6-Trifluorophenyl | 483.2 | 2.57 (m, 4 H), 2.75 (t 2 H J = 6.4 Hz), 3.04 (m, 4 H), 4.27 (t, 2 H J = 6.4 Hz), 6.59 (d, 1 H J = 3.6 Hz), 6.71 (m, 1 H), 7.12 (t, 2 H, J = 9.2 Hz), 7.18 (m, 2 H), 7.50 (br s, 2 H), 7.92 (s, 1 H) |
| 16-14 | 4-Chlorophenyl | 463.1 | 2.59 (m, 4 H), 2.74 (t, 2 H, J = 6.0 Hz), 3.09 (m, 4 H), 4.28 (t, 2 H, J = 6.0 Hz), 6.60 (t, 1 H, J = 3.2 Hz), 6.71 (m, 1 H), 6.92 (dd, 2 H, J = 8.8 Hz and 2.4 Hz), 7.17-7.22 (m, 4 H), 7.52 (br s, 2 H), 7.92 (s, 1 H) |
| 16-15 | 3,4-Dichlorophenyl | 498.1 | 2.58 (m, 4 H), 2.74 (t, 2 H, J = 6.4 Hz), 3.15 (m, 4 H), 4.28 (t, 2 H, J = 6.4 Hz), 6.59 (d, 1-H, J = 3.2 Hz), 6.31 (m, 1 H), 6.92 (dd, 1 H, J = 9.2 Hz and 2.8 Hz), 7.11 (d, 1 H, J = 2.8 Hz), 7.17-7.20 (m, 2 H), 7.38 (d, 1 H, J = 9..2 Hz), 7.53 (s, 2 H), 7.92 (s, 1 H) |
| 16-16 | 4-Methylphenyl | 443.2 | 2.19 (s, 3 H), 2.60 (m, 4 H), 2.74 (m, 2 H), 3.04 (m, 4 H), 4.28 (m, 2 H), 6.60 (m, 1 H), 6.72 (m, 1 H), 6.82 (m, 2 H), 7.01 (m, 2 H), 7.19 (m, 2 H), 7.53 (s, 2 H), 7.92 (m, 1 H) |
| 16-17 | 4-Methoxyphenyl | 459.2 | 2.61 (m, 4 H), 2.74 (m, 2 H), 2 98 (m, 4 H), 3.67 (s, 3 H), 4.28 (t, 2 H, J = 6.4 Hz), 6.60 (d, 1 H, J = 3.2 Hz), 6.72 (m, 1 H), 6.80 (d, 2 H, J = 9.2 Hz), 6.87 (d, 2 H, J = 9.2 Hz), 7.18 (d, 1 H, J = 3.2 Hz), 7.19 (d, 1 H, J = 3.2 Hz), 7.53 (s, 2 H), 7.92 (s, 1 H) |
| 16-18 | 2-Fluoro-4-chlorophenyl | 481.54 | 2.65 (m, 4 H), 2.78 (m, 2 H), 2.98 (m, 4 H), 4.29 (t, 2 H, J = 6 0 Hz), 6.61 (d, 1 H, J = 3.2 Hz), 6.72 (m, 1 H), 7.02 (t, 1 H, J = 9.2 Hz), 7.15-7.21 (m, 3 H), 7.31 (dd, 1 H, J = 12.4 and 2.0 Hz), 7.53 (br s, 2 H), 7.92 (s, 1 H) |
| 16-19 | 2-Chloro-4-fluorophenyl | 481.1 | 2.64 (m, 4 H), 2.77 (t, 2 H, J = 6.4 Hz), 2.90 (m, 4 H), 4.28 (t, 2 H, J = 6.4 Hz), 6.60 (d, 1 H, J = 3.6 Hz), 6.71 (m, 1 H), 7.14-7.20 (m, 4 H), 7.38 (dd, 1 H, J = 8.8 Hz and 2.8 Hz), 7.51 (s, 2 H), 7.92 (d, 1 H, J = 1.6 Hz) |
| 16-20 | 2-Fluoro-4-bromophenyl | 526.1 | 2.63 (m, 4 H), 2.16 (t, 2 H, J = 6.4 Hz), 2.96 (m, 4 H), 4.28 (t, 2 H, J = 6.4 Hz), 6.59 (d, 1 H, J = 3.6 Hz), 6.71 (m, 1 H), 6.96 (m, 1 H), 7.18 (m, 2 H), 7.28 (dd, 1 H, J = 8.8 Hz and 2.4 Hz), 7.41 (dd, 1 H, J = 12.4 Hz and 2.4 Hz), 7.50 (s, 2 H), 7.92 (d, 1 H, J = 1.6 Hz) |
| 16-21 | 2-Bromo-4-fluorophenyl | 526.1 | 2.65 (m, 4 H), 2.77 (t, 2 H, J = 6.4 Hz), 2.89 (m, 4 H), 4.28 (t, 2 H, J = 6.4 Hz), 6.60 (d, 1 H, J = 3.2 Hz), 6.71 (m, 1 H), 7.20 (m, 4 H), 7.50 (s, 2 H), 7.53 (dd, 1 H, J = 9 6 Hz and 2.4 Hz), 7.92 (d, 1 H, J = 1.6 Hz) |
| 16-22 | 2,4-Dichlorophenyl | 498.1 | 2.64 (m, 4 H), 2.77 (t, 2 H, J = 6.4 Hz), 2.94 (m, 4 H), 4.28 (t, 2 H, J = 6.4 Hz), 6.60 (d, 1 H, J = 3.2 Hz), 6.72 (m, 1 H), 7.14 (d, 1 H, J = 8.4 Hz), 7.18 (m, 2 H), 7.34 (d, 1 H, J = 8.4 Hz), 7.50 (s, 2 H), 7.53 (m, 1 H), 7.92 (s, 1 H) |
| 16-23 | 2,4-Dimethylphenyl | 457.45 | 2.19 (s, 3 H), 2.20 (s, 3 H), 2.62 (m, 4 H), 2.76 (m, 6 H), 4.28 (t, 2 H, J = 6.4 Hz), 6.61 (m, 1 H, J = 3.2 Hz), 6.72 (dd, 1 H, J = 3.2 Hz and 1.6 Hz), 6.88 (d, 1 H, J = 8.0 Hz), 6.92 (d, 1 H, J = 8.0 Hz), 6.96 (s, 1 H), 7.18 (d, 1 H, J = 3.6 Hz), 7.20 (d, 1 H, J = 3.6 Hz), 5.53 (s, 2 H), 7.92 (d, 1 H, J = 0.4 Hz) |

TABLE 1-continued

Method A

[Structure: R-N(piperazine)N-CH2CH2-N(pyrrolo-triazolo-pyrimidine with NH2)-2-furyl]

| Example No. | R | LC/MS (M + 1) | $^1$H NMR δ (DMSO-d$_6$) |
|---|---|---|---|
| 16-24 | 3-Methoxy-5-trifluoromethylphenyl | 527.61 | 2.59 (m, 4 H), 2.75 (t, 2 H, J = 6.4 Hz), 3.19 (m, 4 H), 3.78 (s, 3 H), 4.29 (t, 2 H, J = 6.4 Hz), 6.59 (d, 2 H, J = 3.2 Hz), 6.68 (m, 1 H), 6.71 (m, 1 H), 6.77 (m, 1 H), 7.19 (t, 2 H, J = 3.2 Hz), 7.54 (br s, 2 H), 7.92 (d, 1 H, J = 1.6 Hz) |
| 16-25 | 3,5-Bis(trifluoromethyl)phenyl | 565.2 | 3.54 (m, 8 H), 3.64 (t, 2 H, J = 5.6 Hz), 4.58 (t, 2 H, J = 5.6 Hz), 6.56 (m, 1 H), 6.68 (d, 1 H, J = 3.2 Hz), 7.03 (d, 1 H, J = 3.2 Hz), 7.14 (d, 1 H, J = 3.2 Hz), 7.30 (s, 1 H), 7.41 (s, 2 H), 7.65 (s, 1 H)[b] |
| 16-26 | 4-Nitrophenyl | 474.2 | 2.61 (m, 4 H), 2.76 (t, 2 H, J = 6.4 Hz), 3.42 (m, 4 H), 4.19 (t, 2 H, J = 6.4 Hz), 6.60 (d, 1 H, J = 3.6 Hz), 6.72 (m, 1 H), 7.02 (d, 2 H, J = 9.6 Hz), 7.19 (d, 2 H, J = 3.2 Hz), 7.52 (s, 2 H), 7.92 (s, 1 H), 8.04 (d, 2 H, J = 9.6 Hz) |
| 16-27 | 2-Trifluoromethylphenyl | 497.57 | 2.61 (m, 4 H), 2.76 (t, 2 H, J = 6.0 Hz), 2.85 (m, 4 H), 4.28 (t, 2 H, J = 6.0 Hz), 6.61 (d, 1 H, J = 3.2 Hz), 6.71 (m, 1 H), 7.19 (m, 2 H), 7.32 (t, 1 H, J = 7.2 Hz), 7.50-7.55 (m, 3 H), 7.61-7.66 (m, 2 H), 7.92 (s, 1 H) |
| 16-28 | 4-Trifluoromethylphenyl | 497.2 | 2.59 (m, 4 H), 2.75 (m, 2 H), 3.23 (m, 4 H), 4.28 (m, 2 H), 6.59 (m, 1 H), 6.70 (m, 1 H), 7.04 (m, 2 H), 7.18 (m, 2 H), 7.49 (m, 4 H), 7.90 (m, 1 H) |
| 16-29 | 4-i-Propylphenyl | 471.3 | 1.14 (s, 3 H), 1.16 (s, 3 H), 2.60 (m, 4 H), 2.75 (m, 3 H), 3.05 (m, 4 H), 4.28 (t, 2 H, J = 6.4 Hz), 6.59 (d, 1 H, J = 3.2 Hz), 6.71 (m, 1 H), 6.84 (d, 2 H, J = 8.4 Hz), 7.07 (d, 2 H, J = 8.4 Hz), 7.18 (m, 2 H) 7.51 (br s, 2 H), 7.91 (s, 1 H) |
| 16-30 | 4-n-Butylphenyl | 485.2 | 0.88 (t, 3 H, J = 7.2 Hz), 1.26 (sextuplet, 2 H, J = 7.2 Hz), 1.49 (quintuplet, 2 H, J = 7.2 Hz), 2.46 (t, 2 H, J = 7.2 Hz), 2.60 (m, 4 H), 2.75 (t, 2 H, J = 6.4 Hz), 3.05 (m, 4 H), 4.28 (t, 2 H, J = 6.4 Hz), 6.59 (d, 1 H, J = 3.2 Hz), 6.71 (m, 1 H), 6.82 (d, 2 H, J = 8.8 Hz), 7.02 (d, 2 H, J = 8.8 Hz), 7.18 (m, 2 H) 7.51 (s, 2 H), 7.92 (d, 1 H, J = 1.6 Hz) |
| 16-31 | 4-t-Butylphenyl | 485.2 | 2.49 (s, 9 H), 2.60 (m, 4 H), 2.75 (t, 2 H, J = 6.4 Hz), 3.05 (m, 4 H), 4.28 (t, 2 H, J = 6.4 Hz), 6.59 (d, 1 H, J = 3.6 Hz), 6.71 (dd, 1 H, J = 3.6 Hz and 1.6 Hz), 6.84 (d, 2 H, J = 8.8 Hz), 7.18 (m, 2 H), 7.20 (d, 2 H, J = 8.8 Hz), 7.52 (s, 2 H), 7.91 (d, 1 H, J = 1.6 Hz) |
| 16-32 | 3,4-Dimethoxyphenyl | 489.2 | 2.61 (m, 4 H), 2.75 (t, 2 H, J = 6.4 Hz), 3.01 (m, 4 H), 3.66 (s, 3 H), 3.73 (s, 3 H), 4.29 (t, 2 H, J = 6.4 Hz), 6.39 (dd, 1 H, J = 8.8 Hz and 2.8 Hz), 6.58 (d, 1 H, J = 2.4 Hz), 6.60 (d, 1 H, J = 3.6 Hz), 6.71 (m, 1 H), 6.78 (d, 1 H, J = 8.8 Hz), 7.19 (m, 2 H), 7.51 (s, 2 H), 7.92 (d, 1 H, J = 1.6 Hz) |
| 16-33 | 2-Methylthiophenyl | 475.68 | 2.36 (s, 3 H), 2.63 (m, 4 H), 2.76 (t, 2 H, J = 6.4 Hz), 2.88 (m, 4 H), 4.28 (t, 2 H, J = 6.4 Hz), 6.61 (d, 1 H, J = 3.6 Hz), 6.71 (m, 1 H), 7.06-7.14 (m, 4 H), 7.19 (t, 2 H, J = 3.2 Hz), 7.52 (br s, 2 H), 7.92 (s, 1 H) |
| 16-34 | 3-Methylthiophenyl | 475.61 | 2.36 (s, 3 H), 2.60 (m, 4 H), 2.75 (m, 2 H), 3.11 (m, 4 H), 4.29 (m, 2 H), 6.60 (d, 1 H, J = 3.2 Hz), 6.71 (m, 4 H), 7.13 (m, 1 H), 7.19 (m, 2 H), 7.54 (br s, 2 H), 7.92 (s, 1 H) |
| 16-35 | 4-Trifluoromethoxyphenyl | 513.63 | 2.61 (m, 4 H), 2.75 (t, 2 H, J = 6.4 Hz), 3.12 (m, 4 H), 4.29 (t, 2 H, J = 6.4 Hz), 6.59 (d, 1 H, J = 3.6 Hz), 6.71 (m, 1 H), 6.98 (d, 2 H, J = 9.2 Hz), 7.16-7.20 (m, 4 H), 7.52 (s, 2 H), 7.91 (d, 1 H, J = 1.2 Hz) |

TABLE 1-continued

Method A

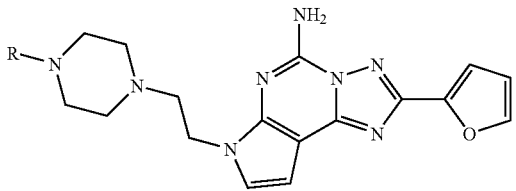

| Example No. | R | LC/MS (M + 1) | ¹H NMR δ (DMSO-d₆) |
|---|---|---|---|
| 16-36 | 2-Pyridyl | 430.26 | 2.57 (m, 4 H), 2.75 (t, 2 H, J = 6.4 Hz), 3.27 (m, 4 H), 4.29 (t, 2 H, J = 6.4 Hz), 6.59 (d, 1 H, J = 3.2 Hz), 6.71 (m, 1 H), 6.79 (d, 2 H, J = 6.4 Hz), 7.19 (t, 2 H, J = 3.2 Hz), 7.51 (br s, 2 H), 7.92 (s, 1 H), 8.44 (d, 2 H, J = 6.4 Hz) |
| 16-37 | 3-Pyridyl | 430.0 | 2.62 (m, 4 H), 2.76 (t, 2 H, J = 6.4 Hz), 3.17 (m, 4 H), 4.19 (t, 2 H, J = 6.4 Hz), 6.60 (d, 1 H, J = 3.2 Hz), 6.72 (m, 1 H), 7.19 (m, 3 H), 7.30 (dd, 1 H, J = 8.0 Hz and 2.0 Hz), 7.55 (br ss, 2 H), 7.92 (s, 1 H), 7.98 (d, 1 H, J = 4.0 Hz), 8.29 (d, 1 H, J = 2.8 Hz) |
| 16-38 | 4-Pyridyl | 430.2 | 2.55 (m, 4 H), 2.73 (m, 2 H), 3.43 (m, 4 H), 4.28 (m, 2 H), 6.60 (m, 2 H), 6.71 (m, 1 H), 6.79 (m, 1 H), 7.18 (m, 2 H), 7.51 (m, 3 H), 7.91 (s, 1 H), 8.08 (m, 1 H) |
| 16-39 | 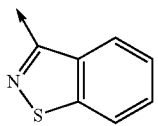 | 486.1 | 2.71 (m, 4 H), 2.80 (t, 2 H, J = 6.4 Hz), 3.42 (m, 4 H), 4.31 (t, 2 H, J = 6.4 Hz), 6.61 (d, 1 H, J = 3.6 Hz), 6.68 (m, 1 H), 6.72 (m, 1 H), 7.20 (d, 2 H, J = 3.2 Hz), 7.44 (t, 1 H, J = 7.6 Hz), 7.52 (br s, 2 H), 7.56 (t, 1 H, J = 7.6 Hz), 7.92 (s, 1 H), 8.05 (m, 2 H) |
| 16-40 | 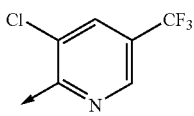 | 532.2 | 2.63 (m, 4 H), 2.73 (m, 2 H), 3.42 (m, 4 H), 4.28 (m, 2 H), 6.59 (m, 1 H), 6.71 (m, 1 H), 7.18 (m, 2 H), 7.51 (s, 2 H), 7.91 (d, 1 H, J = 2.0 Hz), 8.17 (s, 1 H), 8.53 (s, 1 H). |
| 16-41 | 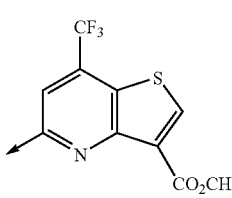 | 612.2 | 2.60 (m, 4 H), 2.77 (t, 2 H, J = 6.4 Hz), 3.70 (m, 4 H), 3.85 (s, 3 H), 4.32 (t, 2 H, J = 6.4 Hz), 6.60 (d, 1 H, J = 3.6 Hz), 6.71 (m, 1 H), 7.20 (t, 2 H, J = 3.6 Hz), 7.36 (s, 1 H), 7.52 (s, 2 H), 7.91 (s, 1 H), 8.89 (s, 1 H) |
| 16-42 | 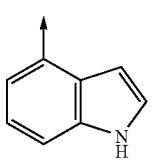 | 468.2 | 2.71 (m, 4 H), 2.80 (t, 2 H, J = 6.4 Hz), 3.11 (m, 4 H), 4.31 (t, 2 H, J = 6.4 Hz), 6.36 (m, 1 H), 6.43 (d, 1 H, J = 7.2 Hz), 6.61 (d, 1 H, J = 3.6 Hz), 6.72 (m, 1 H), 6.95 (t, 1 H, J = 7.2 Hz), 7.01 (d, 1 H, J = 8.4 Hz), 7.19 (m, 2 H), 7.23 (t, 1 H, J = 2.8 Hz), 7.51 (br s, 2 H), 7.92 (s, 1 H), 11.01 (br s, 1 H) |
| 16-43 | 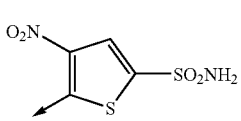 | 558.93 | 2.45 (m, 4 H), 2.68 (m, 4 H), 2.78 (t, 2 H, J = 6.4 Hz), 4.28 (t, 2 H, J = 6.4 Hz), 6.60 (d, 1 H, J = 3.6 Hz), 6.71 (m, 1 H), 7.19 (m, 2 H), 7.46 (br s, 2 H), 7.75 (m, 1 H), 7.83 (s, 1 H), 7.92 (d, 1 H, J = 2.0 Hz) |
| 16-44 | 3,4-Methylenedioxybenzyl | 487.2 | 2.32 (m, 4 H), 2.46 (m, 4 H), 2.67 (t, 2 H, J = 6.4 Hz), 3.30 (s, 2 H), 4.22 (t, 2 H, J = 6.4 Hz), 5.97 (s, 2 H), 6.58 (d, 1 H, J = 3.2 Hz), 6.72 (m, 2 H), 6.82 (m, 2 H), 7.14 (d, 1 H, J = 3.6 Hz), 7.19 |

TABLE 1-continued

Method A

R—N(piperazine)N—CH₂CH₂—[pyrrolo[3,2-e][1,2,4]triazolo[1,5-c]pyrimidine with NH₂ and furan-2-yl]

| Example No. | R | LC/MS (M + 1) | ¹H NMR δ (DMSO-d₆) |
|---|---|---|---|
| | | | (dd, 1 H, J = 3.2 Hz and 0.4 Hz), 7.49 (br s, 2 H), 7.91 (dd, 1 H, J = 1.6 Hz and 0.4 Hz) |
| 16-45 | [3,5-dimethyl-1-phenyl-1H-pyrazol-4-yl]methyl | 537.11 | 2.16 (s, 3 H), 2.24 (s, 3 H), 2.33 (m, 4 H), 2.46 (m, 4 H), 2.68 (t, 2 H, J = 6.4 Hz), 3.28 (s, 2 H), 4.22 (t, 2 H, J = 6.4 Hz), 6.58 (d, 1 H, J = 3.2 Hz), 6.71 (m, 1 H), 7.14 (d, 1 H, J = 3.2 Hz), 7.18 (d, 1 H, J = 3.2 Hz), 7.36 (m, 1 H), 7.46 (br s, 2 H), 7.47 (m, 4 H), 7.91 (d, 1 H, J = 1.6 Hz) |
| 16-46 | [1,3-dimethyl-2,4-dioxo-1,2,3,4-tetrahydropyrimidin-5-yl]methyl | 505.2 | 2.40 (m, 4 H), 2.74 (m, 2 H), 3.07 (m, 4 H), 3.18 (s, 3 H), 3.33 (s, 3 H), 4.09 (m, 2 H), 4.23 (s, 2 H), 6.59 (d, 1 H, J = 3.2 Hz), 6.71 (m, 1 H), 7.16 (m, 1 H), 7.19 (m, 1 H), 7.52 (br s, 2 H), 7.53 (m, 1 H), 7.92 (s, 1 H) |

<sup>a</sup>CDCl₃;
<sup>b</sup>CD₃OD.

Example 17

2-(Furan-2-yl)-7-(2-(4-(2-methoxyphenyl)piperazin-1-yl)ethyl)-7H-pyrrolo[3,2-e][1,2,4]triazolo[1,5-c]pyrimidin-5-amine, Method B

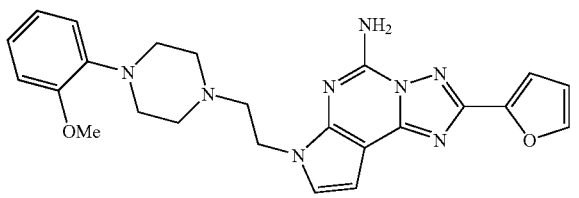

A. N'-(2-Amino-7H-pyrrolo[2,3-d]pyrimidin-4-yl)furan-2-carbohydrazide

4-Chloro-7H-pyrrolo[2,3-d]pyrimidin-2-amine (0.5 g, 2 96 mmol) and 2-furoic acid hydrazide (0.76 g, 6.0 mmol) are taken into 30 mL of n-butanol. The mixture is stirred at 120° C. under N₂ for 2 h. The solvent is evaporated in vacuum and the residue is triturated with water and filtered to afford compound N'-(2-amino-7H-pyrrolo[2,3-d]pyrimidin-4-yl)furan-2-carbohydrazide: LC/MS (M+1=259.32). This material is used in the next step without further purification.

B. 2-(Furan-2-yl)-7H-pyrrolo[3,2-e][1,2,4]triazolo[1,5-c]pyrimidin-5-amine

A mixture of the title A compound, N'-(2-amino-7H-pyrrolo[2,3-d]pyrimidin-4-yl)furan-2-carbohydrazide (0.4 g, 1.55 mmol), N,O-bis(trimethylsilyl)acetamide (1.89 g, 9.3 mmol) and 2 mL of hexamethyldisilazine is heated at 120° C. overnight. After removing volatiles under vacuum, the residue is washed with 5 mL of water and the collected solid is purified by flash chromatography using EtOAc/MeOH (95/5) as eluent to give 2-(furan-2-yl)-7H-pyrrolo[3,2-e][1,2,4]triazolo[1,5-c]pyrimidin-5-amine: LC/MS (M+1=241.0). ¹H NMR (DMSO-d₆, 400 MHz) δ 6.57 (m, 1H), 6.70 (m, 1H), 7.01 (m, 1H), 7.18 (m, 1H), 7.36 (brs, 2H, NH₂), 7.89 (s, 1H), 11.6 (br s, NH-pyrrole).

C. 2-(Furan-2-yl)-7-(2-(4-(2-methoxyphenyl)piperazin-1-yl)ethyl)-7H-pyrrolo[3,2-e][1,2,4]triazolo[1,5-c]pyrimidin-5-amine To a suspension of NaH (13 mg, 0.32 mmol) in anhydrous DMF (2 mL) at 0° C. is added slowly a solution of the title B compound, 2-(furan-2-yl)-7H-pyrrolo[3,2-e][1,2,4]triazolo[1,5-c]pyrimidin-5-amine (60 mg, 0.25 mmol) in 2 mL of anhydrous DMF. After stirring at 0° C. under N₂ for 15 min, 1-(2-chloroethyl)-4-(2-methoxyphenyl)piperazine (0.275 mmol) is added at 0° C. The mixture is warmed to RT and stirred overnight. The reaction mixture is then poured into water and extracted with DCM (3×). The organic layer is dried over anhydrous MgSO₄, filtered and concentrated in vacuo. The crude product is purified by flash chromatography using DCM/MeOH/NH₄OH (98/2/0 2) as eluent to give 2-(furan-2-yl)-7-(2-(4-(2-methoxyphenyl)piperazin-1-yl)ethyl)-7H-pyrrolo[3,2-e][1,2,4]triazolo[1,5-c]pyrimidin-5-amine: LC/MS (M+1=459.2). ¹H NMR (DMSO-d₆, 400 MHz) δ 2.56 (m, 4H), 2.67 (t, 2H, J=6.0 Hz), 2.94 (m, 4H), 3.76 (s, 3H), 4.28 (t, 2H, J=6.0 Hz), 6.60 (d, 1H, J=3.2 Hz), 6.71 (m, 1H), 6.85 (m, 2H), 6.92 (m, 2H), 7.18 (m, 2H), 7.49 (brs, NH$_2$), 7.91 (d, 1H, J=1.6 Hz).

Example 18

7-(2-(4-Fluorophenoxy)ethyl)-2-(furan-2-yl)-7H-pyrrolo[3,2-e][1,2,4]triazolo[1,5-c]pyrimidin-5-amine, Method B

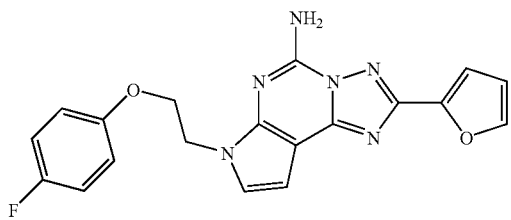

The title compound is prepared analogously as described for Example 17: LC/MS (M+1=378.94). $^1$H NMR (DMSO-d$_6$, 400 MHz) δ 4.32 (t, 2H, J=5.6 Hz), 4.50 (t, 2H, J=5.6 Hz), 6.62 (d, 1H, J=3.6 Hz), 6.71 (m, 1H), 6.94 (m, 2H), 7.09 (t, 2H, J=7.2 Hz), 7.19 (m, 2H), 7.54 (br s, 2H), 7.91 (d, 1H, J=1.6 Hz).

Example 19

7-(1-(4-(2,4-Difluorophenyl)piperazin-1-yl)propan-2-yl)-2-(furan-2-yl)-7H-pyrrolo[3,2-e][1,2,4]triazolo[1,5-c]pyrimidin-5-amine, Method B

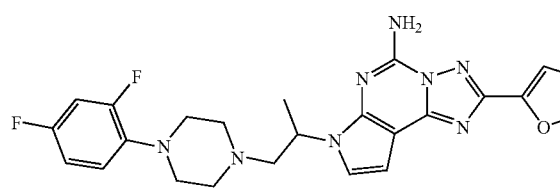

The title compound is prepared analogously as described for Example 17: $^1$H NMR (DMSO-d$_6$, 400 MHz) δ 0.92 (d, 3H, J=6.64 Hz), 2.50-2.58 (m, 2H), 279-2.89 (m, 6H), 3.10-3.19 (m, 1H), 3.98-4.02 (m, 2H), 4.05 (dd, 1H, J=13.86 Hz and 6.64 Hz), 4.20 (dd, 1H, J=13.86 Hz and 7.61 Hz), 6.57 (d, 1H, J=3.32 Hz), 6.69 (dd, 1H, J=3.32 Hz and 1.76 Hz), 6.87-7.15 (m, 2H), 7.16 (d, 2H, J=2.93 Hz), 7.44 (s, 1H), 7.89 (s, 1H).

Example 20

7-(3-(4-(2,4-Difluorophenyl)piperazin-1-yl)propyl)-2-(furan-2-yl)-7H-pyrrolo[3,2-e][1,2,4]triazolo[1,5-c]pyrimidin-5-amine, Method B

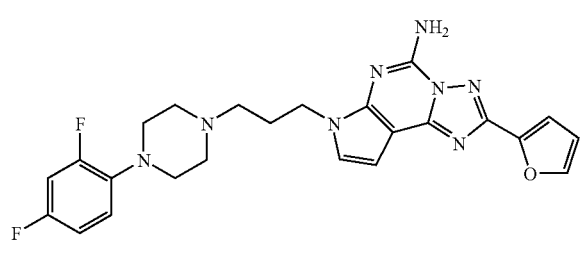

The title compound is prepared analogously as described for Example 17: $^1$H NMR (CD$_3$OD, 400 MHz) δ 2.03-2.14 (m, 2H), 2.37-2.45 (m, 2H), 2.56-2.61 (m, 4H), 3.00-3.08 (m, 4H), 4.23 (t, 2H, J=7 Hz), 6.58 (d, 1H), 6.68-6.70 (m, 5H), 7.21 (d, 1H), 7.64 (s, 1H).

Example 21

7-(4-(4-(2,4-Difluorophenyl)piperazin-1-yl)butan-2-yl)-2-(furan-2-yl)-7H-pyrrolo[3,2-e][1,2,4]triazolo[1,5-c]pyrimidin-5-amine, Method B

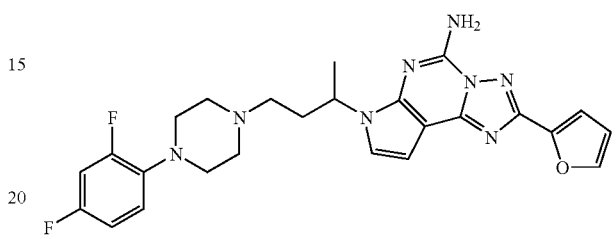

The title compound is prepared analogously as described for Example 17: $^1$H NMR (CD$_2$Cl$_2$, 400 MHz) δ 1.53 (d, 3H, J=6.83 Hz), 1.93-2.04 (m, 2H), 2.45-2.63 (m, 6H), 2.95-3.05 (m, 4H) 4.82-4.92 (m, 1H), 5.88 (s, 2H), δ 60 (br s, 1H), 6.75-6.97 (m, 4H), 7.00 (d, 1H, J=3.71 Hz), 7.21 (d, 1H, J=3.32 Hz), 7.63 (d, 1H, J=1.37 Hz).

Example 22

7-(3-(4-(2,4-Difluorophenyl)piperazin-1-yl)-2-methylpropyl)-2-(furan-2-yl)-7H-pyrrolo[3,2-e][1,2,4]triazolo[1,5-c]pyrimidin-5-amine, Method B

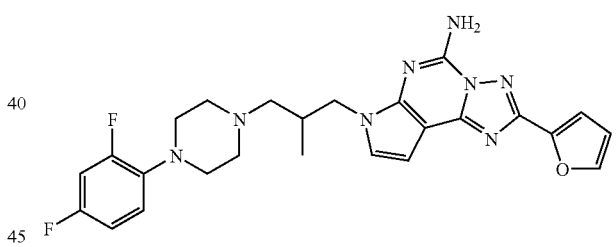

The title compound is prepared analogously as described for Example 17: $^1$H NMR (CD$_2$Cl$_2$, 400 MHz) δ 0.88 (d, 3H, J=6.05 Hz), 2.21-2.39 (m, 3H), 2.45-2.70 (m, 4H), 2.98-3.06 (m, 4H) 3.94 (dd, 1H, J=13.76 Hz and 7.13 Hz), 4.35 (dd, 1H, J=13.76 Hz and 4.59 Hz), 5.74 (s, 2H), 6.6 (m, 1H), 6.7-6.97 (m, 5H), 7.21 (d, 1H, J=3.32 Hz), 7.63 (d, 1H, J=0.78 Hz).

Example 23

7-(4-(4-(2,4-Difluorophenyl)piperazin-1-yl)but-2-ynyl)-2-(furan-2-yl)-7H-pyrrolo[3,2-e][1,2,4]triazolo[1,5-c]pyrimidin-5-amine, Method B

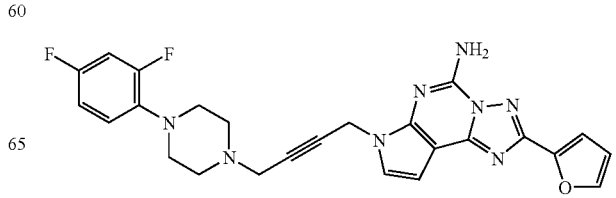

The title compound is prepared analogously as described for Example 17: ¹H NMR (CD₂Cl₂, 400 MHz) δ1.55 (s, 2H) 2.70-2.75 (m, 4H), 3.03-3.08 (m, 4H), 3.39 (t, 2H, J=1.95 Hz), 3.43 (d, 2H, J=5.27 Hz), 5.00 (t, 7H, J=1.95 Hz), 5.79 (s, 2H), 6.61 (dd, 1H, J=3.51 Hz and 1.76 Hz), 6.76-6.99 (m, 4H), 7.10 (d, 1H, J=3.51 Hz), 7.20 (dd, 1H, J=3.42, 0.68 Hz), 7.63 (dd, 1H, J=1.76 Hz and 0.78 Hz).

Example 24

N¹-(2-(5-Amino-2-(furan-2-yl)-7H-pyrrolo[3,2-e][1,2,4]triazolo[1,5-c]pyrimidin-7-yl)ethyl)-N⁴-(2,4-difluorophenyl)butane-1,4-diamine, Method C

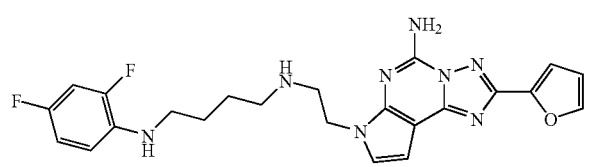

A. N'-(2,4-Difluorophenyl)butane-1,4-diamine 1,4-Diaminobutane dihydrochloride (0.97 g; 6 mmol), sodium t-butoxide (1.87 g, 19.5 mmol), rac-BINAP (61.0 mg, 0.09 mmol), and Pd(dba)₂ (35.0 mg, 0.06 mmol) are charged to a flame dried screw-cap vial. The vial is vacuumed and back filled with nitrogen. Then anhydrous toluene (15 mL) is added, followed by the addition of 1-bromo-2,4-difluorobenzene (0.34 mL, 3.00 mmol). The mixture is stirred under nitrogen at 110° C. overnight. The reaction mixture is diluted with 80 mL of diethyl ether and filtered through a pad of celite 545. The filtrate is extracted with 6N aqueous HCl (10 mL×3). The combined aqueous layers are washed twice with diethyl ether and adjusted with 1M aqueous NaOH to pH>12. The aqueous layer was extracted with diethyl ether three times. The combined ether phase is dried over anhydrous Na₂SO₄, filtered, and concentrated to obtain N'-(2,4-difluorophenyl)butane-1,4-diamine as a brown oil: ¹H NMR (CDCl₃) δ 1.55 (m, 2H), 1.66 (m, 2H), 2.74 (t, 2H), 3.12 (t, 2H), 6.55 (m, 1H), 6.73 (m, 2H).

B. N¹-(2-(5-Amino-2-(furan-2-yl)-7H-pyrrolo[3,2-e][1,2,4]triazolo[1,5-c]pyrimidin-7-yl)ethyl)-N⁴-(2,4-difluorophenyl)butane-1,4-diamine The title D compound of Example 1, 2-{5-amino-2-(furan-2-yl)-7H-pyrrolo[3,2-e][1,2,4]triazolo[1,5-c]pyrimidin-7-yl}ethyl methanesulfonate (20 mg, 0.06 mmol) and the title A compound, N'-(2,4-difluorophenyl)butane-1,4-diamine (22 mg, 0.12 mmol) are dissolved in 1 mL of n-butanol/DMF (1:1), to which solution is added 8 drops of DBU. The solution is heated at 110° C. for 1 h. The reaction is complete as indicated by TLC. The solvent is removed under vacuum and the residue is purified by flash chromatography to obtain N¹-(2-(5-amino-2-(furan-2-yl)-7H-pyrrolo[3,2-e][1,2,4]triazolo[1,5-c]pyrimidin-7-yl)ethyl)-N⁴-(2,4-difluorophenyl)butane-1,4-diamine as an off-white solid: ¹H NMR (CDCl₃) 51.51-1.68 (m, 4H), 2.7 (t, 2H, J=6.81 Hz), 3.04-3.10 (m, 4H), 4.29 (t, 2H, J=6.05 Hz), 6.50-6.57 (m, 1H), 6.58 (dd, 1H, J=3.44, 1.73 Hz), 6.66-6.78 (m, 2H), 6.80 (d, 1H, J=3.47 Hz), 6.91 (s, 1H), 7.24 (dd, 1H, J=3.44, 0.76 Hz), 7.61 (dd, 1H, J=1.73, 0.76 Hz).

Example 25

N¹-(2-(5-Amino-2-(furan-2-yl)-7H-pyrrolo[3,2-e][1,2,4]triazolo[1,5-c]pyrimidin-7-yl)ethyl)-N²-(2,4-difluorophenyl)-N²-ethylethane-1,2-diamine, Method C

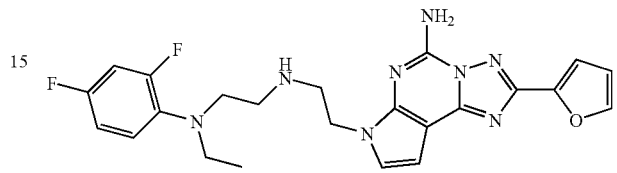

The title compound is prepared analogously as described for Example 24: ¹H NMR (CDCl₃) δ 0.94 (t, 3H, J=7.08 Hz), 2.61 (t, 2H, J=5.76 Hz), 2.85-3.24 (m, 6H), 4.24 (t, 2H, J=6.05 Hz), 5.67 (br s, 2H), 6.50-6.60 (m, 1H), 6.59-6.71 (m, 1H), 6.78-6.80 (m, 1H), 6.81-6.88 (m, 1H), 6.88 (d, 1H, J=3.4 Hz), 7.38 (dd, 1H, J=8.81 Hz and 6.17 Hz), 7.50 (dd, 1H, J=8.79 Hz and 6.20 Hz), 7.61 (m, 1H).

Example 26

N¹-(2-(5-Amino-2-(furan-2-yl)-7H-pyrrolo[3,2-e][1,2,4]triazolo[1,5-c]pyrimidin-7-yl)ethyl)-N²-(2,4-difluorophenyl)-N¹-ethylethane-1,2-diamine, Method C

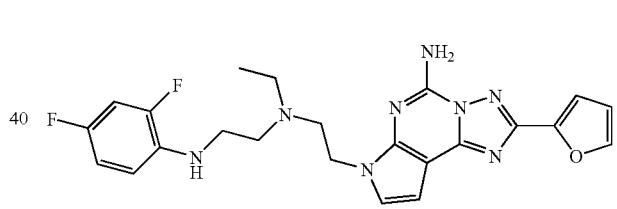

The title compound is prepared analogously as described for Example 24: ¹H NMR (CDCl₃) δ1.14 (t, 3H, J=7.20 Hz), 238-2.56 (m, 2H), 2.64-2.78 (m, 2H), 3.18-3.44 (m, 4H), 4.25-4.37 (m, 2H), 6.12-6.40 (m, 3H), 6.55-6.61 (m, 1H), 6.77-6.82 (m, 1H), 6.90 (d, 1H, J=3.47 Hz), 7.08-7.17 (m, 1H), 7.21-7.25 (m, 1H), 7.58-7.65 (m, 1H).

Example 27

N¹-(2-(5-Amino-2-(furan-2-yl)-7H-pyrrolo[3,2-e][1,2,4]triazolo[1,5-c]pyrimidin-7-yl)ethyl)-N³-(2,4-difluorophenyl)-N-methylpropane-1,3-diamine, Method C

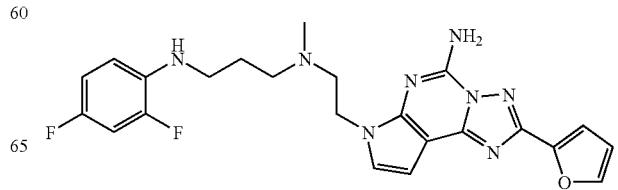

The title compound is prepared analogously as described for Example 24: $^1$H NMR (CDCl$_3$) δ 1.64-1.82 (m, 2H), 2.33 (s, 3H), 2.46-2.59 (m, 2H), 2.81 (t, 2H, J=6.56 Hz), 3.06 (m, 2H), 4.26 (t, 2H, J=6.59 Hz), 5.72 (s, 2H), 6.4-6.55 (m, 1H), 6.57 (dd, 1H, J=3.29, 1.73 Hz), 6.65-6.76 (m, 2H), 6.78 (dd, 1H, J=9.49, 3.44 Hz), 6.86 (m, 1H), 7.23 (d, 1H, J=3.42 Hz), 7.61 (d, 1H, J=0.88 Hz).

Example 28

N$_1$-(2-(5-Amino-2-(furan-2-yl)-7H-pyrrolo[3,2-e][1,2,4]triazolo[1,5-c]pyrimidin-7-yl)ethyl)-N$^4$-(2,4-difluorophenyl)-N$^1$-methylbutane-1,4-diamine, Method C

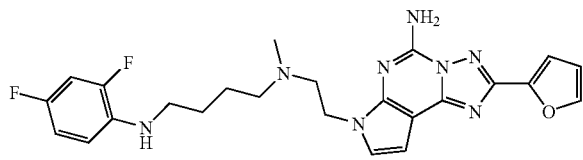

The title compound is prepared analogously as described for Example 24: $^1$H NMR (CDCl$_3$) δ 1.44-1.62 (m, 4H), 2.30 (s, 3H), 2.41 (t, 2H, J=6.74 Hz), 2.77 (t, 2H, J=6.74 Hz), 3.00 (t, 2H, J=6.37 Hz), 4.24 (t, 2H, J=6.71 Hz), 5.72 (s, 2H), 6.45-6.55 (m, 1H), 6.57 (dd, 1H, J=3.42 Hz and 1.81 Hz), 6.65-6.76 (m, 2H), 6.78 (d, 1H, J=3.47 Hz), 6.91 (dd, 1H, J=347 Hz and 1.81 Hz), 7.22 (dd, 1H, J=3.44 Hz and 0.71 Hz), 7.60 (dd, 1H, J=1.73 and 0.76 Hz).

Example 29

N$^1$-(2-(5-Amino-2-(furan-2-yl)-7H-pyrrolo[3,2-e][1,2,4]triazolo[1,5-c]pyrimidin-7-yl)ethyl)-N$^2$-(2,4-difluorophenyl)-N$^1$,N$^2$-dimethylethane-1,2-diamine, Method D

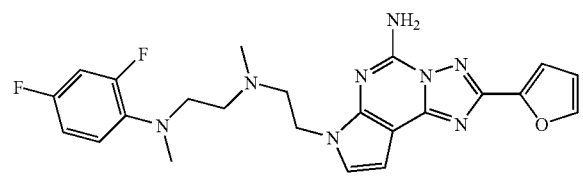

A. 7-(2-Bromoethyl)-4-chloro-7H-pyrrolo[2,3-d]pyrimidin-2-amine

4-Chloro-7H-pyrrolo[2,3-d]pyrimidin-2-amine (170 mg, 1.01 mmol), 1,2-dibromoethane (0.70 mL, 8.08 mmol), and tetra-n-butylammonium bromide (20 mg) are dissolved in THF (4 mL), and 30% aqueous NaOH (1.01 mL, 7.58 mmol) is added. The mixture is stirred for 24 h at RT, then partitioned between water and EtOAc. The aqueous solution is extracted with additional EtOAc, and the combined organic layers are dried over anhydrous sodium sulfate (Na$_2$SO$_4$), filtered and evaporated to dryness. The residue is purified by column chromatography on silica gel, eluting with 2:1-DCM:EtOAc. Fractions containing product are combined and evaporated to dryness to provide 7-(2-bromoethyl)-4-chloro-7H-pyrrolo[2,3-d]pyrimidin-2-amine as a yellow solid: LC/MS (M+1=276.9). $^1$H NMR (CDCl$_3$) δ 3.66 (t, 2H, J=8.0 Hz), 4.44 (t, 2H, J=8.0 Hz), 4.92 (br s, 2H), 6.39 (d, 1H, J=4.0 Hz), 6.92 (d, 1H, J=4.0 Hz).

B. N$^1$-(2-(2-Amino-4-chloro-7H-pyrrolo[2,3-d]pyrimidin-7-yl)ethyl)-N$^2$-(2,4-difluorophenyl)-N$^1$,N$^2$-dimethylethane-1,2-diamine To a solution of the title A compound, 7-(2-bromoethyl)-4-chloro-7H-pyrrolo[2,3-d]pyrimidin-2-amine (206.4 mg, 0.75 mmol) and N-(2,4-difluorophenyl)-N,N'-dimethylethylene-1,2-diamine (150 mg, 0.75 mmol) in 5.0 mL of anhydrous acetone is added potassium carbonate (311 mg, 2.25 mmol) at RT under positive N$_2$ pressure. The mixture is stirred at 50° C. for 24 h. The solvent is removed in vacuo after the reaction mixture is cooled down to RT. The residue is absorbed directly onto silica gel and chromatographed to yield N$^1$-(2-(2-amino-4-chloro-7H-pyrrolo[2,3-d]pyrimidin-7-yl)ethyl)-N$^2$-(2,4-difluorophenyl)-N$^1$,N$^2$-dimethylethane-1,2-diamine as a brown gummy solid.

C. N'-(2-Amino-7-(2-((2-((2,4-difluorophenyl)(methyl)amino)ethyl)(methyl)amino)ethyl)-7H-pyrrolo[2,3-d]pyrimidin-4-yl)furan-2-carbohydrazide The title B compound, N$^1$-(2-(2-amino-4-chloro-7H-pyrrolo[2,3-d]pyrimidin-7-yl)ethyl)-N$^2$-(2,4-difluorophenyl)-N$^1$,N$^2$-dimethylethane-1,2-diamine (196.8 mg, 0.50 mmol) and 2-furoic hydrazide (126.0 mg, 1.0 mmol) are dissolved in 2.0 mL of NMP. The solution is stirred at 150.0° C. for 3 h before it is cooled down to RT. The solvent is removed to afford N'-(2-amino-7-(2-((2-((2,4-difluorophenyl)(methyl)amino)ethyl)(methyl)amino)ethyl)-7H-pyrrolo[2,3-d]pyrimidin-4-yl)furan-2-carbohydrazide. LC/MS showed product as one peak.

D. N$^1$-(2-(5-Amino-2-(furan-2-yl)-7H-pyrrolo[3,2-e][1,2,4]triazolo[1,5-c]pyrimidin-7-yl)ethyl)-N$^2$-(2,4-difluorophenyl)-N$^1$,N$^2$-dimethylethane-1,2-diamine The title C compound, N'-(2-amino-7-(2-((2-((2,4-difluorophenyl)(methyl)amino)ethyl)-(methyl)amino)ethyl)-7H-pyrrolo[2,3-d]pyrimidin-4-yl)furan-2-carbohydrazide (crude from the previous step) (0.50 mmol) is dissolved in 2 mL of HMDS and 2 mL of BSA. The mixture is heated at 120° C. overnight, then cooled down to RT and the solvent removed in vacuo. The residue is dissolved in a mixture of DCM (2 mL) and 6N aqueous HCl (2 mL), and stirred at RT for 1 h. The pH value is adjusted to 12 using 1M aqueous NaOH. The organic phase is separated and the aqueous phase is extracted with additional DCM. The combined organic phase is dried over anhydrous Na$_2$SO$_4$, filtered and evaporated. The residue is purified by flash chromatography to obtain N$^1$-(2-(5-amino-2-(furan-2-yl)-7H-pyrrolo[3,2-e][1,2,4]triazolo[1,5-c]pyrimidin-7-yl)ethyl)-N$^2$-(2,4-difluorophenyl)-N$^1$,N$^2$-dimethylethane-1,2-diamine: LC/MS (M+1=467). $^1$H NMR (DMSO-d$_6$) δ 2.22 (s, 3H), 2.42-2.49 (m, 2H), 2.65 (s, 3H), 2.72 (t, 2H, 0.1=R. 37 Hz), 3.01 (t, 2H J=6.81 Hz), 4.16 (t; 2H, J=6.37 Hz), 6.57 (d, 1H, J=3.42 Hz), 6.70 (dd, 1H, J=3.39 Hz and 1.78 Hz), 6.75-6.90 (m, 2H), 7.01-7.16 (m, 2H), 7.18 (dd, 1H, J=3.39 Hz and 0.81 Hz), 7.47 (s, 2H), 7.99 (dd, 1H, J=1.73 Hz and 0.81 Hz).

Example 30

7-(2-(4-(2,4-Difluorophenyl)piperazin-1-yl)ethyl)-2-(furan-2-yl)-7H-pyrrolo[3,2-e][1,2,4]triazolo[1,5-c]pyrimidin-5-amine, Method E

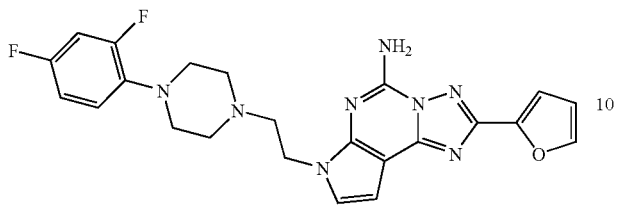

A. 4-Chloro-7-(2-(4-(2,4-difluorophenyl)piperazin-1-yl)ethyl)-7H-pyrrolo[2,3-d]pyrimidin-2-amine To a solution of the title A compound in Example 29, 7-(2-bromoethyl)-4-chloro-7H-pyrrolo[2,3-d]pyrimidin-2-amine (225 mg, 0.817 mmol) and 1-(2,4-difluorophenyl)piperazine (193 mg, 0.976 mmol) in 1 mL of dry acetone is added potassium carbonate (322 mg, 2.44 mmol). The mixture is heated at 50° C. for 24 h, cooled to RT, concentrated in vacuo, and the residue taken up in water. The aqueous mixture is repeatedly extracted with EtOAc, and the combined organic extracts are dried ($Na_2SO_4$), filtered and evaporated to dryness. The residue is purified by column chromatography on silica gel, eluting with 2% MeOH in DCM to afford 4-chloro-7-(2-(4-(2,4-difluorophenyl)piperazin-1-yl)ethyl)-7H-pyrrolo[2,3-d]pyrimidin-2-amine as a yellow solid: $^1$H NMR ($CDCl_3$) δ 2.68 (m, 4H), 2.77 (t, 2H, J=8.0 Hz), 3.01 (m, 4H), 4.19 (t, 2H, J=8.0 Hz), 4.88 (br s, 2H), 6.36 (d, 1H, J=4.0 Hz), 6.77-6.87 (m, 3H), 6.96 (d, 1H, J=4.0 Hz).

B. N'-(2-Amino-7-(2-(4-(2,4-difluorophenyl)piperazin-1-yl)ethyl)-7H-pyrrolo[2,3-d]pyrimidin-4-yl)furan-2-carbohydrazide A solution of the title A compound, 4-chloro-7-(2-(4-(2,4-difluorophenyl)piperazin-1-yl)ethyl)-7H-pyrrolo[2,3-d]pyrimidin-2-amine (75 mg, 0.19 mmol) and 2-furoic acid hydrazide (49 mg, 0.39 mmol) in 1 mL of NMP is heated at 150° C. for 3 h. After cooling to RT, the crude reaction is purified by column chromatography on silica gel, eluting with a gradient of 5% to 10% of MeOH in EtOAc. Fractions containing the product are combined and evaporated to dryness to 4-yl)furan-2-carbohydrazide as a yellow solid: LC/MS (M+1=483.2).

C. 7-(2-(4-(2,4-Difluorophenyl)piperazin-1-yl)ethyl)-2-(furan-2-yl)-7H-pyrrolo[3,2-e][1,2,4]triazolo[1,5-c]pyrimidin-5-amine The title B compound, N'-(2-amino-7-(2-(4-(2,4-difluorophenyl)piperazin-1-yl)ethyl)-7H-pyrrolo[2,3-d]pyrimidin-4-yl)furan-2-carbohydrazide (53 mg, 0.11 mmol) is dissolved in 0.5 mL of HMDS and 0.5 mL in BSA. The mixture is heated at 120° C. for 16 h, then cooled to RT and evaporated to dryness. The residue is stirred in a mixture of DCM and 6N aqueous HCl for an hour at RT, then the pH is adjusted to 9 with 1M aqueous NaOH. The organic phase is collected and the aqueous phase extracted with additional DCM. The combined organic extracts are dried ($Na_2SO_4$), filtered and evaporated. Purification of the residue by flash chromatography, eluting with 3% MeOH in DCM affords 7-(2-(4-(2,4-difluorophenyl)piperazin-1-yl)ethyl)-2-(furan-2-yl)-7H-pyrrolo[3,2-e][1,2,4]triazolo[1,5-c]pyrimidin-5-amine as an off-white solid: LC/MS (M+1=465.2). $^1$H NMR ($CDCl_3$) δ 3.01 (m, 2H), 3.25 (m, 2H), 3.39 (m, 2H), 3.52 (m, 4H), 4.86 (t, 2H, J=6.6 Hz), 5.76 (br s, 2H), 6.54 (dd, 1H, J=1.8 Hz and 3.4 Hz), 6.8-6.72 (m, 3H), 7.11 (dd, 1H, J=4.6 Hz), 7.19 (m, 2H), 7.57 (t, 1H, J=0.8 Hz).

Example 31

7-(2-(4-(2,4-Difluorophenyl)piperazin-1-yl)ethyl)-2-phenyl-7H-pyrrolo[3,2-e][1,2,4]triazolo[1,5-c]pyrimidin-5-amine, Method E

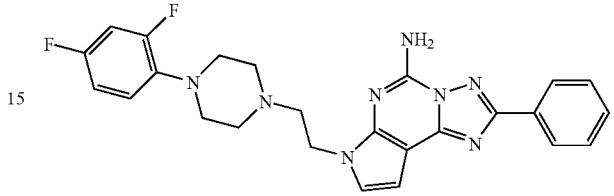

A. N'-(2-Amino-7-(2-(4-(2,4-difluorophenyl)piperazin-1-yl)ethyl)-7H-pyrrolo[2,3-d]pyrimidin-4-yl)benzohydrazide The title A compound in Example 30, 4-chloro-7-(2-(4-(2,4-difluorophenyl)piperazin-1-yl)ethyl)-7H-pyrrolo[2,3-d]pyrimidin-2-amine (150.0 mg, 0.38 mmol) and benzoyl hydrazide (104.0 mg, 0.76 mmol) are dissolved in 2.0 mL of NMP. The solution is stirred at 150.0° C. for 3 h before it is cooled down to RT. The solvent is removed by blowing a stream of $N_2$ while the vial containing the crude reaction mixture is put on low heat. The residue is taken up in MeOH and loaded onto a flash chromatography column. The column is eluted with EtOAc, then 5% on the TLC, all material that comes after the acyl hydrazide is collected. The solvent is evaporated and 1'-(2-amino-7-(2-(4-(2,4-difluorophenyl)piperazin-1-yl)ethyl)-7H-pyrrolo[2,3-d]pyrimidin-4-yl)benzohydrazide is obtained as a brownish powder: $^1$H NMR ($CDCl_3$) δ 2.68 (m, 4H), 2.76 (t, 2H, J=8.0 Hz), 3.02 (m, 4H), 4.16 (t, 2H, J=8.0 Hz), 4.64 (br s, 2H), 6.27 (d, 1H, J=4.0 Hz), δ 77-6.95 (m, 3H), 6.78 (d, 1H, J=4.0 Hz), 7.47-7.60 (m, 3H), 7.87 (m, 2H).

B. 7-(2-(4-(2,4-Difluorophenyl)piperazin-1-yl)ethyl)-2-phenyl-7H-pyrrolo[3,2-e][1,2,4]triazolo[1,5-c]pyrimidin-5-amine The title A compound, N'-(2-amino-7-(2-(4-(2,4-difluorophenyl)piperazin-1-yl)ethyl)-7H-pyrrolo[2,3-d]pyrimidin-4-yl)benzohydrazide (32.6 mg, 6.6 mmol) is suspended in 0.8 mL of HMDS and 0.8 mL of BSA, and the mixture is stirred at 120° C. for 16 h. The reaction is cooled down to RT and the solvent removed in vacuo. The residue is dissolved in a mixture of DCM (0.5 mL) and 6N aqueous HCl (0.5 mL) and stirred at RT for 1 h. The pH value is adjusted to 12 using 1M aqueous NaOH. The organic phase is separated and the aqueous phase is extracted with additional DCM. The combined organic phase is dried over anhydrous $Na_2SO_4$, filtered, and evaporated. The residue is purified by flash chromatography to obtain 7-(2-(4-(2,4-difluorophenyl)piperazin-1-yl)ethyl)-2-phenyl-7H-pyrrolo[3,2-e][1,2,4]triazolo[1,5-c]pyrimidin-5-amine as a slightly yellow powder: LC/MS (M+1=475). $^1$H NMR (DMSO-$d_6$) δ 2.62 (m, 4H), 2.76 (t, 2H, J=8.0 Hz), 2.93 (m, 4H), 4.28 (t, 2H, J=8.0 Hz), 6.62 (d, 1H, J=4.0 Hz), 6.93-7.21 (m, 3H), 7.17 (d, 1H, J=4.0 Hz), 7.49 (brs, 2H), 7.52 (m, 3H), 8.23 (m, 2H).

Example 32

The following compounds are prepared analogously as described for Examples 30 and 31 (Method E).

TABLE 2

Method E

[Structure: core scaffold with NH$_2$ group, triazolo-pyrrolopyrimidine system bearing R$_1$ and R$_2$ substituents]

| Example No. | R$_2$ | R$_1$ | $^1$H NMR δ (DMSO-d$_6$) |
|---|---|---|---|
| 32-1 | 2,4-difluorophenyl-piperazinyl-(CH$_2$)$_4$— | 2-furyl | 1.33-1.49 (m, 2 H), 1 74-1.86 (m, 2 H), 2.31 (t, 2 H), 2.39-2.51 (m, 4 H), 2.82-2.98 (m, 4 H), 4.09 (t, 2 H, J = 7.08 Hz), 5.68 (s, 1 H), 6.51 (br s, 1 H), 6.59-6.91 (m, 4 H), 7.11 (d, 1 H, J = 3.42 Hz), 7.53 (s, 1 H)[a] |
| 32-2 | 2,4-difluorophenyl-piperazinyl-(CH$_2$)$_5$— | 2-furyl | 1.28 (m, 2 H), 1.53 (m, 2 H), 1.81 (m, 2 H), 2.33 (m, 2 H) 2.50-2.61 (m, 4 H), 2.89-3.05 (m, 4 H), 4.08 (t, 2 H, J = 7.10 Hz), 5.94 (s, 1 H), 6.5 (s, 1 H), 6.64-6.88 (m, 4 H), 7.13-7.25 (m, 1 H), 7.54 (s, 1 H)[b] |
| 32-3 | 2,4-difluorophenyl-piperazinyl-(CH$_2$)$_2$—O—(CH$_2$)$_2$— | 2-furyl | 2.46-2.66 (m, 6 H), 2.78-2.98 (m, 4 H), 3.54 (t, 2 H, J = 5.39 Hz), 3.75 (t, 2 H, J = 5.37 Hz), 4.28 (t, 2 H, J = 5.37 Hz), 5.87 (br s, 2 H), 6.46-6.56 (m, 1 H), 6.60-6.80 (m, 4 H), 6.93 (d, 1 H, J = 3.47 Hz), 7.18 (d, 1 H) 7.56 (s, 1 H)[b] |
| 32-4 | 2,4-difluorophenyl-piperazinyl-CH$_2$—CH=CH—CH$_2$— (trans) | 2-furyl | 2.42-2 55 (br s, 4 H), 2.86-3.02 (m, 6 H), 4.69 (d, 2 H, J = 5.66 Hz), 5.50-5.82 (m, 4 H), 6.51 (s, 1 H), 6.64-6.91 (m, 5 H), 7.11 (d, 1 H, J = 2.88 Hz), 7.54 (s, 1 H)[a] |
| 32-5 | 2,4-difluorophenyl-piperazinyl-CH$_2$—CH=CH—CH$_2$— (cis) | 2-furyl | 2.42-2 55 (br s, 4 H), 2.86-3.02 (m, 6 H), 4.69 (d, 2 H, J = 5.66 Hz), 5.50-5.82 (m, 4 H), 6.51 (s, 1 H), 6.64-6.91 (m, 5 H), 7.11 (d, 1 H, J = 2.88 Hz), 7.54 (s, 1 H)[a] |
| 32-6 | 2,4-difluorophenyl-piperazinyl-(CH$_2$)$_2$— | 2-thienyl | 2.62 (m, 4 H), 2.75 (t, 2 H, J = 8.0 Hz), 2.93 (m, 4 H), 4.26 (t, 2 H, J = 8.0 Hz), 6.60 (d, 1 H, J = 4.0 Hz), 6.93-7.21 (m, 3 H), 7.17 (d, 1 H, J = 4.0 Hz), 7.22 (dd, 1 H), 7.45 (br s, 2 H), 7.73 (dd, 1 H), 783 (dd, 1 H) |
| 32-7 | 2,4-difluorophenyl-piperazinyl-(CH$_2$)$_2$— | tetrahydro-2-furyl | 2.19 (m, 2 H), 2.42 (m, 2 H), 2.60 (m, 4 H), 2.73 (t, 2 H, J = 8.0 Hz), 2.92 (m, 4 H), 3.82 (dd, 1 H, J = 8.0 Hz and 4.0 Hz), 3.95 (dd, 1 H, J = 8.0 Hz and 4.0 Hz), 4.25 (t, 2 H, J = 8.0 Hz), 5.03 (t, 1 H, J = 8.0 Hz), 6.54 (d, 1 H, J = 4 0 Hz), 6.93-7.35 (m, 3 H), 7.13 (d, 1 H, J = 4.0 Hz), 7.40 (br s, 2 H) |

TABLE 2-continued

Method E

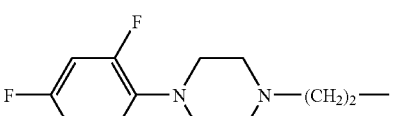

| Example No. | R₂ | R₁ | ¹H NMR δ (DMSO-d₆) |
|---|---|---|---|
| 32-8 | 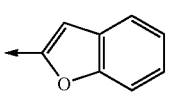 | 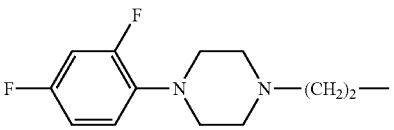 | 2.62 (m, 4 H), 276 (t, 2 H, J = 8.0 Hz), 2.93 (m, 4 H), 4.28 (t, 2 H, J = 8.0 Hz), 6.63 (d, 1 H, J = 4.0 Hz), 6.92-7.17 (m, 3 H), 7.19 (d, 1 H, J = 4.0 Hz) 7.34 (t, 1 H, J = 4.0 Hz), 7.44 (t, 1 H, J = 4.0 Hz), 7.60 (br s, 2 H), 7.66 (s, 1 H), 7.72 (d, 1 H, J = 4.0 Hz), 7.78 (d, 1 H, J = 4.0 Hz) |
| 32-9 | 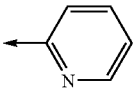 | 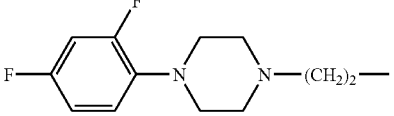 | 2.62 (m, 4 H), 2.76 (t, 2 H, J = 8.0 Hz), 2.93 (m, 4 H), 4.28 (t, 2 H, J = 8.0 Hz), 6.62 (d, 1 H, J = 4.0 Hz), 6.90-7.20 (m, 3 H), 7.18 (d, 1 H, J = 4.0 Hz), 7.52 (m, 1 H), 7.55 (br s, 2 H), 7.99 (m, 1 H), 8,28 (d, 1 H, J = 4.0 Hz), 8.72 (d, 1 H, J = 4.0 Hz) |
| 32-10 | 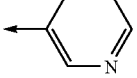 | 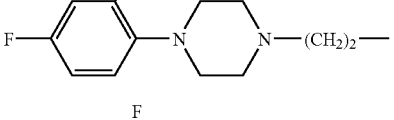 | 2.62 (m, 4 H), 276 (t, 2 H, J = 8.0 Hz), 2.93 (m, 4 H), 4.28 (t, 2 H, J = 8.0 Hz), 6.63 (d, 1 H, J = 4.0 Hz), 6.90-7.20 (m, 3 H), 7.19 (d, 1 H, J = 4.0 Hz), 7.57 (br s, 2 H), 7.60 (m, 1 H), 8.52 (dt, 1 H), 8.70 (dd, 1 H), 9.38 (d, 1 H) |
| 32-11 | 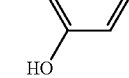 | 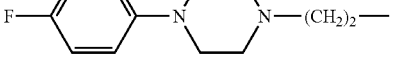 | 2.62 (m, 4 H), 2.76 (t, 2 H, J = 8.0 Hz), 2.93 (m, 4 H), 4.28 (t, 2 H, J = 8.0 Hz), 6,66 (d, 1 H, J = 4.0 Hz), 7.04 (m, 5 H), 7.21 (d, 1 H, J = 4.0 Hz), 7.39 (t, 1 H), 7.78 (br s, 1 H), 8.18 (d, 1 H), 10.86 (s, 1 H) |
| 32-12 |  | 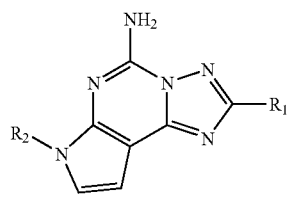 | 2.63 (s, 4 H) 2.76 (t, 2 H, J = 6.71 Hz) 2.93 (s, 4 H) 4.27 (t, 2 H, J = 6.47 Hz) 6.58 (d, 1 H, J = 3.47 Hz) 685-7.27 (m, 5 H) 7.43 (s, 2 H) 7.86 (s, 1 H) 8.37 (s, 1 H) |

[a]CD₂Cl₂;
[b]CDCl₃.

What is claimed is:

1. A compound of the formula

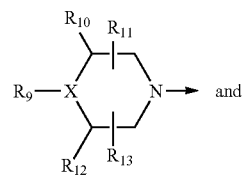

(I)

wherein

R₁ is optionally substituted $C_3$-$C_7$ cycloalkyl, optionally substituted $C_6$-$C_{10}$ aryl, optionally substituted heteroaryl or optionally substituted heterocyclyl;

R₂ is —(CR₃-R₄)$_m$—Y—(CR₅-R₆)$_n$—Z-Q in which

R₃, R₄, R₅ and R₆ are, independently from each other, hydrogen, $C_1$-$C_6$ alkyl or $C_3$-$C_{12}$ cycloalkyl;

m and n are, independently from each other, an integer from 1 to 6;

Y is absent, CH=CH, C≡C, O, S or NR₇ in which R₇ is hydrogen or $C_1$-$C_4$ alkyl;

Z is absent;

Q is a monovalent radical selected from the group consisting of

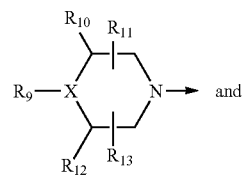 and

-continued

; in which $R_9$ is optionally substituted $C_1$-$C_6$ alkyl, optionally substituted $C_3$-$C_{12}$ cycloalkyl, optionally substituted $C_6$-$C_{10}$ aryl, optionally substituted heteroaryl, optionally substituted aralkyl, optionally substituted heteroaralkyl, heterocyclyl or acyl;

$R_{10}$ and $R_{11}$ are, independently from each other, hydrogen, optionally substituted $C_1$-$C_3$ alkyl; or $R_{10}$ and $R_{11}$, provided they are attached to the same carbon atom, combined are alkylene which together with the carbon atom to which they are attached form a 3- to 7-membered spirocyclic ring;

$R_{12}$, $R_{13}$, $R_{14}$, $R_{15}$, $R_{16}$ and $R_{17}$ are, independently from each other, hydrogen or optionally substituted $C_1$-$C_3$ alkyl;

X is N or CH;

or a pharmaceutically acceptable salt thereof.

2. A compound according to claim 1, wherein $R_1$ is 5- or 6-membered heteroaryl;

or a pharmaceutically acceptable salt thereof.

3. A compound according to claim 2, wherein $R_1$ is 2-furyl;

or a pharmaceutically acceptable salt thereof.

4. A compound according to claim 3 of the formula (IA)

wherein $R_2$ is —$(CR_3R_4)_m$—Y—$(CR_5R_6)_n$-Q in which $R_3$, $R_4$, $R_5$ and $R_6$ are, independently from each other, hydrogen or $C_1$-$C_6$ alkyl;

m is an integer of 1 or 2;

n is an integer from 1 to 4

Y is absent, CH=CH, C≡C or O;

Q is a monovalent radical selected from the group consisting of and

; in which $R_9$ is optionally substituted $C_1$-$C_6$ alkyl, optionally substituted monocyclic aryl, optionally substituted heteroaryl, optionally substituted aralkyl, optionally substituted heteroaralkyl or acyl;

$R_{10}$, $R_{11}$, $R_{12}$, $R_{13}$, $R_{14}$, $R_{15}$, $R_{16}$ and $R_{17}$ are, independently from each other, hydrogen or optionally substituted $C_1$-$C_3$ alkyl;

X is N or OH or a pharmaceutically acceptable salt thereof.

5. A compound according to claim 4, wherein $R_2$ is —$(CR_3R_4)_m$—Y—$(CR_5R_6)_n$Q in which $R_3$, $R_4$, $R_5$ and $R_6$ are, independently from each other, hydrogen or $C_1$-$C_3$ alkyl;

m is an integer of 1 or 2 n is an integer from 1 to 4

Y is absent;

Q is a monovalent radical of the formula

; in which $R_9$ is optionally substituted $C_1$-$C_6$ alkyl, optionally substituted monocyclic aryl, optionally substituted heteroaryl or acyl;

$R_{10}$, $R_{11}$, $R_{12}$ and $R_{13}$ are hydrogen;

X is N;

or a pharmaceutically acceptable salt thereof.

6. A compound according to claim 5 of the formula (IB)

wherein $R_3$, $R_4$, $R_5$ and $R_6$ are hydrogen;

m and n are 1;

$R_9$ is optionally substituted $C_1$-$C_6$ alkyl, optionally substituted monocyclic aryl, optionally substituted heteroaryl or acyl;

or a pharmaceutically acceptable salt thereof.

7. A compound according to claim 6, wherein $R_9$ is monocyclic aryl optionally substituted by 1 to 3 halogens;

or a pharmaceutically acceptable salt thereof.

8. A compound according to claim 6, wherein
R$_9$ is monocyclic aroyl optionally substituted by 1 to 3 halogens;
or a pharmaceutically acceptable salt thereof.

9. A compound according to claim 6, wherein
R$_9$ is C$_1$-C$_6$ alkyl substituted with acyl;
or a pharmaceutically acceptable salt thereof.

10. A compound according to claim 9, wherein
acyl is optionally substituted monocyclic aroyl or optionally substituted monocyclic heteroaroyl;
or a pharmaceutically acceptable salt thereof.

11. A compound according to claim 10, wherein
acyl is monocyclic aroyl optionally substituted by 1 to 3 halogens;
or a pharmaceutically acceptable salt thereof.

12. A compound according to claim 1 selected from the group consisting of:

7-(2-(4-(2,5-Difluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,4-Difluorobenzyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-((3-methylbenzo[b]thiophen-2-yl)methyl)piperazin-1-yl)ethyl)-7H-pyrrolo[3,2-e][1,2,4]triazolo[1,5-c]pyrimidin-5-amine;

7-(2-(4-(2,4-Difluorophenethyl)piperazin-1-yl)ethyl)-2-(furan-2-yl)-7H-pyrrolo[3,2-e][1,2,4]triazolo[1,5-c]pyrimidin-5-amine;

7-(2-(4-(3-(2,4-Difluorophenyl)propyl)piperazin-1-yl)ethyl)-2-(furan-2-yl)-7H-pyrrolo[3,2-e][1,2,4]triazolo[1,5-c]pyrimidin-5-amine;

(4-(2-(5-Amino-2-(furan-2-yl)-7H-pyrrolo[3,2-e][1,2,4]triazolo[1,5-c]pyrimidin-7-yl)ethyl)piperazin-1-yl)(2,4-difluorophenyl)methanone;

1-(4-(2-(5-Amino-2-(furan-2-yl)-7H-pyrrolo[3,2-e][1,2,4]triazolo[1,5-c]pyrimidin-7-yl)ethyl)piperazin-1-yl)-2-(2,4-difluorophenyl)ethanone;

1-(4-(2-(5-Amino-2-(furan-2-yl)-7H-pyrrolo[3,2-e][1,2,4]triazolo[1,5-c]pyrimidin-7-yl)ethyl)piperazin-1-yl)-3-(2,4-difluorophenyl)propan-1-one;

7-(2-(4-(2,4-Difluorophenyl)-1,4-diazepan-1-yl)ethyl)-2-(furan-2-yl)-7H-pyrrolo[3,2-e][1,2,4]triazolo[1,5-c]pyrimidin-5-amine;

7-(2-(4-(2,4-Difluorophenyl)piperidin-1-yl)ethyl)-2-(furan-2-yl)-7H-pyrrolo[3,2-e][1,2,4]triazolo[1,5-c]pyrimidin-5-amine;

7-(2-(4-(2,4-Difluorophenyl)piperazin-1-yl)propyl)-2-(furan-2-yl)-7H-pyrrolo[3,2-e][1,2,4]triazolo[1,5-c]pyrimidin-5-amine;

7-(3-(4-(2,4-Difluorophenyl)piperazin-1-yl)butyl)-2-(furan-2-yl)-7H-pyrrolo[3,2-e][1,2,4]triazolo[1,5-c]pyrimidin-5-amine;

2-(Furan-2-yl)-7-(2-(4-methylpiperazin-1-yl)ethyl)-7H-pyrrolo[3,2-e][1,2,4]triazolo[1,5-c]pyrimidin-5-amine;

2-(Furan-2-yl)-7-(2-(4-isopropylpiperazin-1-yl)ethyl)-7H-pyrrolo[3,2-e][1,2,4]triazolo[1,5-c]pyrimidin-5-amine;

7-(2-(4-Cyclopentylpiperazin-1-yl)ethyl)-2-(furan-2-yl)-7H-pyrrolo[3,2-e][1,2,4]triazolo[1,5-c]pyrimidin-5-amine;

7-(2-(4-Cyclohexylpiperazin-1-yl)ethyl)-2-(furan-2-yl)-7H-pyrrolo[3,2-e][1,2,4]triazolo[1,5-c]pyrimidin-5-amine;

7-(2-(4-Cycloheptylpiperazin-1-yl)ethyl)-2-(furan-2-yl)-7H-pyrrolo[3,2-e][1,2,4]triazolo[1,5-c]pyrimidin-5-amine;

7-(2-(4-Cyclooctylpiperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-phenylpiperazin-1-yl)ethyl)-7H-pyrrolo[3,2-e][1,2,4]triazolo[1,5-c]pyrimidin-5-amine;

7-(2-(4-(2-Fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(3-Fluorophenyl)piperazin-1-yl)ethyl)-2-(furan-2-yl)-7H-pyrrolo[32-e][1,2,4]triazolo[1,5-c]pyrimidin-5-amine;

7-(2-(4-(4-Fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,3-Difluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,6-Difluorophenyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-(2,4,6-trifluorophenyl)piperazin-1-yl)ethyl)-7H-pyrrolo[3,2-e][1,2,4]triazolo[1,5-c]pyrimidin-5-amine;

7-(2-(4-(4-Chlorophenyl)piperazin-1-yl)ethyl)-2-(furan-2-yl)-7H-pyrrolo[3,2-e][1,2,4]triazolo[1,5-c]pyrimidin-5-amine;

7-(2-(4-(3,4-Dichlorophenyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-p-tolylpiperazin-1-yl)ethyl)-7H-pyrrolo[3,2-e][1,2,4]triazolo[1,5-c]pyrimidin-5-amine;

2-(Furan-2-yl)-7-(2-(4-(4-methoxyphenyl)piperazin-1-yl)ethyl)-7H-pyrrolo[3,2-e][1,2,4]triazolo[1,5-c]pyrimidin-5-amine;

7-(2-(4-(4-Chloro-2-fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2-Chloro-4-fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(4-Bromo-2-fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2-Bromo-4-fluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,4-Dichlorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,4-Dimethylphenyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-(3-methoxy-5-(trifluoromethyl)phenyl)piperazin-1-yl)ethyl)-7H-pyrrolo[3,2-e][1,2,4]triazolo[1,5-c]pyrimidin-5-amine;

7-(2-(4-(3,5-Bis(trifluoromethyl)phenyl)piperazin-1-yl)ethyl)-2-(furan-2-yl)-7H-pyrrolo[3,2-e][1,2,4]triazolo[1,5-c]pyrimidin-5-amine 2-(Furan-2-yl)-7-(2-(4-(4-nitrophenyl)piperazin-1-yl)ethyl)-7H-pyrrolo[3,2-e][1,2,4]triazolo[1,5-c]pyrimidin-5-amine;

2-(Furan-2-yl)-7-(2-(4-(4-(trifluoromethyl)phenyl)piperazin-1-yl)ethyl)-7H-pyrrolo[3,2-e][1,2,4]triazolo[1,5-c]pyrimidin-5-amine;

2-(Furan-2-yl)-7-(2-(4-(2-(trifluoromethyl)phenyl)piperazin-1-yl)ethyl)-7H-pyrrolo[3,2-e][1,2,4]triazolo[1,5-c]pyrimidin-5-amine;

2-(Furan-2-yl)-7-(2-(4-(4-isopropylphenyl)piperazin-1-yl)ethyl)-7H-pyrrolo[3,2-e][1,2,4]triazolo[1,5-c]pyrimidin-5-amine;

7-(2-(4-(4-Butylphenyl)piperazin-1-yl)ethyl)-2-(furan-2-yl)-7H-pyrrolo[3,2-e][1,2,4]triazolo[1,5-c]pyrimidin-5-amine;

7-(2-(4-(4-t-Butylphenyl)piperazin-1-yl)ethyl)-2-(furan-2-yl)-7H-pyrrolo[3,2-e][1,2,4]triazolo[1,5-c]pyrimidin-5-amine;

7-(2-(4-(3,4-Dimethoxyphenyl)piperazin-1-yl)ethyl)-2-(furan-2-yl)-7H-pyrrolo[3,2-e][1,2,4]triazolo[1,5-c]pyrimidin-5-amine;

2-(Furan-2-yl)-7-(2-(4-(2-(methylthio)phenyl)piperazin-1-yl)ethyl)-7H-pyrrolo[3,2-e][1,2,4]triazolo[1,5-o]pyrimidin-5-amine;

2-(Furan-2-yl)-7-(2-(4-(3-(methylthio)phenyl)piperazin-1-yl)ethyl)-7H-pyrrolo[3,2-e][1,2,4]triazolo[1,5-c]pyrimidin-5-amine;

2-(Furan-2-yl)-7-(2-(4-(4-(trifluoromethoxy)phenyl)piperazin-1-yl)ethyl)-7H-pyrrolo[3,2-e][1,2,4]triazolo[1,5-c]pyrimidin-5-amine 2-(Furan-2-yl)-7-(2-(4-(pyridin-2-yl)piperazin-1-yl)ethyl)-7H-pyrrolo[3,2-e][1,2,4]triazolo[1,5-c]pyrimidin-5-amine;

2-(furan-2-yl)-7-(2-(4-(pyridin-3-yl)piperazin-1-yl)ethyl)-7H-pyrrolo[3,2-e][1,2,4]triazolo[1,5-c]pyrimidin-5-amine;

2-(Furan-2-yl)-7-(2-(4-(pyridin-4-yl)piperazin-1-yl)ethyl)-7H-pyrrolo[3,2-e][1,2,4]triazolo[1,5-c]pyrimidin-5-amine;

7-(2-(4-(Benzo[d]isothiazol-3-yl)piperazin-1-yl)ethyl)-2-(furan-2-yl)-7H-pyrrolo[3,2-e][1,2,4]triazolo[1,5-c]pyrimidin-5-amine;

7-(2-(4-(3-Chloro-5-(trifluoromethyl)pyridin-2-yl)piperazin-1-yl)ethyl)-2-(furan-2-yl)-7H-pyrrolo[3,2-e][1,2,4]triazolo[1,5-c]pyrimidin-5-amine;

Methyl 5-(4-(2-(5-amino-2-(furan-2-yl)-7H-pyrrolo[3,2-e][1,2,4]triazolo[1,5-c]pyrimidin-7-yl)ethyl)piperazin-1-yl)-7-(trifluoromethyl)thieno[3,2-b]pyridine-3-carboxylate;

7-(2-(4-(1H-Indol-4-yl)piperazin-1-yl)ethyl)-2-(furan-2-yl)-7H-pyrrolo[3,2-e][1,2,4]triazolo[1,5-c]pyrimidin-5-amine;

5-(4-(2-(5-Amino-2-(furan-2-yl)-7H-pyrrolo[3,2-e][1,2,4]triazolo[1,5-c]pyrimidin-7-yl)ethyl)piperazin-1-yl)-4-nitrothiophene-2-sulfonamide;

7-(2-(4-(Benzo[d][1,3]dioxol-5-ylmethyl)piperazin-1-yl)ethyl)-2-(furan-2-yl)-7H-pyrrolo[3,2-e][1,2,4]triazolo[1,5-c]pyrimidin-5-amine 7-(2-(4-((3,5-Dimethyl-1-phenyl-1H-pyrazol-4-yl)methyl)piperazin-1-yl)ethyl)-2-(furan-2-yl)-7H-pyrrolo[3,2-e][1,2,4]triazolo[1,5-c]pyrimidin-5-amine;

5-((4-(2-(5-Amino-2-(furan-2-yl)-7H-pyrrolo[3,2-e][1,2,4]triazolo[1,5-c]pyrimidin-7-yl)ethyl)piperazin-1-yl)methyl)-1,3-dimethylpyrimidine-2,4(1H,3H)-dione;

2-(Furan-2-yl)-7-(2-(4-(2-methoxyphenyl)piperazin-1-yl)ethyl)-7H-pyrrolo[3,2-e][1,2,4]triazolo[1,5-c]pyrimidin-5-amine;

7-(3-(4-(2,4-Difluorophenyl)piperazin-1-yl)propyl)-2-(furan-2-yl)-7H-pyrrolo[3,2-e][1,2,4]triazolo[1,5-c]pyrimidin-5-amine;

7-(1-(4-(2,4-Difluorophenyl)piperazin-1-yl)propan-2-yl)-2-(furan-2-yl)-7H-pyrrolo[3,2-e][1,2,4]triazolo[1,5-c]pyrimidin-5-amine 7-(4-(4-(2,4-Difluorophenyl)piperazin-1-yl)but-2-ynyl)-2-(furan-2-yl)-7H-pyrrolo[3,2-e][1,2,4]triazolo[1,5-c]pyrimidin-5-amine;

7-(4-(4-(2,4-Difluorophenyl)piperazin-1-yl)butan-2-yl)-2-(furan-2-yl)-7H-pyrrolo[3,2-e][1,2,4]triazolo[1,5-c]pyrimidin-5-amine;

7-(3-(4-(2,4-Difluorophenyl)piperazin-1-yl)-2-methylpropyl)-2-(furan-2-yl)-7H-pyrrolo[3,2-e][1,2,4]triazolo[1,5-c]pyrimidin-5-amine 7-(2-(4-(2,4-Difluorophenyl)piperazin-1-yl)ethyl)-2-(furan-2-yl)-7H-pyrrolo[3,2-e][1,2,4]triazolo[1,5-c]pyrimidin-5-amine;

7-(2-(4-(2,4-Difluorophenyl)piperazin-1-yl)ethyl)-2-phenyl-7H-pyrrolo[3,2-e][1,2,4]triazolo[1,5-c]pyrimidin-5-amine;

7-(4-(4-(2,4-Difluorophenyl)piperazin-1-yl)butyl)-2-(furan-2-yl)-7H-pyrrolo[3,2-e][1,2,4]triazolo[1,5-c]pyrimidin-5-amine;

7-(5-(4-(2,4-Difluorophenyl)piperazin-1-yl)pentyl)-2-(furan-2-yl)-7H-pyrrolo[3,2-e][1,2,4]triazolo[1,5-c]pyrimidin-5-amine;

7-(2-(2-(4-(2,4-Difluorophenyl)piperazin-1-yl)ethoxy)ethyl)-2-(furan-2-yl)-7H-pyrrolo[3,2-e][1,2,4]triazolo[1,5-c]pyrimidin-5-amine (E)-7-(4-(4-(2,4-Difluorophenyl)piperazin-1-yl)but-2-enyl)-2-(furan-2-yl)-7H-pyrrolo[3,2-e][1,2,4]triazolo[1,5-c]pyrimidin-5-amine (Z)-7-(4-(4-(2,4-Difluorophenyl)piperazin-1-yl)but-2-enyl)-2-(furan-2-yl)-7H-pyrrolo[3,2-e][1,2,4]triazolo[1,5-c]pyrimidin-5-amine;

7-(2-(4-(2,4-Difluorophenyl)piperazin-1-yl)ethyl)-2-(thiophen-2-yl)-7H-pyrrolo[3,2-e][1,2,4]triazolo[1,5-c]pyrimidin-5-amine;

7-(2-(4-(2,4-Difluorophenyl)piperazin-1-yl)ethyl)-2-(tetrahydrofuran-2-yl)-7H-pyrrolo[3,2-e][1,2,4]triazolo[1,5-c]pyrimidin-5-amine 2-(Benzofuran-2-yl)-7-(2-(4-(2,4-difluorophenyl)piperazin-1-yl)ethyl)-7H-pyrrolo[3,2-e][1,2,4]triazolo[1,5-c]pyrimidin-5-amine;

7-(2-(4-(2,4-Difluorophenyl)piperazin-1-yl)ethyl)-2-(pyridin-2-yl)-7H-pyrrolo[3,2-e][1,2,4]triazolo[1,5-c]pyrimidin-5-amine;

7-(2-(4-(2,4-Difluorophenyl)piperazin-1-yl)ethyl)-2-(pyridin-3-yl)-7H-pyrrolo[3,2-e][1,2,4]triazolo[1,5-c]pyrimidin-5-amine;

2-(5-Amino-7-(2-(4-(2,4-difluorophenyl)piperazin-1-yl)ethyl)-7H-pyrrolo[3,2-e][1,2,4]triazolo[1,5-c]pyrimidin-2-yl)phenol; and 7-(2-(4-(2,4-Difluorophenyl)piperazin-1-yl)ethyl)-2-(furan-3-yl)-7H-pyrrolo[3,2-e][1,2,4]triazolo[1,5-c]pyrimidin-5-amine;

or a pharmaceutically acceptable salt thereof.

13. A method of treating Parkinson's disease comprising administering to a mammal, in need thereof, a therapeutically effective amount of a compound according to claim 1, or a pharmaceutically acceptable salt thereof.

14. A method of treating cirrhosis comprising administering to a mammal, in need thereof, a therapeutically effective amount of a compound according to claim 1, or a pharmaceutically acceptable salt thereof.

15. A pharmaceutical composition comprising a therapeutically effective amount of at least one compound of claim 1 in combination with one or more pharmaceutically acceptable carriers.

16. The pharmaceutical composition according to claim 15, for the treatment of Parkinson's disease.

17. The pharmaceutical composition according to claim 15, wherein the medical condition is for the treatment of cirrhosis.

* * * * *

UNITED STATES PATENT AND TRADEMARK OFFICE
CERTIFICATE OF CORRECTION

PATENT NO. : 7,691,869 B2  Page 1 of 1
APPLICATION NO. : 12/056403
DATED : April 6, 2010
INVENTOR(S) : Allan R. Moorman It is certified that error appears in the above-identified patent and that said Letters Patent is hereby corrected as shown below:

Column 11, lines 6 to 12, the structure should appear as follows:

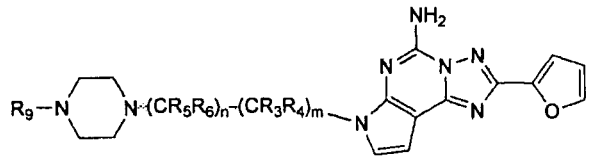

Column 27, line 63, "3H" should be changed to --$^{3}$H--.

Column 74, line 18 (claim 4), "OH" should be changed to --CH--.

Signed and Sealed this

Sixth Day of July, 2010

David J. Kappos
*Director of the United States Patent and Trademark Office*